(12) United States Patent
Peschanski et al.

(10) Patent No.: US 10,654,838 B2
(45) Date of Patent: May 19, 2020

(54) AMINOPYRIDINE COMPOUNDS USEFUL AS INHIBITORS OF PROTEIN PRENYLATION

(71) Applicants: INSTITUT NATIONAL DE LA SANTE ET DE LA RECHERCHE MEDICALE (INSERM), Paris (FR); ASSOCIATION FRANCAISE CONTRE LES MYOPATHIES, Paris (FR); UNIVERSITE D'EVRY VAL D'ESSONNE, Evry (FR)

(72) Inventors: Marc Peschanski, Evry (FR); Sophie Blondel, Evry (FR); Xavier Nissan, Evry (FR)

(73) Assignees: INSTITUT NATIONAL DE LA SANTE ET DE LA RECHERCHE MEDICALE (INSERM), Paris (FR); ASSOCIATION FRANCAISE CONTRE LES MYOPATHIES, Paris (FR); UNIVERSITE D'EVRY VAL D'ESSONNE, Evry (FR)

( * ) Notice: Subject to any disclaimer, the term of this patent is extended or adjusted under 35 U.S.C. 154(b) by 0 days.

(21) Appl. No.: 15/518,127

(22) PCT Filed: Oct. 7, 2015

(86) PCT No.: PCT/EP2015/073141
§ 371 (c)(1),
(2) Date: Apr. 10, 2017

(87) PCT Pub. No.: WO2016/055517
PCT Pub. Date: Apr. 14, 2016

(65) Prior Publication Data
US 2017/0305892 A1 Oct. 26, 2017

(30) Foreign Application Priority Data
Oct. 8, 2014 (EP) ..................................... 14306578

(51) Int. Cl.
C07D 409/14 (2006.01)
C07D 403/12 (2006.01)
(Continued)

(52) U.S. Cl.
CPC ......... *C07D 409/14* (2013.01); *C07D 401/02* (2013.01); *C07D 401/06* (2013.01);
(Continued)

(58) Field of Classification Search
None
See application file for complete search history.

(56) References Cited

U.S. PATENT DOCUMENTS

2005/0182067 A1 8/2005 Balan et al.
2006/0281755 A1 12/2006 Baumann et al.
2007/0060594 A1 3/2007 Schwarz et al.

FOREIGN PATENT DOCUMENTS

CN 101242837 A 8/2008
EP 1110957 A1 6/2001
(Continued)

OTHER PUBLICATIONS

Palsuledesai et al., Protein Prenylation: Enzymes, Therapeutics, and Biotechnology Applications. ACS Chemical Biology, 2015, 10, 51-62.*
(Continued)

*Primary Examiner* — Po-Chih Chen
(74) *Attorney, Agent, or Firm* — Oliff PLC

(57) ABSTRACT

A compound for use in the treatment and/or prevention of diseases or disorders wherein an inhibition of protein prenylation is required, which is alternatively chosen among (1)

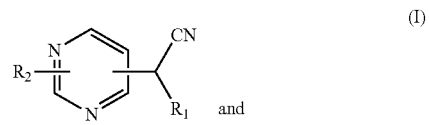

and (2)

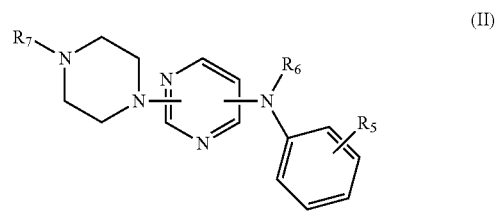

wherein $R_1$ is 2-pyridyl, 3-pyridyl or 4-pyridyl; $R_2$ represents:

(Continued)

and wherein $R_5$ and $R_6$ represent a hydrogen atom or a $(C_{1-4})$alkyl group; and $R_7$ represents an arylcarbonyl group, a heteroarylcarbonyl group, a heteroarylacetyl group, a $(C_1$-$C_4)$alkoxy-carbonylmethyl group, a

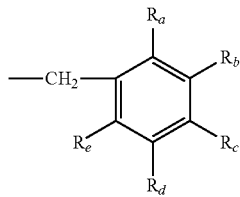

group. Also disclosed are novel compounds of formulae (I) and (II).

16 Claims, 12 Drawing Sheets

Specification includes a Sequence Listing.

(51) Int. Cl.
  *C07D 401/14* (2006.01)
  *C07D 405/14* (2006.01)
  *C07D 401/06* (2006.01)
  *C07D 401/02* (2006.01)
(52) U.S. Cl.
  CPC ......... *C07D 401/14* (2013.01); *C07D 403/12* (2013.01); *C07D 405/14* (2013.01)

(56) References Cited

FOREIGN PATENT DOCUMENTS

JP  2006-525281 A  11/2006
JP  2007-522233 A  8/2007

OTHER PUBLICATIONS

Schafer, S., Kolkhof, P. Failure is an option: learning from unsuccessful proof-of-concept trials. Drug Discovery Today. Nov. 2008, 13, 913-916.*
Horig, H., Pullman, W. From bench to clinic and back: Perspective on the 1st IQPC Translational Research conference. Journal of Translational Medicine. Dec. 2004, 2, 44.*
Chemical Abstract Registry No. 901661-46-9, indexed in the Registry File on STN CAS Online Aug. 16, 2006.*
Ito et al., A medium-term rat liver bioassay for rapid in vivo detection of carcinogenic potential of chemicals. Cancer Science, 2003, 94, 3-8.*
Gozalbes, Rafael et al., "Supporting Information Title: Development and experimental validation of a docking strategy for the generation of kinase-targeted libraries.", http://pubs.acs.org/doi/suppl/10.1021/jm701367r/suppl_file/im701367r-file001.pdf, pp. S1-S20, (2005).
Moorthy, N.S.H.N. et al., "Farnesyltransferase Inhibitors: A Comprehensive Review Based on Quantitative Structural Analysis.", Current Medicinal Chemistry, Bentham Science Punlishers, NL, vol. 20, No. 38, pp. 4888-4923, (2013).
Nov. 25, 2015 International Search Report issued in Patent Application Np. PCT/EP2015/073141.

* cited by examiner

AMINOPYRIDINE COMPOUNDS USEFUL AS INHIBITORS OF PROTEIN PRENYLATION

FIELD OF THE INVENTION

The present invention relates to the field of the prevention or treatment of diseases or disorders involving a deregulation of protein prenylation, which includes the prevention or treatment of progeria.

BACKGROUND OF THE INVENTION

Prenylation consists of the addition of an isoprenoid group to a cysteine residue located near the carboxyl terminal of a protein. This enzymatic posttranslational modification is important for the maturation and processing of proteins. Both processes are necessary to mediate protein-protein and membrane-protein associations, in addition to regulating the localisation and function of proteins. The severe phenotype of animals deficient in enzymes involved in both prenylation and maturation highlights the significance of these processes. Moreover, alterations in the genes coding for isoprenylated proteins or enzymes that are involved in both prenylation and maturation processes have been found to be the basis of severe human diseases, such as cancer, neurodegenerative disorders, retinitis pigmentosa, and premature ageing syndromes. Recent studies on isoprenylation and postprenylation processing in pathological conditions have unveiled surprising aspects of these modifications and their roles in different cellular pathways. The identification of these enzymes as therapeutic targets has led researchers to validate their effects in vitro and in vivo as antitumour or antiageing agents.

Hutchinson-Gilford progeria syndrome (HGPS) is an ultra-rare segmental premature aging disease resulting in early death from heart attack or stroke. There is no approved treatment, but starting in 2007, several recent single arm clinical trials have administered inhibitors of protein farnesylation aimed at reducing toxicity of the disease-producing protein progerin. No study has assessed whether treatments influence patient survival.

Identification of the molecular mechanisms leading to premature aging in children affected by Hutchinson Gilford progeria syndrome (HGPS) (OMIM #176670) has allowed clinicians to test targeted repurposed drugs. However, up to now, the lack of appropriate in vitro cellular models has precluded wider assays of chemical entities using high throughput screening (HTS).

HGPS is an extremely rare genetic disease (Merideth et al., 2008, N Engl J Med, Vol. 358: 592-604) due to a single-base substitution in exon 11 of the LMNA gene (De Sandre-Giovannoli et al., 2003, Science, Vol. 300: 2055; Eriksson et al., 2003, Nature, Vol. 423: 293-298) (c.1824C>T, NCBI Reference Sequence: 170707.3). This leads to the activation of a cryptic splicing donor site yielding to the deletion of 50 amino acids in prelamin A and the production of a toxic form of the prelamin A protein called progerin (Navarro et al., 2004, Hum Mol Genet, Vol. 13: 2493-2503).

Because the deleted sequence is required to its posttranslational maturation, this mutant protein accumulates at the nuclear membrane, and this is the main mechanism leading to segmental premature and accelerated aging in patients. While the disorganization of the nuclear shape is easily observed in HGPS cells, a set of well characterized cellular dysfunctions is associated, including premature senescence as well as defects in DNA repair, cell proliferation and differentiation.

Since the discovery of the molecular mechanisms leading to HGPS, three different drugs have been repurposed for their ability to target the prenylation process, namely the HMG-CoA reductase (GCR) inhibitor pravastatin associated to the amino-bisphosphonate zoledronate, and the farnesyl transferase inhibitor (FTI) lonafarnib (Varela et al., 2008, Nat Med, Vol. 14: 767-772; Yang et al., 2005, Proc Natl Acad Sci USA, Vol. 102: 10291-10296; Yang et al., 2010, Journal of lipid research, Vol. 51: 400-405). Over the past 10 years, several experimental studies have indeed demonstrated the relevance of these pharmacological approaches showing that inhibition of the prelamin A prenylation process correlated with an improvement of the nuclear shape and other cellular defects related to HGPS. Altogether these studies have triggered the elaboration of three clinical trials (Capell et al., 2005, Proc Natl Acad Sci USA, Vol. 102: 12879-12884; Capell et al., 2008, Proc Natl Acad Sci USA, Vol. 105: 15902-15907; G1 and Glover, 2005, Human Mol Genet, Vol. 14: 2959-2969; Varela et al., 2008, Nat Med, Vol. 14: 767-772; Young et al., 2013, Sci Transl Med Vol. 5: 171ps173) that revealed some partial improvements of patients' clinical phenotypes, making it essential to discover new potential molecules (Gordon et al., 2012, Proc Natl Acad Sci USA, Vol. 109: 16666-16671).

Thanks to their pluripotency and self-renewal properties, embryonic stem cells and (ES) induced pluripotent stem (iPS) cells offer a unique way to produce an unlimited and homogeneous biological resource for testing chemical compounds in vitro, in a HTS setting (Desbordes and Studer, 2013, Nat Protoc, Vol. 8: 111-130; Lee et al., 2012, Nat Biotechnol, Vol. 30: 1244-1248). Since 2011, several groups have demonstrated the capacity of iPS cell lines to recapitulate some aspects of HGPS after differentiation into vascular smooth muscle cells (VSMCs) and mesenchymal stem cells (MSCs) (Liu et al., 2011, Nature, Vol. 472: 221-225; Nissan et al., 2012, Cell Rep, Vol. 2: 1-2; Zhang et al., 2011, Cell Stem Cell, Vol. 8: 31-45). More recently it has been shown that those cells could be used to evaluate, in vitro, the functional effects of the drugs that are currently used in HGPS patients on typical cellular and molecular defects, such as nuclear shape architecture, progerin expression and their premature differentiation along the osteoblastic lineage (Blondel et al., 2014, Stem cells Transl Med, Vol. 3: 510-519).

There is a need in the art for the availability of further compounds useful in the prevention or in the treatment of diseases or disorders wherein an inhibition of protein prenylation is required.

SUMMARY OF THE INVENTION

It has now been found that novel compounds belonging to a class of aminopyridine compounds of formulae (I), (II), (Ia), (Ib), (Ic) and (I'a) as defined hereinafter are able to inhibit protein prenylation and more precisely protein farnesylation, while being devoid of toxicity.

The present invention therefore relates to compounds of formulae (I), (II), (Ia), (Ib), (Ic) and (I'a) as defined below for use in the treatment and/or prevention of diseases or disorders wherein an inhibition of protein prenylation is required.

The present invention moreover relates to compounds of formulae (I), (II), (Ia), (Ib), (Ic) and (I'a) as defined below for use as medicines.

The present invention further relates to compounds of formulae (I), (II), (Ia), (Ib), (Ic) and (I'a) as such, as defined below.

The present invention also provides pharmaceutical compositions comprising at least one of said novel compounds and at least one pharmaceutically acceptable excipient.

Each chart represents cell viability (upper curve) and percentage of prelamin A positive nuclei (lower curve). Each point represents the mean +/−SD of the percentage of 8 replicates.

FIG. 2: Pharmacological evaluation of the 5 prelamin A modulators on HGPS defects (2A) Measure of nuclear shape abnormalities (lamin A/C immunostaining) in HGPS MSCs following 48 hours of treatments with each of the 5 prelamin A modulators (Mono-AP1, Mono-AP2, Mono-AP3, Di-AP1 and Di-AP2). Each chart represents the mean +/−SD of 8 independent experiments.

(2B) Measure of osteogenic differentiation (Alkaline phosphatase activity) in HGPS MSCs following 7 days of differentiation in presence of each of the 5 prelamin A modulators (Mono-AP1, Mono-AP2, Mono-AP3, Di-AP1 and Di-AP2). Each chart represents the mean +/−SD of 8 independent experiments. Data are normalized on cell number.

(2C) Measure of cell proliferation (Ki-67 unostaining) in HGPS MSCs following 48 hours of treatments with each of the 5 prelamin A modulators (Mono-AP1, Mono-AP2, Mono-AP3, Di-AP1 and Di-AP2). Each chart represents the mean +/−SD of 8 independent experiments.

FIG. 3: Structure-Activity-Relationship of Mono-APs (A) Automated quantification of prelamin A-stained nuclei in HGPS MSCs following 48 hours of treatment with 47 compounds containing a Mono-APs domain at 10 μM. Data are compared to FTI 1 μM (in red). Each value represents the mean +/−SD of the percentage of 4 replicates.

(B) Dose response analysis of the 9 hits identified as positives (Mono-AP21, Mono-AP28, Mono-AP26, Mono-AP9, Mono-AP30, Mono-AP25, Mono-AP27, Mono-AP16, Mono-AP24) on prelamin A maturation process in HGPS MSCs. Each point represents the mean +/−SD of the percentage of 8 replicates.

(C) Cellular viability of HGPS MSCs after the treatment with the 9 hits identified as positives (Mono-AP21, Mono-AP28, Mono-AP26, Mono-AP9, Mono-AP30, Mono-AP25, Mono-AP27, Mono-AP16, Mono-AP24). Each point represents the mean +/−SD of the percentage of 8 replicates.

Figure 4:
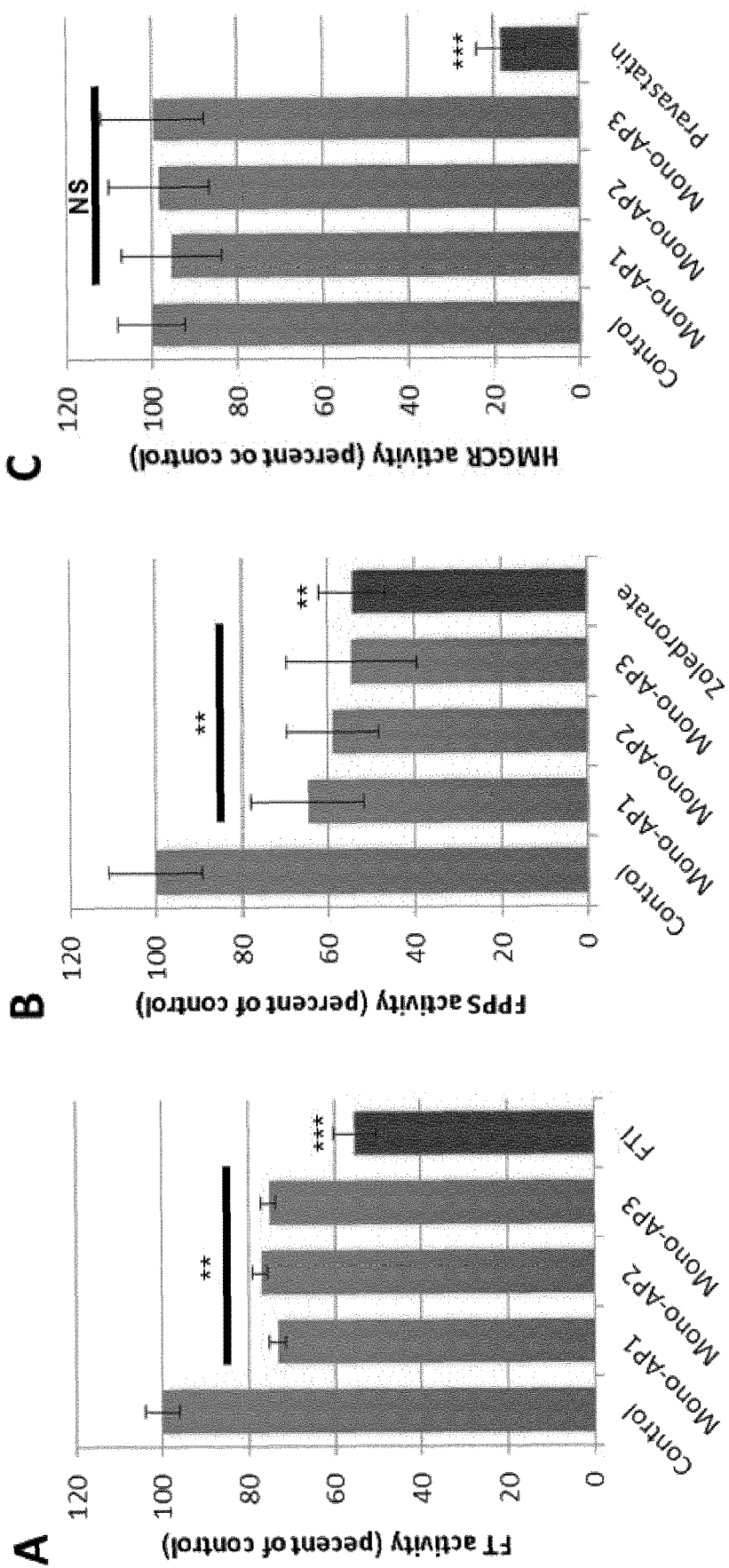

FIG. 4: Molecular docking of Mono-APs on HMG-CoA reductase (HMGCR), farnesyl pyrophosphate synthase (FPPS) and farnesyl transferase (FT)

(4A) Measure of FT activity in presence of Mono-AP1 25 μM, Monop-AP2 50 μM and Mono-AP3 50 μM. Tipifarnib 1 μM (FTI) was used as positive control. Results are presented in percent of control. Each point represents the mean +/−SD of the percentage of 8 replicates.

(4B) Measure of FPPS activity in presence of Mono-AP1 25 μM, Monop-AP2 50 μM and Mono-AP3 50 μM. Zoledronate 1 μM was used as positive control. Results are presented in percent of control. Each point represents the mean +/−SD of the percentage of 8 replicates.

Figure 5:
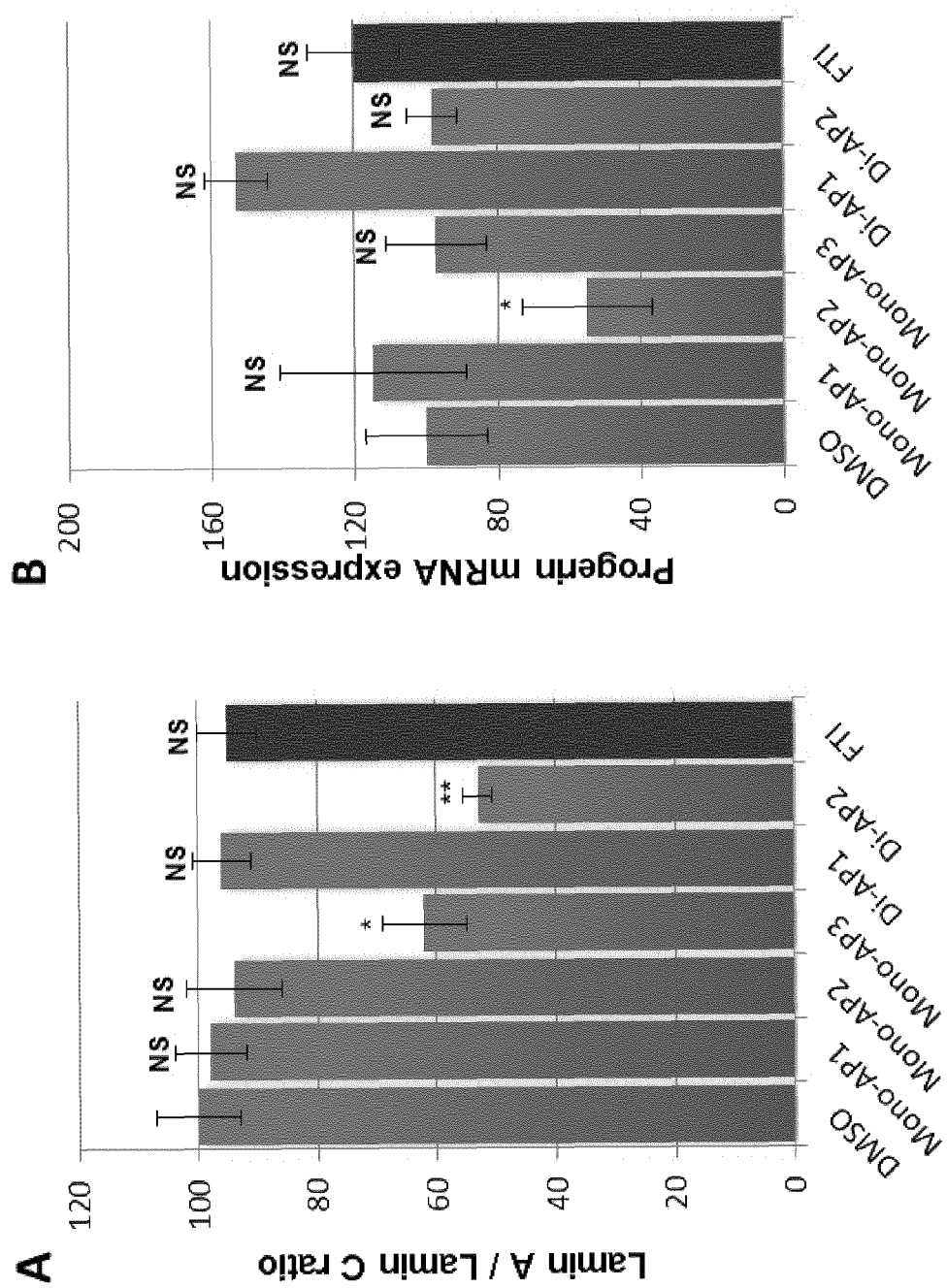

(4C) Measure of HMGCR activity in presence of Mono-AP1 25 μM, Monop-AP2 50 μM and Mono-AP3 50 μM. Pravastatin 1 μM was used as positive control. Results are presented in percent of control. Each point represents the mean +/−SD of the percentage of 8 replicates FIG. 5: Effect of the 5 validated compounds on prelamin A maturation process (5A) Gene expression analysis of lamin A/C ratio in HGPS MSC following 48 hours of treatments with each of the 5 validated compounds (Mono-AP1, Mono-AP2, Mono-AP3, Di-AP1 and Di-AP2). Data are normalized on DMSO 0.1% treated HOPS MSC. Each chart represents the mean +/−SD of three independent experiments.

(5B) Gene expression analysis of progerin expression in HGPS MSC following 48 hours of treatments with each of the 5 validated compounds (Mono-AP1, Mono-AP2, Mono-AP3, Di-AP1 and Di-AP2). Data are normalized on DMSO 0.1% treated HGPS MSC. Each chart represents the mean +/−SD of three independent experiments.

Figure 6:
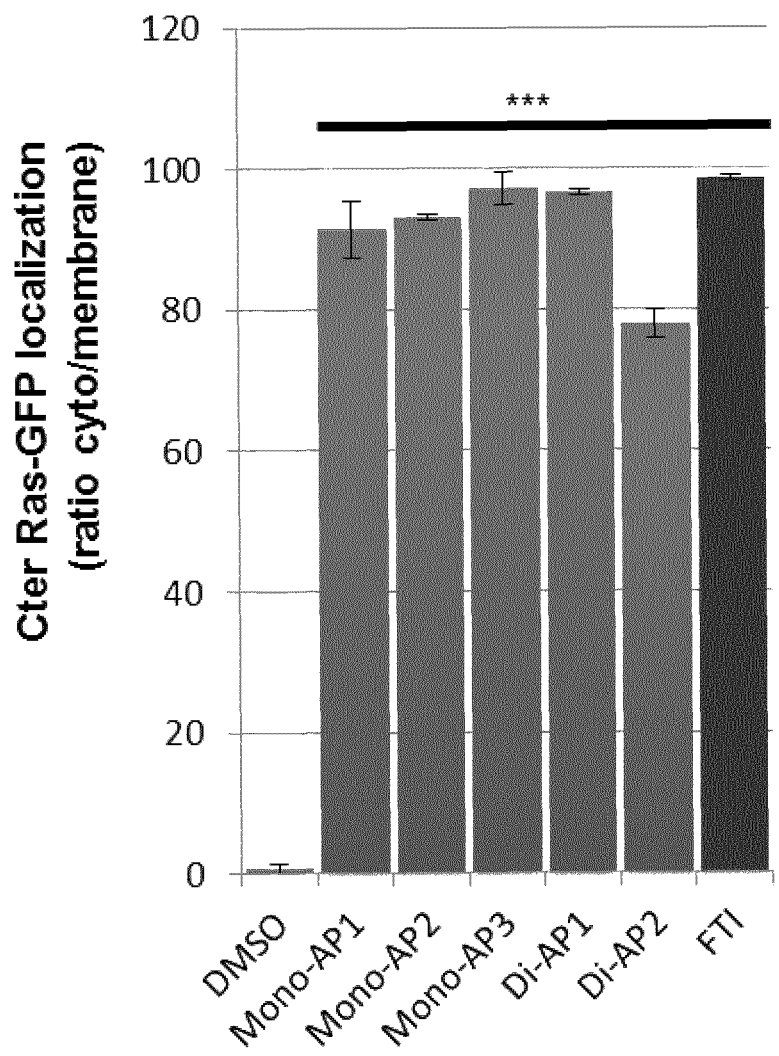

FIG. 6: Analysis of hits effects on HDJ2 and hRAS farnesylation

Quantification of the percentage of HGPS MSCs presenting a cytoplasmic (unfarnesylated) localization of GFP following 48 hours of treatments with each of the 5 prelamin A modulators (Mono-AP1, Mono-AP2, Mono-AP3, Di-AP1 and Di-AP2). Each chart represents the mean +/−SD of 3 independent experiments.

Figure 7:
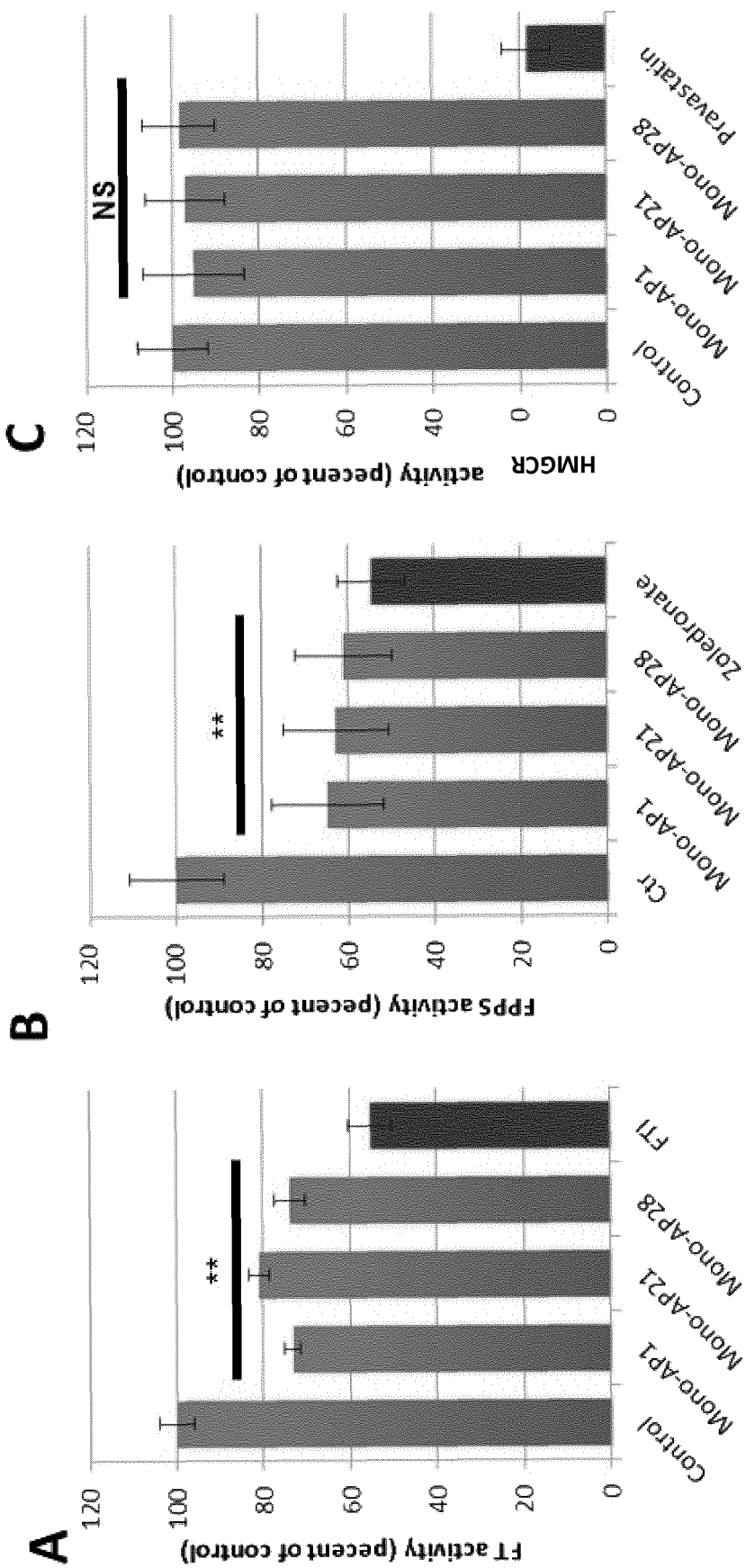

FIG. 7: Structure activity relationship study of Mono-APs (7A) Measure of FT activity in presence of Mono-AP1 25 μM, Monop-AP21 25 μM and Mono-AP28 25 μM. Tipifarnib 1 μM (FTI) was used as positive control. Results are presented in percent of control. Each point represents the mean +/−SD of the percentage of 8 replicates.

(7B) Measure of FPPS activity in presence of Mono-AP1 25 μM, Monop-AP21 25 μM and Mono-AP28 25 μM. Zoledronate 1 μM was used as positive control. Results are presented in percent of control. Each point represents the mean +/−SD of the percentage of 8 replicates.

(7C) Measure of GCR activity in presence of Mono-AP1 25 μM, Monop-AP21 25 μM and Mono-AP28 25 μM. Pravastatin 1 μM was used as positive control. Results are presented in percent of control. Each point represents the mean +/−SD of the percentage of 8 replicates.

DETAILED DESCRIPTION OF THE INVENTION

The present invention provides novel compounds that inhibit protein prenylation and which are thus useful for preventing or treating any disease or disorder requiring an inhibition of protein prenylation.

More precisely, it has been found according to the present invention that a class of aminopyrimidine compounds are inhibitors of protein prenylation, which compounds are specified in the present description.

As shown in the examples herein, these aminopyrimidine compounds efficiently inhibit protein prenylation, and more precisely protein farnesylation, while they are devoid of toxicity.

It is also shown herein that the inhibition of protein prenylation by these aminopyridine compounds is exerted by a specific targeting of prenylation enzymes, which encompasses farnesylation enzymes such as farnesyl pyrophosphate synthase (FPPS).

Using a cellular model of mesodermal stem cells obtained by reprogramming fibroblasts originating from individuals affected with progeria, it has been shown herein that these aminopyrimidine compounds are able to restore a normal phenotype, notably by inhibiting farnesylation of prelamin A.

It is shown herein that these novel aminopyrimidine compounds are able to rescue nuclear shape abnormalities encountered in progeria.

Also, it is shown herein that these novel aminopyrimidine compounds to rescue the disease-related phenotype of premature differentiation of mesodermal stem cells originating from individuals affected with progeria.

It is also shown herein that these aminopyrimidine compounds are devoid of toxicity, including devoid of cytotoxicity. Notably, these aminopyrimidine compounds have reduced or no effect on cell proliferation, nor on the cell energetic metabolism.

The present invention describes a compound or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, which is alternatively chosen among:

(1)

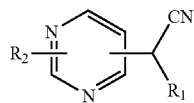
(I)

wherein $R_1$ is 2-pyridyl, 3-pyridyl or 4-pyridyl;

$R_2$ represents a group which is selected from the group consisting of:

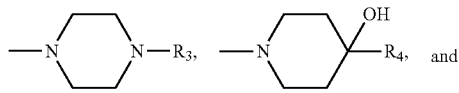

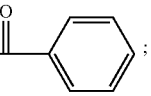

$R_3$ representing a group which is selected from the group consisting of:

an arylcarbonyl group, a heteroarylcarbonyl group, a $(C_1$-$C_4)$alkoxy-carbonylmethyl group, and a

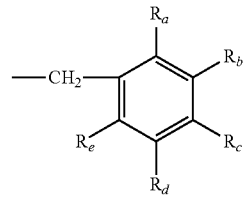

group, $R_a$, $R_b$, $R_c$, $R_d$ and $R_e$ being, independently a hydrogen atom, a halogen atom, a $(C_1$-$C_4)$alkyl group, or a $(C_1$-$C_4)$alkoxy group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms, and $R_4$ being a phenyl group substituted by a halogen atom, or a benzyl group; and (2)

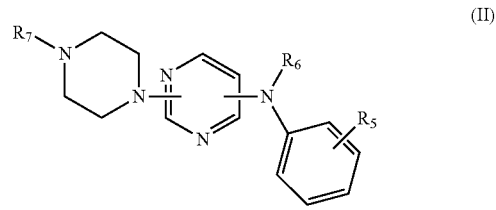
(II)

wherein $R_5$ represents a hydrogen atom or a $(C_{1-4})$alkyl group;

$R_6$ represents a hydrogen atom or a $(C_{1-4})$alkyl group; and $R_7$ represents a group which is selected from the group consisting of:

an arylcarbonyl group, a heteroarylcarbonyl group optionally substituted by one or two groups selected from a $(C_{1-4})$alkyl group and a phenyl group, a heteroarylacetyl group optionally substituted on the heteroaryl ring by a phenyl group, a $(C_1$-$C_4)$alkoxy-carbonylmethyl group, and a

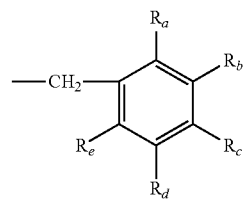

group, $R_a$, $R_b$, $R_c$, $R_d$ and $R_e$ being, independently a hydrogen atom, a halogen atom, a $(C_1$-$C_4)$alkyl group, or a $(C_1$-$C_4)$alkoxy group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms.

According to a first aspect, a subject-matter of the present invention relates to a compound or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, which is alternatively chosen among (1)

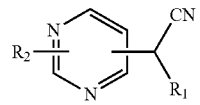

wherein
R₁ is 2-pyridyl, 3-pyridyl or 4-pyridyl;
R₂ represents a group which is selected from the group consisting of:

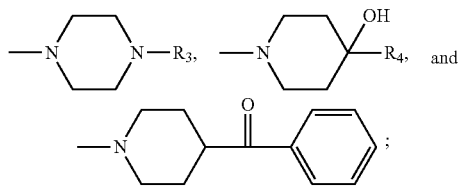

R₃ representing a group which is selected from the group consisting of:
an arylcarbonyl group,
a heteroarylcarbonyl group,
a $(C_1-C_4)$alkoxy-carbonylmethyl group, and
a

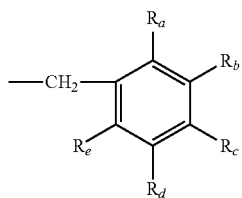

group, $R_a$, $R_b$, $R_c$, $R_d$ and $R_e$ being, independently a hydrogen atom, a halogen atom, a $(C_1-C_4)$alkyl group, or a $(C_1-C_4)$alkoxy group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms,
and R₄ being a phenyl group substituted by a halogen atom, or a benzyl group;
provided that
R₃ is not a 4-methylbenzyl group when R₁ is 2-pyridyl, and (2)

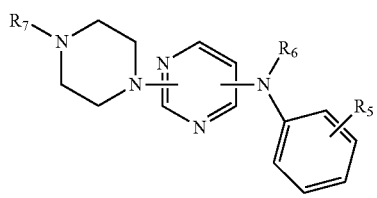

wherein
R₅ represents a hydrogen atom or a $(C_{1-4})$alkyl group;
R₆ represents a hydrogen atom or a $(C_{1-4})$alkyl group; and
R₇ represents a group which is selected from the group consisting of:
an arylcarbonyl group,
a heteroarylcarbonyl group optionally substituted by one or two groups selected from a $(C_{1-4})$alkyl group and a phenyl group,
a heteroarylacetyl group optionally substituted on the heteroaryl ring by a phenyl group,
a $(C_1-C_4)$alkoxy-carbonylmethyl group, and
a

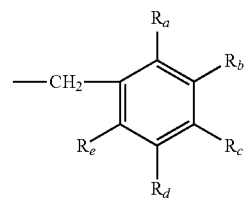

group, $R_a$, $R_b$, $R_c$, $R_d$ and $R_e$ being, independently a hydrogen atom, a halogen atom, a $(C_1-C_4)$alkyl group, or a $(C_1-C_4)$alkoxy group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms,
provided that
R₇ is not an indol-3-ylacetyl group when R₅ and R₆ are both a methyl group.

According to a preferred embodiment, a subject-matter of the present invention relates to a compound or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, which is alternatively chosen among (1)

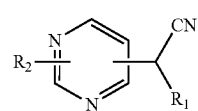

wherein
R₁ is 2-pyridyl, 3-pyridyl or 4-pyridyl;
R₂ represents a group which is selected from the group consisting of:

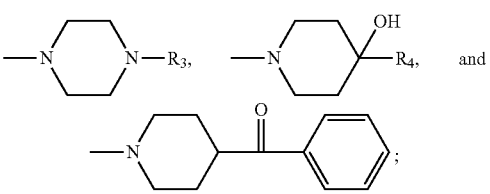

R₃ representing a group which is selected from the group consisting of:

a heteroarylcarbonyl group,
a $(C_1\text{-}C_4)$alkoxy-carbonylmethyl group, and
a

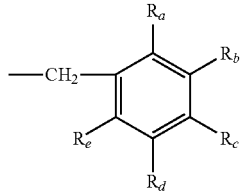

group, $R_a$, $R_b$, $R_c$, $R_d$ and $R_e$ being, independently a hydrogen atom, a halogen atom, or a $(C_1\text{-}C_4)$alkyl group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms,
and $R_4$ being a phenyl group substituted by a halogen atom, or a benzyl group;
provided that
$R_3$ is not a 4-methylbenzyl group when $R_1$ is 2-pyridyl, and (2)

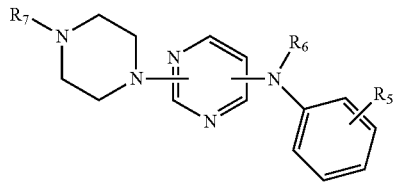

(II)

wherein
$R_5$ represents a hydrogen atom or a $(C_{1\text{-}4})$alkyl group;
$R_6$ represents a hydrogen atom or a $(C_{1\text{-}4})$alkyl group; and
$R_7$ represents a group which is selected from the group consisting of:
a heteroarylcarbonyl group optionally substituted by one or two groups selected from a $(C_{1\text{-}4})$alkyl group and a phenyl group, and
a heteroarylacetyl group optionally substituted on the heteroaryl ring by a phenyl group,
provided that
$R_7$ is not an indol-3-ylacetyl group when $R_5$ and $R_6$ are both a methyl group.

According to another aspect, a subject-matter of the present invention relates to a compound or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, which is alternatively chosen among (1)

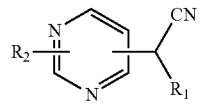

(I)

wherein
$R_1$ is 2-pyridyl, 3-pyridyl or 4-pyridyl;
$R_2$ represents a group which is selected from the group consisting of:

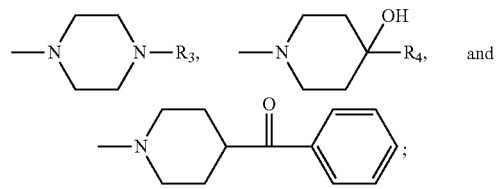

$R_3$ representing a group which is selected from the group consisting of:
an arylcarbonyl group,
a heteroarylcarbonyl group,
a $(C_1\text{-}C_4)$alkoxy-carbonylmethyl group, and
a

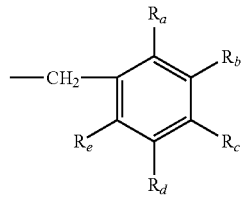

group, $R_a$, $R_b$, $R_c$, $R_d$ and $R_e$ being, independently a hydrogen atom, a halogen atom, a $(C_1\text{-}C_4)$alkyl group, or a $(C_1\text{-}C_4)$alkoxy group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms,
and $R_4$ being a phenyl group substituted by a halogen atom, or a benzyl group;
provided that
$R_3$ is not a 4-methylbenzyl group when $R_1$ is 2-pyridyl, and (2)

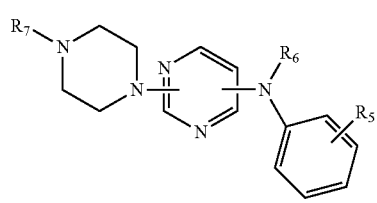

(II)

wherein
$R_5$ represents a hydrogen atom or a $(C_{1\text{-}4})$alkyl group;
$R_6$ represents a hydrogen atom or a $(C_{1\text{-}4})$alkyl group; and
$R_7$ represents a group which is selected from the group consisting of:
an arylcarbonyl group,
a heteroarylcarbonyl group optionally substituted by one or two groups selected from a $(C_{1\text{-}4})$alkyl group and a phenyl group,
a heteroarylacetyl group optionally substituted on the heteroaryl ring by a phenyl group,
a $(C_1\text{-}C_4)$alkoxy-carbonylmethyl group, and a

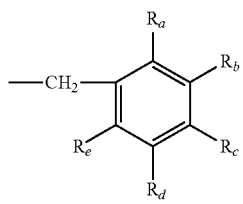

group, $R_a$, $R_b$, $R_c$, $R_d$ and $R_e$ being, independently a hydrogen atom, a halogen atom, a ($C_1$-$C_4$)alkyl group, or a ($C_1$-$C_4$)alkoxy group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms, provided that $R_7$ is not an indol-3-ylacetyl group when $R_5$ and $R_6$ are both a methyl group, $R_7$ is not a

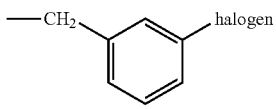

group when $R_5$ and $R_6$ are both a methyl group.

According to another preferred embodiment, a subject-matter of the present invention relates to a compound or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, which is alternatively chosen among (1)

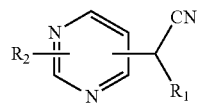                                     (I)

wherein $R_1$ is 2-pyridyl, 3-pyridyl or 4-pyridyl;

$R_2$ represents a group which is selected from the group consisting of:

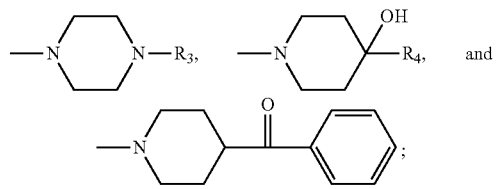

representing a group which is selected from the group consisting of:

a heteroarylcarbonyl group,
a ($C_1$-$C_4$)alkoxy-carbonylmethyl group, and
a

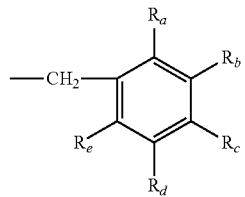

group, $R_a$, $R_b$, $R_c$, $R_d$ and $R_e$ being, independently a hydrogen atom, a halogen atom, or a ($C_1$-$C_4$)alkyl group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms, and $R_4$ being a phenyl group substituted by a halogen atom, or a benzyl group; provided that $R_1$ is not a 4-methylbenzyl group when $R_1$ is 2-pyridyl, and (2)

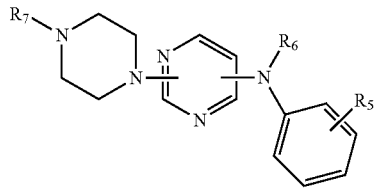                                    (II)

wherein $R_5$ represents a hydrogen atom or a ($C_{1-4}$)alkyl group;
$R_6$ represents a hydrogen atom or a ($C_{1-4}$)alkyl group; and
$R_7$ represents a group which is selected from the group consisting of:
  a heteroarylcarbonyl group optionally substituted by one or two groups selected from a ($C_{1-4}$)alkyl group and a phenyl group, and
  a heteroarylacetyl group optionally substituted on the heteroaryl ring by a phenyl group, provided that $R_7$ is not an indol-3-ylacetyl group when $R_5$ and $R_6$ are both a methyl group, $R_7$ is not a

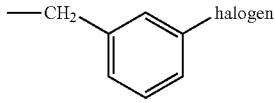

group when $R_5$ and $R_6$ are both a methyl group.

In another preferred embodiment, a subject-matter of the present invention relates to a compound or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, which is alternatively chosen among (1)

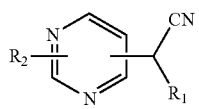

wherein
R₁ is 2-pyridyl, 3-pyridyl or 4-pyridyl;
R₂ represents a group which is selected from the group consisting of:

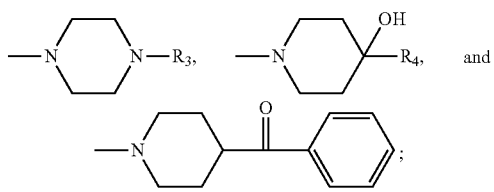

R₃ representing a group which is selected from the group consisting of:
an arylcarbonyl group,
a heteroarylcarbonyl group,
a C₁-C₄)alkoxy-carbonylmethyl group, and
a

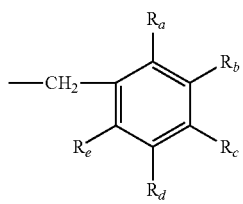

group, $R_a$, $R_b$, $R_d$ and $R_e$ being, independently a hydrogen atom, a halogen atom, a (C₁-C₄)alkyl group, or a (C₁-C₄)alkoxy group, and $R_c$ being a hydrogen atom, a halogen atom, or a (C₁-C₄)alkoxy group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms, and R₄ being a phenyl group substituted by a halogen atom, or a benzyl group; and (2)

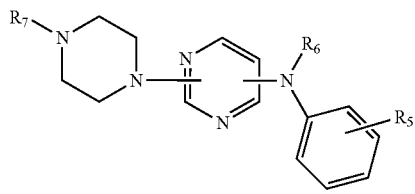

wherein
R₅ represents a hydrogen atom or a (C₁₋₄)alkyl group;
R₆ represents a hydrogen atom or a (C₁₋₄)alkyl group; and
R₇ represents a group which is selected from e group consisting of:

an arylcarbonyl group,
a heteroarylcarbonyl group optionally substituted by one or two groups selected from a (C₁₋₄)alkyl group and a phenyl group,
a heteroarylacetyl group substituted on the heteroaryl ring by a phenyl group,
a (C₁-C₄)alkoxy-carbonylmethyl group, and
a

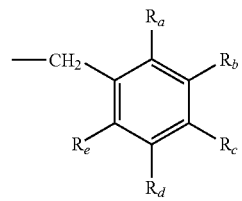

group, $R_a$, $R_b$, $R_c$, $R_d$, and $R_e$ being, independently a hydrogen atom, a halogen atom, a (C₁-C₄)alkyl group, or a (C₁-C₄)alkoxy group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms.

In a particular embodiment, a subject-matter of the present invention relates to a compound or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, which is alternatively chosen among (1)

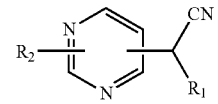

wherein
R₁ is 2-pyridyl, 3-pyridyl or 4-pyridyl;
R₂ represents a group which is selected from the group consisting of:

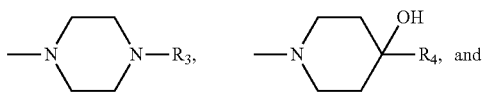

R₃ representing a group which is selected from the group consisting of:

a heteroarylcarbonyl group,
a (C$_1$-C$_4$)alkoxy-carbonylmethyl group, and
a

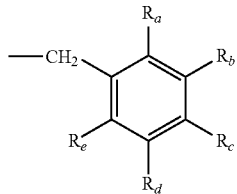

group, R$_a$, R$_b$, R$_d$ and R$_e$ being, independently a hydrogen atom, a halogen atom, or a (C$_1$-C$_4$)alkyl group, and R$_c$ being a hydrogen atom, or a halogen atom, R$_a$ and R$_b$, or R$_b$ and R$_c$, or R$_c$ and R$_d$, or R$_d$ and R$_e$ together optionally forming with the carbon atom to which they are attached a 5- or 6-membered ring fused to the phenyl ring comprising two oxygen atoms,
and R$_4$ being a phenyl group substituted by a halogen atom, or a benzyl group; and (2)

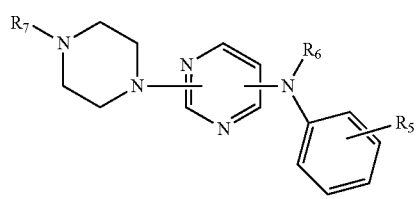

wherein
R$_5$ represents a hydrogen atom or a (C$_{1-4}$)alkyl group;
R$_6$ represents a hydrogen atom or a (C$_{1-4}$)alkyl group; and
R$_7$ represents a group which is selected from the group consisting of:
 a heteroarylcarbonyl group optionally substituted by one or two groups selected from a (C$_{1-4}$)alkyl group and a phenyl group, and
 a heteroarylacetyl group substituted on the heteroaryl ring by a phenyl group.

The compounds of the invention may exist in the form of free bases or of addition salts with pharmaceutically acceptable acids.

A "pharmaceutically acceptable salt" of a compound means a salt that is pharmaceutically acceptable and that possesses the desired pharmacological activity of the parent compound.

Suitable pharmaceutically acceptable acid addition salts of compounds according to the present invention include hydrochloride, hydrobromide, tartate, fumarate, citrate, trifluoroacetate, ascorbate, triflate, mesylate, tosylate, formate, acetate and malate.

The compounds of the present invention and salts thereof may form solvates (e.g. hydrates) and the invention includes all such solvates.

In the context of the present invention, the term:
"halogen" is understood to mean chlorine, fluorine, bromine, or iodine, and in particular denotes chlorine, fluorine or bromine and more preferably fluorine,
"(C$_1$-C$_4$)alkyl" as used herein respectively refers to C$_1$-C$_4$ normal, secondary or tertiary saturated hydrocarbon. Examples are, but are not limited to, methyl, ethyl, 1-propyl, 2-propyl, "(C$_1$-C$_4$)alkoxy" as used herein respectively refers to O—(C$_1$-C$_4$)alkyl moiety, wherein alkyl is as defined above. Examples are, but are not limited to, methoxy, ethoxy, 1-propoxy, 2-propoxy, "aryl" in the expression "arylcarbonyl group" is understood to mean a monovalent monocyclic or bicyclic aromatic hydrocarbon radical of 6 to 10 ring atoms. Examples are, but are not limited to, phenyl, naphthyl. More preferably "aryl" is phenyl, "heteroaryl" in the expressions "heteroarylcarbonyl group" and "heteroarylacetyl group" as used herein refers to a monovalent monocyclic or bicyclic aromatic radical of 5 to 10 ring atoms where one or more, preferably one, two, or three, ring atoms are heteroatom selected from N, O, or S, the remaining ring atoms being carbon. Representative examples include, but are not limited to, pyrrolyl, thienyl, thiazolyl, imidazolyl, furanyl, indolyl, isoindolyl, oxazolyl, isoxazolyl, benzothiazolyl, benzoxazolyl, quinolinyl, isoquinolinyl, pyridinyl, pyrimidinyl, pyrazinyl, pyridazinyl, triazolyl, tetrazolyl, and the like. Preferably, the heteroaryl is thienyl, furyl and more preferably is thienyl, and "patient" may extend to humans or mammals, such as cats or dogs.

In a particular aspect, the following group

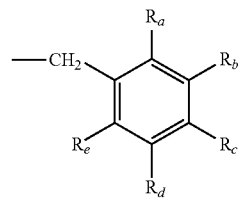

represents a group chosen from the following groups:

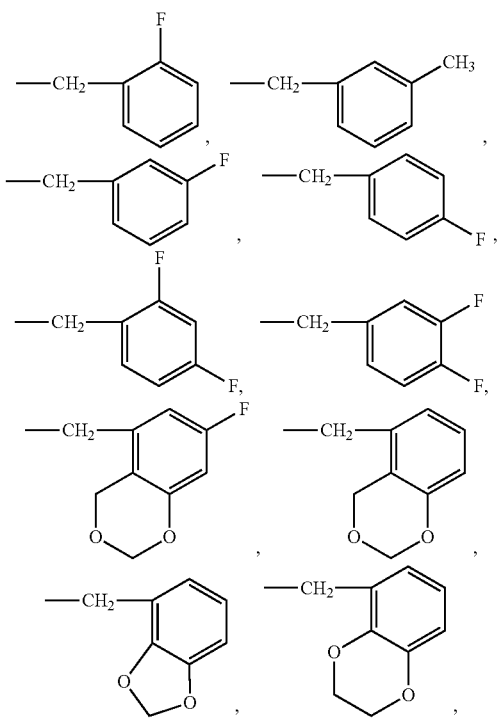

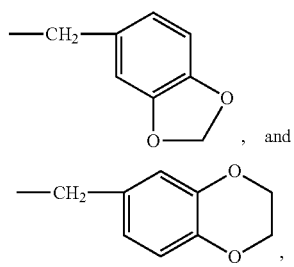, and

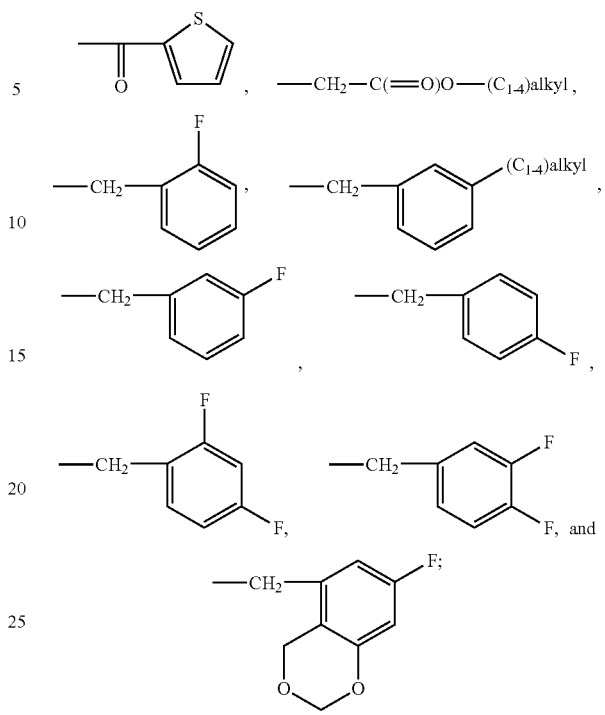

and more preferably a group chosen from the following groups:

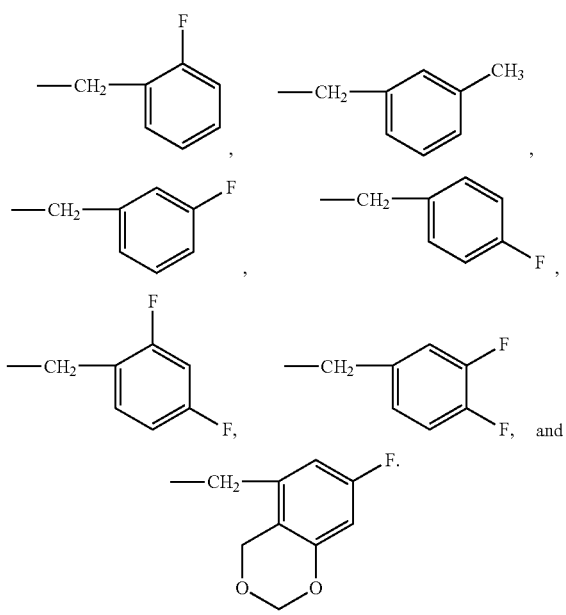

and $R_4$ being a phenyl group substituted by a halogen atom, or a benzyl group.

The present invention further relates to a compound of formula (Ia) as defined below or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required,

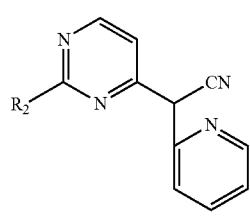

(Ia)

wherein $R_2$ represents a group which is selected from the group consisting of:

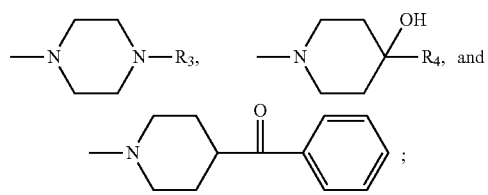

$R_3$ representing a group which is selected from the group consisting of:

In one particular variant, e present invention is directed to a compound of formula (I) as defined above or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, wherein $R_1$ is 2-pyridyl, 3-pyridyl or 4-pyridyl;

$R_2$ represents a group which is selected from the group consisting of:

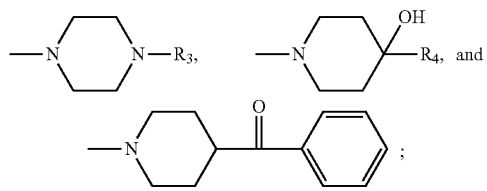

$R_3$ representing a group which is selected from the group consisting of:

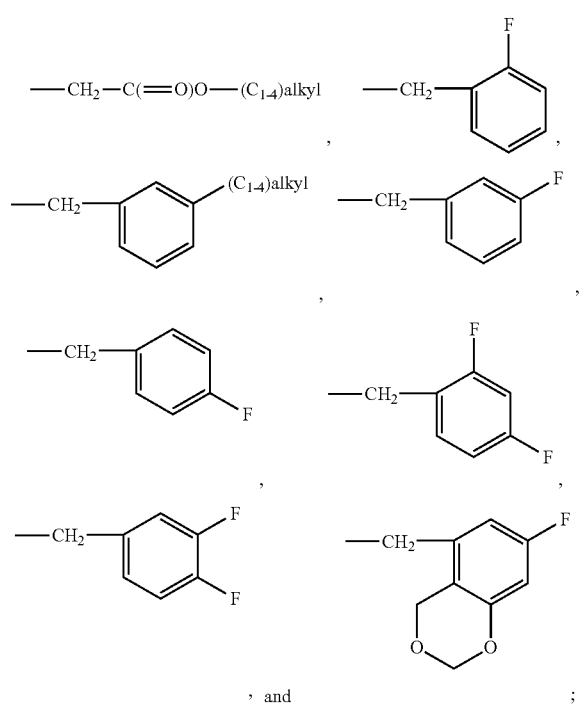

, and ;

and R$_4$ being a phenyl group substituted by a halogen atom.

The present invention further relates to a compound of formula (Ib) as defined below or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, (Ib)

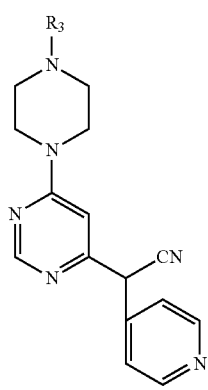

wherein R$_3$ represents a group which is selected from the group consisting of:

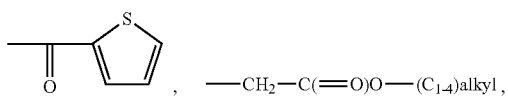

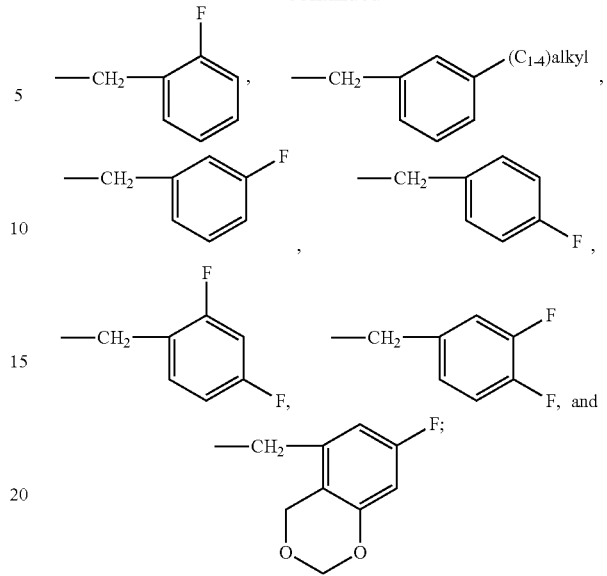

The present invention further relates to a compound of formula (Ic) as defined below or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, (Ic)

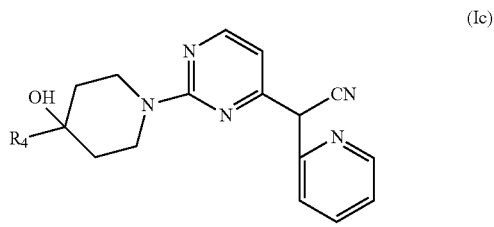

wherein R$_4$ a phenyl group substituted by a halogen atom, or a benzyl group.

The present invention further relates to a compound of formula (I'a) or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, (I'a)

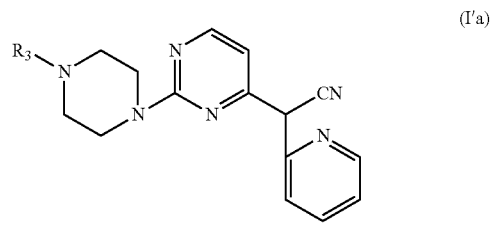

wherein R$_3$ represents a group which is selected from the group consisting of:

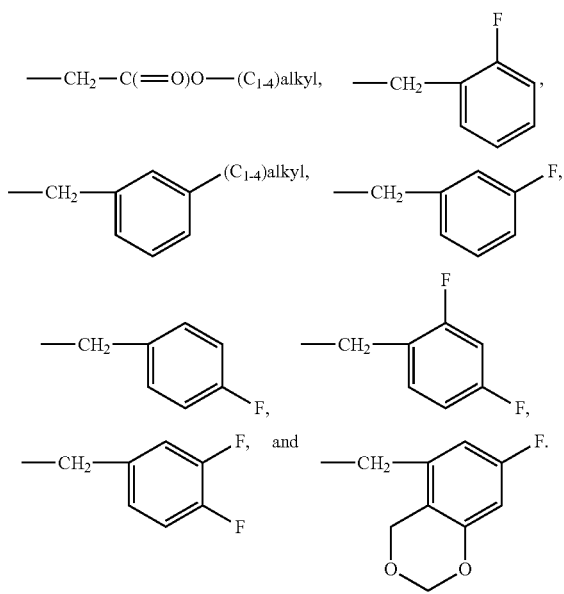

According to a preferred embodiment, the present invention relates to a compound of formula (I'a) as defined above or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, wherein $R_3$ represents a group which is selected from the group consisting of:

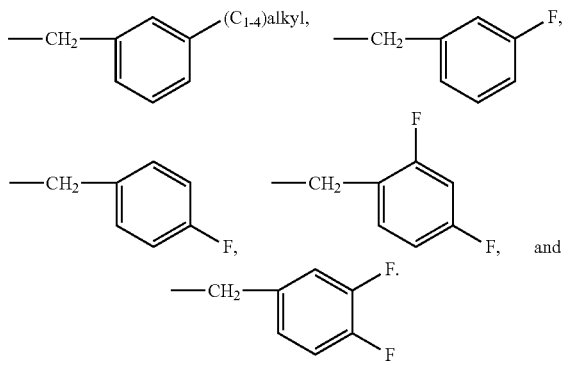

According to a more preferred embodiment, the present invention relates to a compound of formula (I'a) as defined above or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required, wherein $R_3$ represents a group which is selected from the group consisting of:

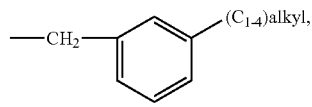

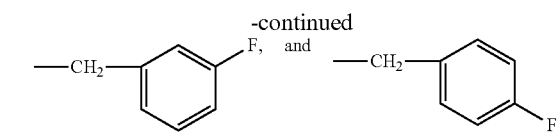

In another particular variant, the present invention is directed to a compound of formula (II) as defined above or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required,
wherein
$R_5$ represents a hydrogen atom or a $(C_{1-4})$alkyl group;
$R_6$ represents a hydrogen atom or a $(C_{1-4})$alkyl group; and
$R_7$ represents a group which is selected from the group consisting of:
  an arylcarbonyl group,
  a heteroarylcarbonyl group optionally substituted by one or two groups selected from a $(C_{1-4})$alkyl group and a phenyl group,
  a heteroarylacetyl group substituted on the heteroaryl ring by a phenyl group,
  a $(C_1-C_4)$alkoxy-carbonylmethyl group, and
  a

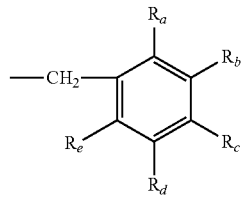

group, $R_a$, $R_c$, and $R_e$ being, independently a hydrogen atom, a halogen atom, a $(C_1-C_4)$alkyl group, or a $(C_1-C_4)$alkoxy group, $R_b$ and $R_d$ being independently a hydrogen atom or a $(C_1-C_4)$alkoxy group, $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms.

In another particular variant, the present invention is directed to a compound of formula (II) as defined above or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required,
wherein
$R_5$ represents a hydrogen atom or a $(C_{1-4})$alkyl group;
$R_6$ represents a hydrogen atom or a $(C_{1-4})$alkyl group; and
$R_7$ represents a group which is selected from the group consisting of:

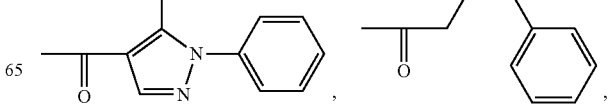

-continued

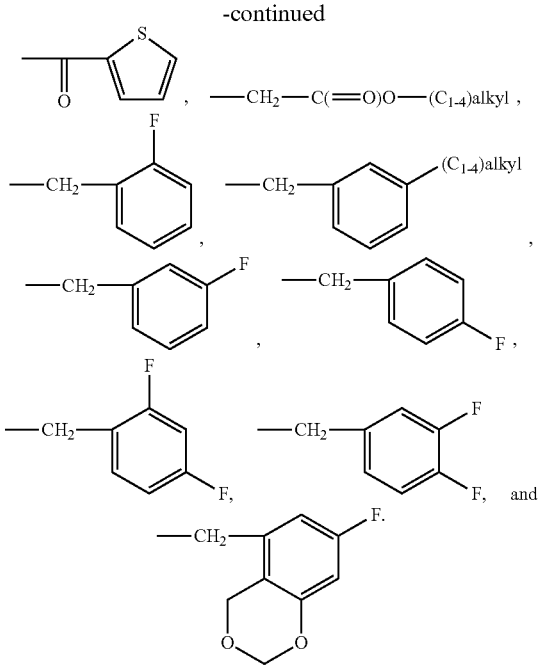

According to a preferred embodiment, the present invention relates to a compound of formula (II) as defined above or anyone of its pharmaceutically acceptable salts, under the form of enantiomers, diastereoisomers, and their mixtures, including the racemic mixture, for use in the treatment and/or prevention of diseases or disorders wherein an inhibition of protein prenylation is required,
wherein
$R_5$ represents a $(C_{1-4})$alkyl group and preferably a methyl group;
$R_6$ represents a $(C_{1-4})$alkyl group and preferably a methyl group; and
$R_7$ represents the following group:

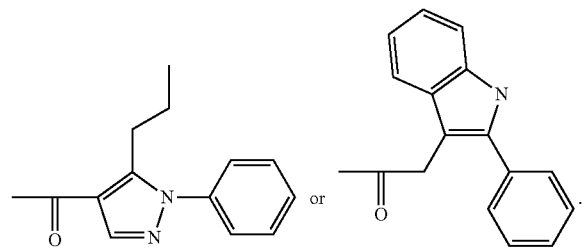

According to a preferred embodiment of the present invention, the compound for use in the treatment and/or prevention of diseases or disorders wherein an inhibition of protein prenylation is required, is chosen among:
(1) {2-[4-(2-fluoro-benzyl)-piperazin-1-yl]-pyrimidin-4-yl}-pyridin-2-yl-acetonitrile, i.e. Mono-AP1
(2) {2-[4-(4-Chloro-phenyl)-4-hydroxy-piperidin-1-yl]-pyrimidin-4-yl}-pyridin-2-yl-acetonitrile, i.e. Mono-AP9
(3) [2-(4-Benzoyl-piperidin-1-yl)-pyrimidin-4-yl]-pyridin-2-yl-acetonitrile, i.e. Mono-AP16
(4) {2-[4-(3-Methyl-benzyl)-piperazin-1-yl]-pyrimidin-4-yl}-pyridin-2-yl-acetonitrile, i.e. Mono-AP21
(5) {2-[4-(4-Fluoro-benzyl)-piperazin-1-yl]-pyrimidin-4-yl}-pyridin-2-yl-acetonitrile, i.e. Mono-AP24
(6) {4-[4-(Cyano-pyridin-2-yl-methyl)-pyrimidin-2-yl]-piperazin-1-yl}-acetic acid ethyl ester, i.e. Mono-AP25
(7) {2-[4-(2,4-Difluoro-benzyl)-piperazin-1-yl]-pyrimidin-4-yl}-pyridin-2-yl-acetonitrile, i.e. Mono-AP26
(8) {2-[4-(6-Fluoro-4H-benzo[1,3]dioxin-8-ylmethyl)-piperazin-1-yl]-pyrimidin-4-yl}-pyridin-2-yl-acetonitrile, i.e. Mono-AP27
(9) {2-[4-(3-Fluoro-benzyl)-piperazin-1-yl]-pyrimidin-4-yl}-pyridin-2-yl-acetonitrile, i.e. Mono-AP28
(10) {2-[4-(3,4-Difluoro-benzyl)-piperazin-1-yl]-pyrimidin-4-yl}-pyridin-2-yl-acetonitrile, i.e. Mono-AP30
(11) Pyridin-4-yl-{6-[4-(thiophene-2-carbonyl)-piperazin-1-yl]-pyrimidin-4-yl}-acetonitrile, i.e. Mono-AP2
(12) [2-(4-Benzyl-4-hydroxy-piperidin-1-yl)-pyrimidin-4-yl]-pyridin-2-yl-acetonitrile, i.e. Mono-AP3
(13) {4-[6-(Methyl-m-tolyl-amino)-pyrimidin-4-yl]-piperazin-1-yl}-(1-phenyl-5-propyl-1H-pyrazol-4-yl)-methanone, i.e. Di-AP2, and
(14) 1-{4-[6-(Methyl-m-tolyl-amino)-pyrimidin-4-yl]-piperazin-1-yl}-2-(2-phenyl-1H-indol-3-yl)-ethanone, i.e. Di-AP1,
and their pharmaceutically acceptable salts, under the form of enantiomers, diastereoisomers, and their mixtures, including the racemic mixture.

The present invention also relates to a compound of formulae (I), (II), (Ia), (Ib), (Ic) and (I'a) as defined above, as such.

Thus, said compounds (1), (2), (3), (4), (5), (6), (7), (8), (9), (10), (11), (12), (13) and (14) are new and form part of the present invention, as well as any one of their pharmaceutically acceptable salts such as hydrochloride, hydrobromide, tartrate, fumarate, citrate, trifluoroacetate, ascorbate, triflate, mesylate, tosylate, formate, acetate and malate.

The present invention therefore extends to compounds (1), (2), (3), (4), (5), (6), (7), (8), (9), (10), (11), (12), (13) and (14) and their pharmaceutically acceptable salts, as such.

A compound of formulae (I), (II), (Ia), (Ib), (Ic), and (I'a) can comprise one or more asymmetric carbon atoms. They can thus exist, as mentioned above, in the form of enantiomers or of diastereoisomers. These enantiomers, diastereoisomers and their mixtures, including the racemic mixtures, are encompassed within the scope of the present invention.

According to another aspect, the present invention relates to compounds of formulae (I), (II), (Ia), (Ib), (Ic) and (I'a) and the specific compounds (1), (2), (3), (4), (5), (6), (7), (8), (9), (10), (11), (12), (13) and (14) and their pharmaceutically acceptable salts for use as medicines.

The new compounds of the present invention, i.e. compounds of formulae (I), (II), (Ia), (Ib), (Ic) and (I'a) and the specific compounds as listed above are thus useful as medicines and more particularly can be used to treat and/or prevent diseases or disorders wherein an inhibition of protein prenylation is required. Said diseases or disorders may include Hutchinson-Gilford progeria syndrome (HGPS), progeria, a neurodegenerative disease, Parkinson's Disease, diffuse Lewy body disease, multiple system atrophy, Shy-Drager syndrome, striatonigral degeneration, olivopontocerebellar atrophy, pantothenate kinase-associated neurodegeneration, cognitive impairment, dementia, a lysosomal storage disease, glycogen storage disease type II, mucopolysaccharidoses, mucolipidosis II, mucolipidosis III, mucosulfatidosis, GM2 activator protein deficiency variant AB, Danon disease, Salla disease, Tay-Sachs disease, Sandhoff disease, Schindler disease, Kanzaki disease, alpha-mannosidosis, beta-mannosidosis, fucosidosis, sialidosis, aspartylglucosaminuria, carbohydrate-deficient glycoprotein syndrome, Wolman disease, Farber disease, Niemann-Pick disease types A, B, and C, Gaucher disease, Krabbe disease, Fabry disease, multiple sulfatase deficiency, GM1 gangliosidosis, GM2 gangliosidosis, GM3 gangliosidosis, galactosialidosis, cystinosis, sialic acid storage disease, pyknodysostosis, metachromatic leukodystrophy, galactosialidosis, neuronal ceroid lipofuscinosis, lactosylceramidosis, Pompe disease, cobalamin definiciency type F, amyotrophic lateral sclerosis, Huntington's Disease, Alzheimer's Disease; a mitochondrial disease, an ocular disease, an inflammatory disease, a cardiovascular disease, a proliferative disease, depression, anxiety, an immune disease, a neoplastic disease, a tumor, a cancer, a metastase, a leukemia, a carcinoma, a melanoma, a sarcoma, a glioblastoma, a multiple myeloma, an adenoma, a neoplasia, a neuroblastoma, an adenocarcinoma, a lymphoma, a myeloma, a multiple myeloma, a myelo-dysplastic syndrome, acute myeloid leukemia, chronic myeloid leukemia, chronic myelomonocytic leukemia, angiogenic myeloid metaplasia, a mesothelioma, a glioma, atherosclerosis, bilestones, cholelithiasis, lipocalcinogranulomatosis, hypercholesterolemia, hyperlipoproteinaemia, cholesterol crystal embolism, myocardial infection, cerebral infarction, angina pectoris, osteoporosis, arthritis, rheumatoid arthritis, osteoarthritis, Paget's Disease, Neurofibromatosis Type 1, Leopard Syndrome, Noonan Syndrome, Legius Syndrome, Costello Syndrome, hereditary gingival fibromatosis type 1, autoimmune lymphoproliferative syndrome, capillary malformation-arteriovenous malformation, skin aging, hormonal aging, photo-induced premature skin aging, aging myo-lipo-skin, restrictive dermopathy, alteration or loss of hair, alopecia, Hepatitis delta virus infection, and viral infection.

More particularly, the tumors and cancers are selected from bone, brain, kidney, liver, adrenal gland, colorectal, urinary bladder, breast, stomach, ovaries, colon, rectum, prostate, pancreas, lung, non-small cell lung, small cell lung, vagina, thyroid, the neck and head cancers and tumors.

The compounds of the present invention can be prepared by conventional methods of organic synthesis practiced by those skilled in the art. The general reaction sequences outlined below represent a general method useful for preparing the compounds of the present invention and are not meant to be limiting in scope or utility.

As explained and illustrated below in the schemes 1, 2 and 3, three routes, respectively Route A, Route B and Route C are available for recovering a compound according to the present invention.

Scheme 1: Route A

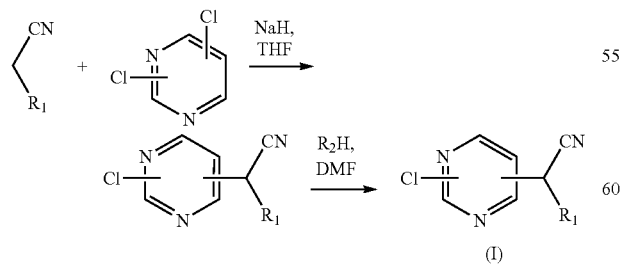

To a suspension of 1.1 equivalent of sodium hydride 0.1 M in tetrahydrofuran (T) was added dropwise a solution of one equivalent of a 2-pyridylacetonitrile, 3-pyridylacetonitrile or 4-pyridylacetonitrile, and preferably a 2-pyridylacetonitrile 0.1 M in THF. The mixture is stirred for 30 minutes and then cooled to 0° C. by an ice bath. A solution of one equivalent of a dichloropyrimidine such as 2,4-dichloropyrimidine, 1 M in dimethylformide (DMF) was added dropwise and the reaction mixture is stirred overnight at room temperature. The reaction mixture is partially evaporated, diluted with water and returned to pH 7 with concentrated HCl. The solution is extracted with ethyl acetate, the organic phase is dried and evaporated to give an orange solid (halogenated intermediate) which was used without further purification.

The halogenated intermediate is dissolved in 0.1 M in DMF in the presence of one equivalent of the appropriate secondary amine $R_2H$ and one equivalent of diisopropylethylamine (DIEA) and the reaction mixture is heated at 130° C. for 1 hour. The reaction medium is evaporated and the product purified by chromatography on a $C_{18}$ semi-automatic device in a water/methanol gradient.

The Route A is particularly suitable for compounds of formula (I) wherein $R_1$, $R_2$ and $R_4$ are as defined above in formula (I), $R_3$ representing a $(C_1-C_4)$alkoxy-carbonylmethyl group or a

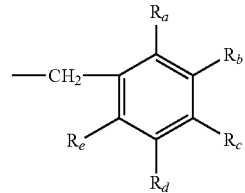

group, $R_a$, $R_b$, $R_c$, $R_d$ and $R_e$ being as defined above in formula (I).

More particularly, compounds (1), (2), (3), (4), (5), (6), (7), (8), (9), (10), and (12) can be prepared via Route A, as shown below more in detail in the experimental part.

Scheme 2: Route B

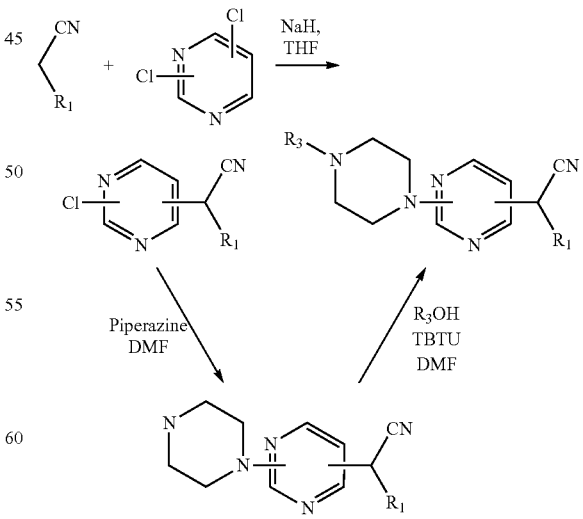

etonitrile, and preferably a 4-pyridylacetonitrile to 0.1 M in THF. The mixture is stirred for 30 minutes and then cooled to 0° C. by an ice bath. A solution of one equivalent of 4,6-dichloropyrimidine 1M in DMF was added dropwise and the reaction mixture is stirred overnight at room temperature. The reaction mixture is partially evaporated, diluted with water and returned to pH 7 with concentrated HCl. The solution is extracted with ethyl acetate, the organic phase is dried and evaporated to give an orange solid which was used without further purification.

The halogenated intermediate is dissolved in 0.1 M in DMF in the presence of 5 equivalents of piperazine and one equivalent of DIEA and the reaction mixture is heated at 130° C. for 1 hour. The reaction medium is evaporated and the product purified by chromatography on a $C_{18}$ semi-automatic device in a water/methanol gradient.

The acid is dissolved at 0.2 M in DMF in the presence of two equivalents of DIEA. One equivalent of a 0.2 M solution of O-(benzotriazol-1-yl)-N, N, N', N'-tetramethyluronium tetrafluoroborate (TBTU) was added and the reaction mixture is stirred 5 minutes. An amine equivalent of 0.2 M in DMF was added and the reaction medium is stirred for 1 hour and then evaporated. The residue was redissolved in ethyl acetate and washed with 1 M $Na_2CO_3$ and then with water. The organic phase is evaporated and the product was purified on $C_{18}$ in a water/methanol gradient.

The Route B is particularly suitable for compounds of formula (I) wherein $R_1$ is as defined above in formula (I), $R_2$ is

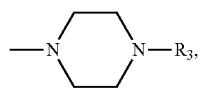

$R_3$ representing an arylcarbonyl group such as a benzoyl group or a heteroarylcarbonyl group such as a thienylcarbonyl group.

More particularly, compound (11) can be prepared via Route B, as shown below more in detail in the experimental part.

Scheme 3: Route C

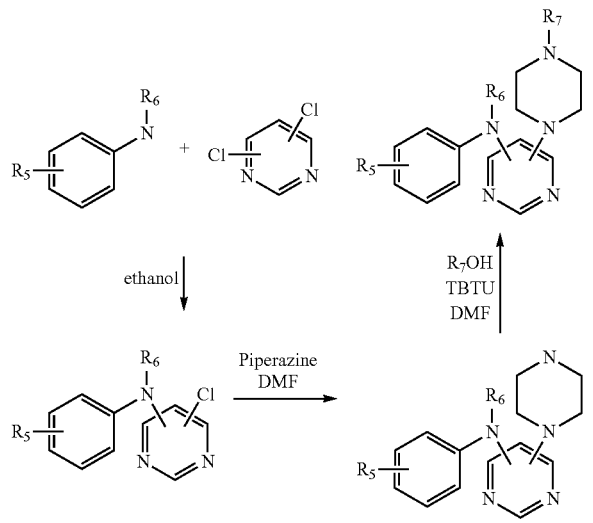

To a solution of one equivalent of dichloropyrimidine such as 4,6-dichloropyrimidine in 0.1 M in ethanol was added a solution of one equivalent of $R_5$-phenyl-N—$R_6$ such as N-methyl-m-toluidine 0.1 M in ethanol. The medium is refluxed for 4 hours and is then partially evaporated and diluted with water. The solution is extracted with ethyl acetate, the organic phase is dried and evaporated to give a solid which was used without further purification.

The halogenated intermediate is dissolved in 0.1 M in D in the presence of 5 equivalents of piperazine and one equivalent of DIEA and the reaction mixture is heated at 130° C. for 1 hour. The reaction medium is evaporated and the product purified by chromatography on a $C_{18}$ semi-automatic device in a water/methanol gradient.

The acid is dissolved at 0.2 M in DMF in the presence of two equivalents of DIEA. One equivalent of a 0.2 M solution of TBTU was added and the reaction mixture is stirred 5 minutes. An amine equivalent of 0.2 M in DMF was added and the reaction medium is stirred for 1 hour and then evaporated. The residue was redissolved in ethyl acetate and washed with 1 M $Na_2CO_3$ and then with water. The organic phase is evaporated and the product was purified on $C_{18}$ in a water/methanol gradient.

The Route C is particularly suitable for compounds of formula (II) wherein $R_5$ and $R_6$ are as defined above in formula (II), and $R_7$ is an arylcarbonyl group, a heteroarylcarbonyl group optionally substituted by one or two groups selected from a $(C_1$-$C_4)$alkyl group and a phenyl group and a heteroarylacetyl group optionally substituted on the heteroaryl ring by a phenyl group.

More particularly, compounds (13) and (14) can be prepared via Route C, as shown below more in detail in the experimental part.

The chemical structures and data of some compounds according to the invention are illustrated respectively in the following Table I and Table II.

The characterization of each compound (1) to (14) according to the invention has been carried out via liquid chromatography—mass spectrometry (LC/MS).

The analytical conditions are as follows:

Device: Waters 2795 HPLC coupled to a mass spectrometer Micromass/Waters Platform LC Column: Varian Pursuit $C_{18}$ (2.0×20.0 microns)

Flow rate: 0.8 mL/min

Analysis time: 5 min

Detection: Waters 996 Diode Array (180-500 nm

Mobile phases: 10 mM ammonium formate in water/methanol (9/1 by volume) at pH 8 (A) and 10 mM ammonium formate in methanol (B).

Elution:

| Time (min) | A (%, v/v) | B (%, v/v) |
| --- | --- | --- |
| 0 | 100 | 0 |
| 0.2 | 100 | 0 |
| 2.7 | 0 | 100 |
| 4.4 | 0 | 100 |
| 5 | 100 | 0 |

Mass spectra were obtained with an electrospray ionization source (ES <+>).

Furthermore, purity, molecular weight and retention time data for each compound (1) to (14) according to the invention are included in Table II.

TABLE I
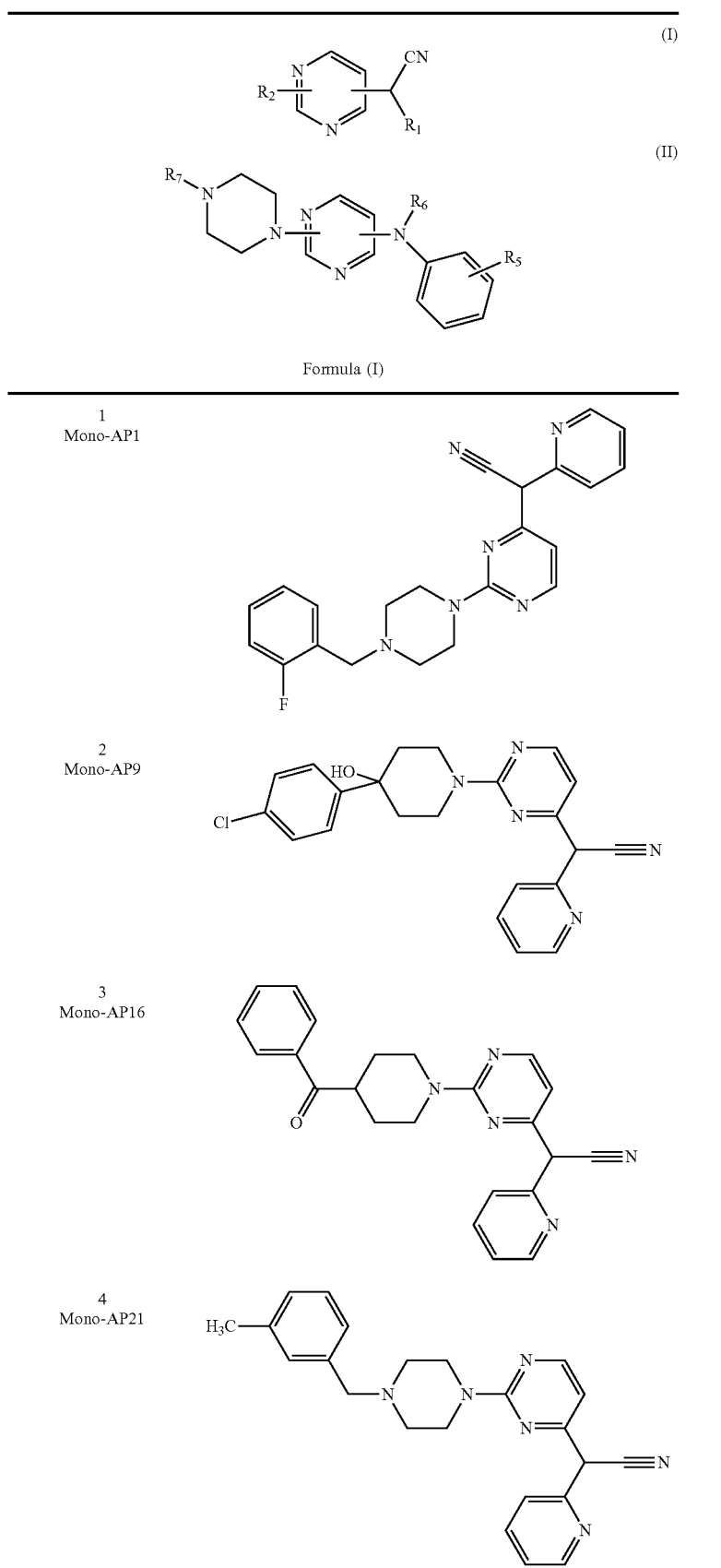
Formula (I)
1 Mono-AP1
2 Mono-AP9
3 Mono-AP16
4 Mono-AP21

TABLE I-continued
| 5 Mono-AP24 | 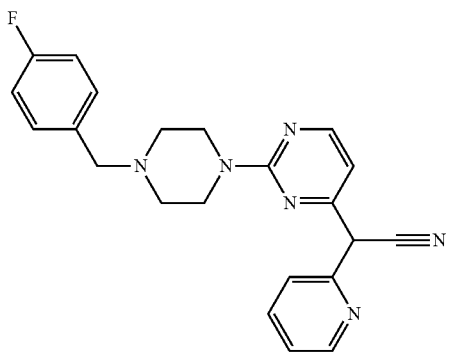 [SMILES: N#CC(c1ccccn1)c1ccnc(N2CCN(Cc3ccc(F)cc3)CC2)n1] |
| 6 Mono-AP25 | 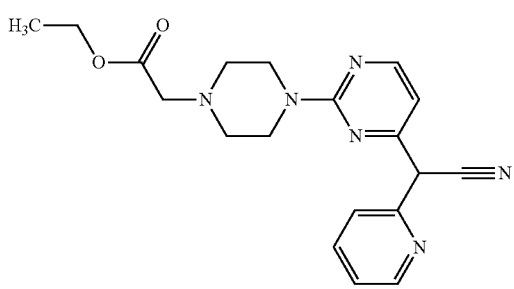 [SMILES: CCOC(=O)CN1CCN(c2nccc(C(C#N)c3ccccn3)n2)CC1] |
| 7 Mono-AP26 | 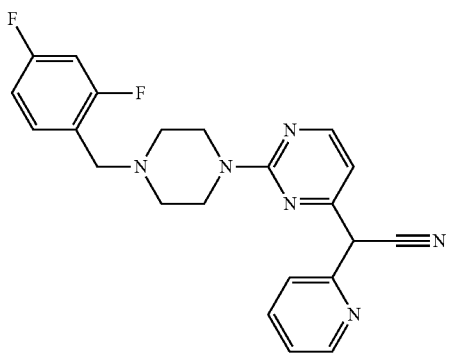 [SMILES: N#CC(c1ccccn1)c1ccnc(N2CCN(Cc3ccc(F)cc3F)CC2)n1] |
| 8 Mono-AP27 | 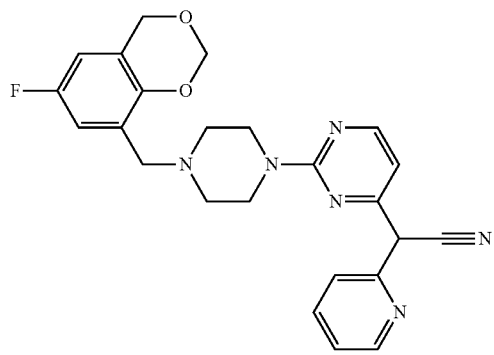 [SMILES: N#CC(c1ccccn1)c1ccnc(N2CCN(Cc3cc(F)cc4c3OCOC4)CC2)n1] |

TABLE I-continued
| | | |
|---|---|---|
| 9<br>Mono-AP28 | 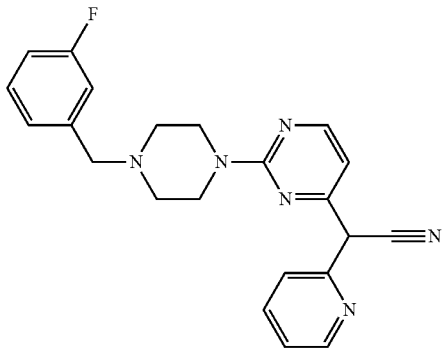 [SMILES: N#CC(c1ccccn1)c1ccnc(N2CCN(Cc3cccc(F)c3)CC2)n1] | |
| 10<br>Mono-AP30 | 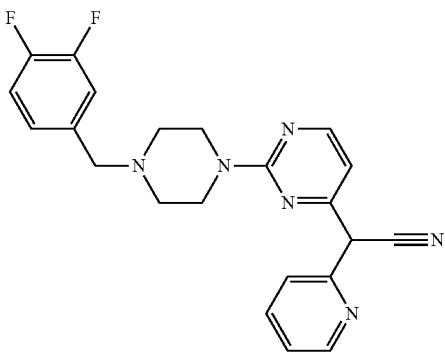 [SMILES: N#CC(c1ccccn1)c1ccnc(N2CCN(Cc3ccc(F)c(F)c3)CC2)n1] | |
| 11<br>Mono-AP2 | 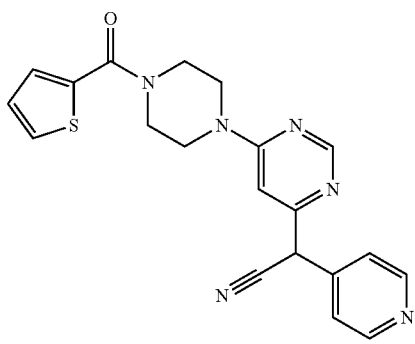 [SMILES: N#CC(c1ccncc1)c1cc(N2CCN(C(=O)c3cccs3)CC2)ncn1] | |
| 12<br>Mono-AP3 | 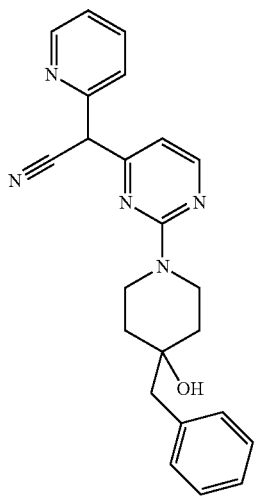 [SMILES: N#CC(c1ccccn1)c1ccnc(N2CCC(O)(Cc3ccccc3)CC2)n1] | |

TABLE I-continued

Formula (II)

13
Di-AP2

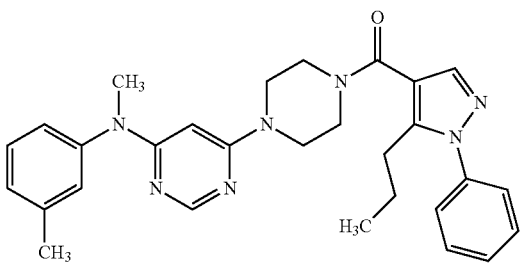 [SMILES: CCCc1c(C(=O)N2CCN(c3cc(N(C)c4cccc(C)c4)ncn3)CC2)cnn1-c1ccccc1]

14
Di-AP1

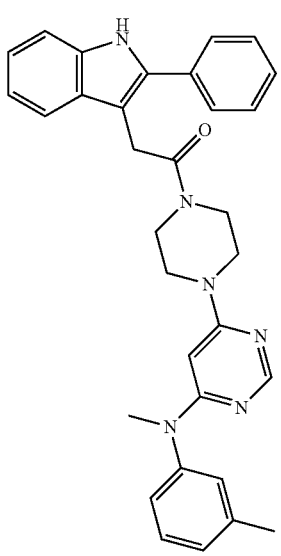 [SMILES: Cc1cccc(N(C)c2cc(N3CCN(C(=O)Cc4c(-c5ccccc5)[nH]c5ccccc45)CC3)ncn2)c1]

TABLE II

| Ex | Purity (%) | Molecular weight (MW) (g/mol) | Retention Time (RT) (min) | M + 1 (ES <+>) |
|---|---|---|---|---|
| 1 | 94 | 388.4409832 | 2.79 | 389 |
| 2 | 93 | 405.88 | 2.82 | 406 |
| 3 | 92 | 383.44594 | 2.67 | 384 |
| 4 | 100 | 384.4771 | 2.99 | 385 |
| 5 | 97 | 388.4409832 | 2.79 | 389 |
| 6 | 87 | 366.41722 | 2.47 | 367 |
| 7 | 96 | 406.4314464 | 2.82 | 407 |
| 8 | 92 | 446.4770632 | 2.77 | 447 |
| 9 | 100 | 388.4409832 | 2.84 | 389 |
| 10 | 94 | 406.4314464 | 2.84 | 407 |
| 11 | 84 | 390.46276 | 2.46 | 391 |
| 12 | 98 | 385.46182 | 2.83 | 386 |
| 13 | 94 | 495.6189 | 2.83 | 496 |
| 14 | 100 | 516.63632 | 2.84 | 517 |

Characterizations above header.

Methods of administration of the aminopyridine compounds specified therein as well as pharmaceutical compositions containing the same are described elsewhere in the present specification.

The following examples illustrate in detail the preparation of compounds (1) to (14) according to the present invention. The structures of the product obtained have been confirmed at least by LC-MS.

EXAMPLES

Example I: Preparation of Compounds According to the Present Invention

As mentioned above:

compounds (1), (2), (3), (4), (5), (6), (7), (8), (9), (10), and (12) according to the present invention can be prepared via Route A;

compound (11) according to the present invention can be prepared via Route B; and compounds (13 and 14) according to the present invention can be prepared via Route C.

Example I-1: Mono-APL Compound (1) of Table I

Step 1

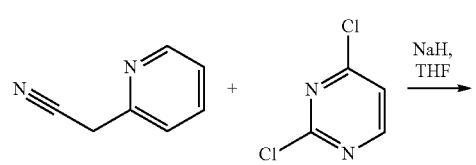

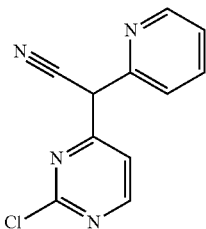

To a suspension of 1.1 equivalent of sodium hydride 0.1M in tetrahydrofuran (THF) was added dropwise a solution of one equivalent of 2-pyridylacetonitrile 0.1 M in THF. The mixture is stirred for 30 minutes and then cooled to 0° C. by an ice bath. A solution of one equivalent of 2,4-dichloropyrimidine 1 M in dimethylformamide (DMF) was added dropwise and the reaction mixture is stirred overnight at room temperature. The reaction mixture is partially evaporated, diluted with water and returned to pH 7 with concentrated HCl. The solution is extracted with ethyl acetate, the organic phase is dried and evaporated to give an orange solid (halogenated intermediate) which was used without further purification. The halogenated intermediate is obtained with a yield of 55%.

Step 2

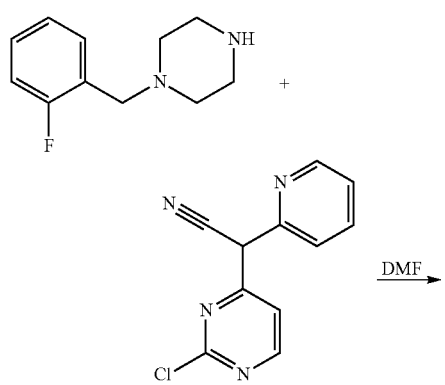

The halogenated intermediate is dissolved in 0.1 M in D in presence of one equivalent of 1-(2-fluoro-benzyl) piperazine and one equivalent of DIEA and the reaction mixture is heated to 130° C. for 1 hour. The reaction medium is evaporated and the product purified by chromatography on a $C_{18}$ semi-automatic device in a water/methanol gradient. Compound (1) is obtained with a yield of 82%.

Example I-2: Mono-AP9, Compound (21 of Table I

Firstly, Step 1 as described in Example I-1 above is carried out.

Step 2

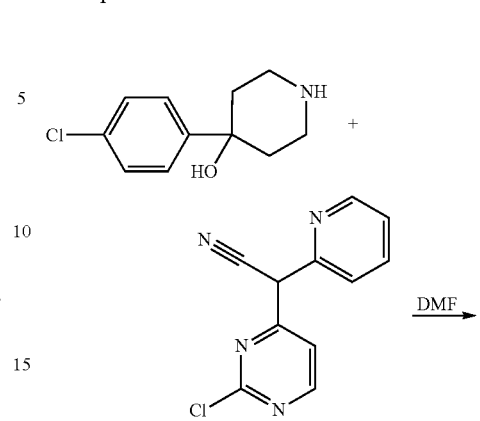

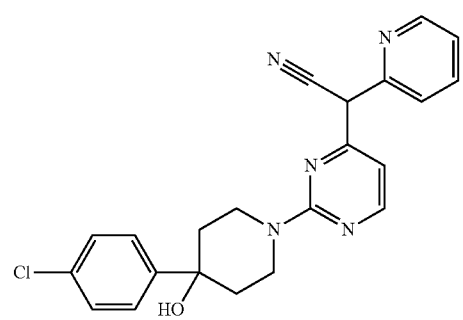

The halogenated intermediate is dissolved in 0.1 M in DMF in the presence of one equivalent of 4-(4-chlorophenyl) piperidin-4-ol and an equivalent of DIEA and the reaction mixture is heated at 130° C. for 1 hour. The reaction medium is evaporated and the product purified by chromatography on a C18 semi-automatic device in a water/methanol gradient. Compound (2) is obtained with a yield of 80%.

Example I-3: Mono-AP16, Compound (3) of Table I

Firstly, Step 1 as described in Example I-1 above is carried out.

Step 2

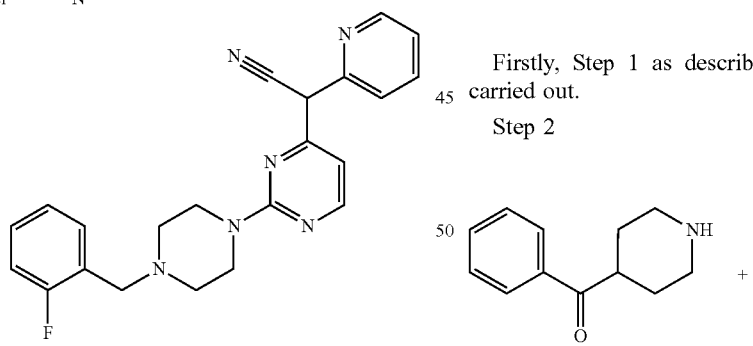

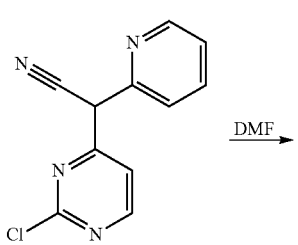

-continued

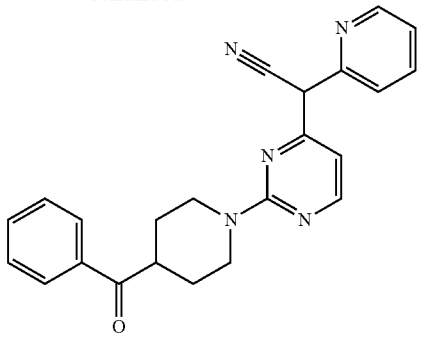

The halogenated intermediate is dissolved in 0.1 M in D in the presence of one equivalent of phenyl-piperidin-4-yl-methanone hydrochloride and an equivalent of DIEA and the reaction mixture is heated at 130° C. for 1 hour. The reaction medium is evaporated and the product purified by chromatography on a C18 semi-automatic device in a water/methanol gradient. Compound (3) is obtained with a yield of 75%.

Example I-4: Mono-AP21, Compound (4) of Table I

Firstly, Step 1 as described in Example I-1 above is carried out.
Step 2

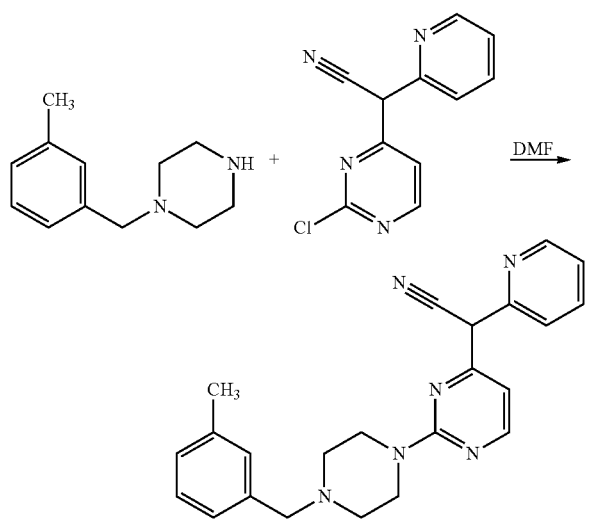

The halogenated intermediate is dissolved in 0.1 M in D in presence of one equivalent of 1-(3-methyl-benzyl) piperazine and one equivalent of DIEA and the reaction mixture is heated to 130° C. for 1 hour. The reaction medium is evaporated and the product purified by chromatography on a C18 semi-automatic device in a water/methanol gradient. Compound (4) is obtained with a yield of 84%.

Example I-5: Mono-AP24, Compound (5) of Table I

Firstly, Step 1 as described in Example I-1 above is carried out.

Step 2

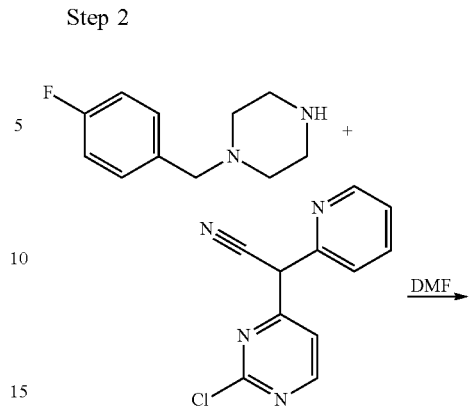

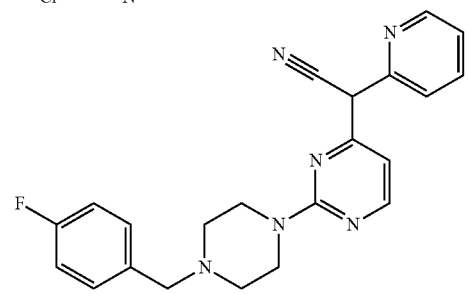

The halogenated intermediate is dissolved in 0.1 M in D in presence of one equivalent of 1-(4-fluoro-benzyl) piperazine and one equivalent of DIEA and the reaction mixture is heated to 130° C. for 1 hour. The reaction medium is evaporated and the product purified by chromatography on a C18 semi-automatic device in a water/methanol gradient. Compound (5) is obtained with a yield of 76%.

Example I-6: Mono-AP25, Compound (6) of Table I

Firstly, Step 1 as described in Example I-1 above is carried out.
Step 2

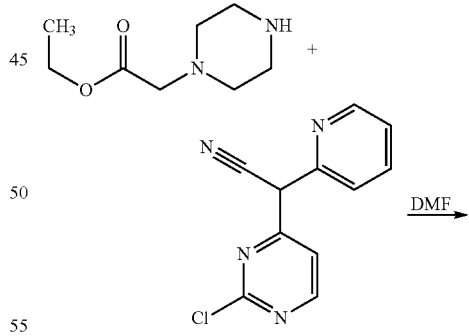

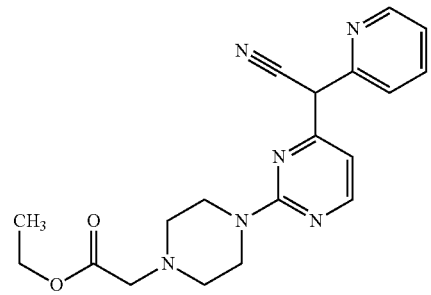

The halogenated intermediate is dissolved in 0.1 M in DMF in presence of one equivalent of 1-(3-methyl-benzyl) piperazine and one equivalent of DIEA and the reaction mixture is heated to 130° C. for 1 hour. The reaction medium is evaporated and the product purified by chromatography on a C18 semi-automatic device in a water/methanol gradient. Compound (6) is obtained with a yield of 84%.

Example I-7: Mono-AP26, Compound (7) of Table I

Firstly, Step 1 as described in Example I-1 above is carried out.
Step 2

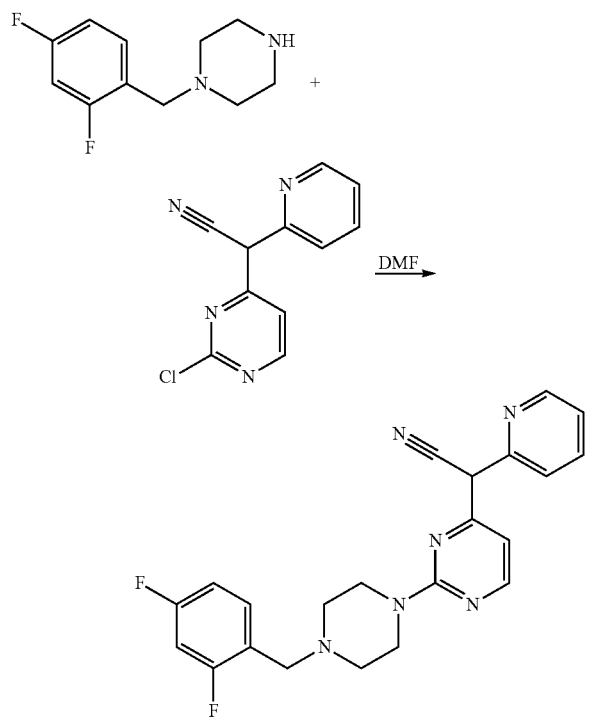

The halogenated intermediate is dissolved in 0.1 M in DE in presence of one equivalent of 1-(2,4-difluoro-benzyl) piperazine and one equivalent of DIEA and the reaction mixture is heated to 130° C. for 1 hour. The reaction medium is evaporated and the product purified by chromatography on a C18 semi-automatic device in a water/methanol gradient. Compound (7) is obtained with a yield of 89%.

Example I-8: Mono-AP27, Compound (8) of Table I

Firstly, Step 1 as described in Example I-1 above is carried out.
Step 2

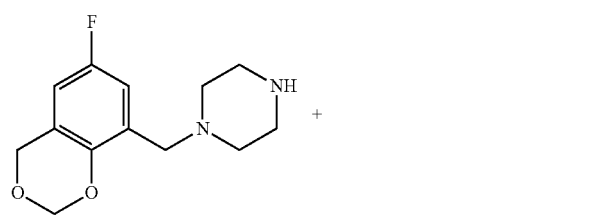

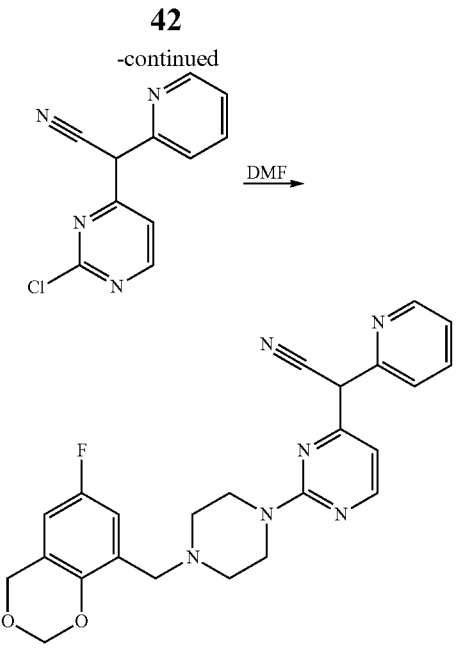

The halogenated intermediate is dissolved in 0.1 M in DMF in presence of one equivalent of 1-(6-fluoro-4H-benzo [1,3] dioxin-8-ylmethyl) piperazine and a equivalent of DIEA and the reaction mixture is heated at 130° C. for 1 hour. The reaction medium is evaporated and the product purified by chromatography on a C18 semi-automatic device in a water/methanol gradient. Compound (8) is obtained with a yield of 74%.

Example I-9: Mono-AP28, Compound (9) of Table I

Firstly, Step 1 as described in Example I-1 above is carried out.
Step 2

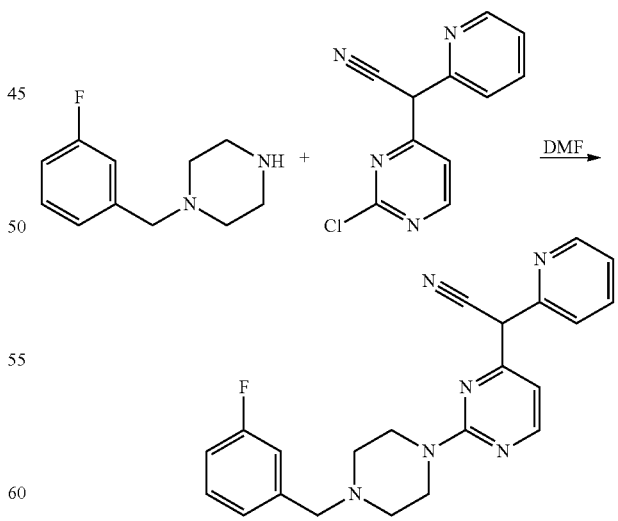

The halogenated intermediate is dissolved in 0.1 M in DMF in presence of one equivalent of 1-(3-fluoro-benzyl) piperazine and one equivalent of DIEA and the reaction mixture is heated to 130° C. for 1 hour. The reaction medium is evaporated and the product purified by chromatography on a C18 semi-automatic device in a water/methanol gradient. Compound (9) is obtained with a yield of 83%.

Example I-10: Mono-AP30, Compound (10) of Table I

Firstly, Step 1 as described in Example I-1 above is carried out.

Step 2

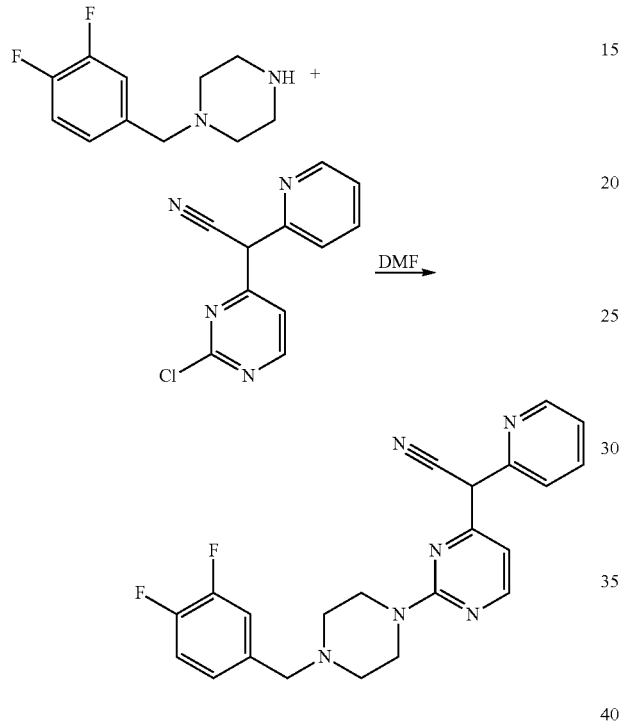

The halogenated intermediate is dissolved in 0.1 M in DMF in presence of one equivalent of 1-(3,4-difluorobenzyl) piperazine and one equivalent of DIEA and the reaction mixture is heated to 130° C. for 1 hour. The reaction medium is evaporated and the product purified by chromatography on a C18 semi-automatic device in a water/methanol gradient. Compound (10) is obtained with a yield of 87%.

Example I-11: Mono-AP3, Compound (12) of Table I

Firstly, Step 1 as described in Example I-1 above is carried out.

Step 2

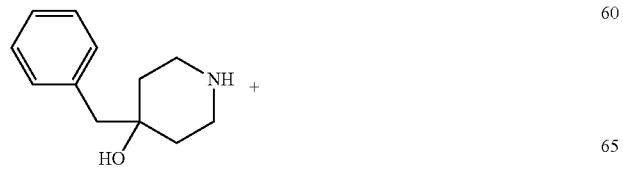

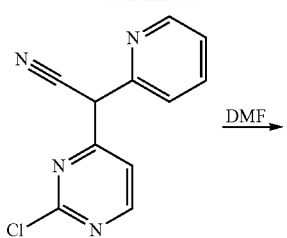

The halogenated intermediate is dissolved in 0.1 M in DMF in the presence of one equivalent of 4-benzyl-piperidin-4-ol and an equivalent of diisopropylethylamine (DIEA) and the reaction mixture is heated to 130° C. for 1 hour. The reaction medium is evaporated and the product purified by chromatography on a C18 semi-automatic device in a water/methanol gradient. Compound (12) is obtained with a yield of 71%.

Example I-12: Mono-AP2, Compound (11) of Table I

Steps 1, 2 and 3

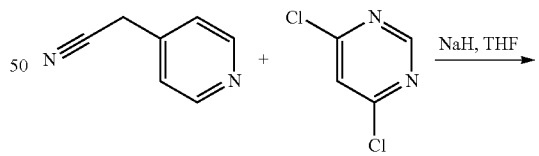

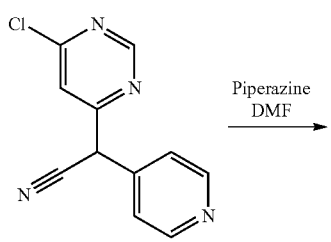

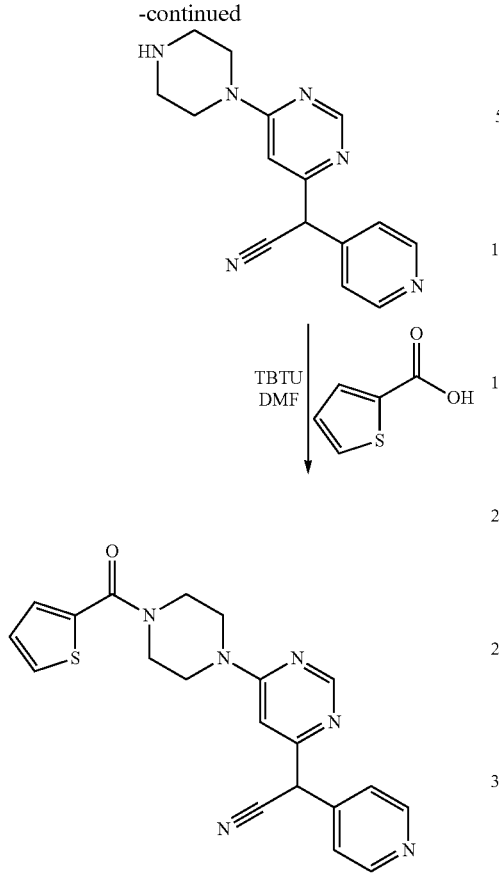

To a suspension of 1.1 equivalent of sodium hydride to 0.1 M in T is added dropwise a solution of one equivalent of 4-pyridylacetonitrile to 0.1 M in THF. The mixture is stirred for 30 minutes and then cooled to 0° C. by an ice bath. A solution of one equivalent of 4,6-dichloropyrimidine 1M in DMF was added dropwise and the reaction mixture is stirred overnight at room temperature. The reaction mixture is partially evaporated, diluted with water and returned to pH 7 with concentrated HCl. The solution is extracted with ethyl acetate, the organic phase is dried and evaporated to give an orange solid which was used without further purification.

The halogenated intermediate is dissolved in 0.1 Min DMF in the presence of 5 equivalents of piperazine and one equivalent of DIEA and the reaction mixture is heated at 130° C. for 1 hour. The reaction medium is evaporated and the product purified by chromatography on a $C_{18}$ semi-automatic device in a water/methanol gradient. The intermediate product is obtained with a yield of 50%.

The 2-thiophene carboxylic acid was dissolved at 0.2 M in DMF in the presence of two equivalents of DIEA. One equivalent of a 0.2 M solution of O-(benzotriazol-1-yl)-N, N, N', N'-tetramethyluronium tetrafluoroborate (TBTU) was added and the reaction mixture is stirred 5 minutes. One equivalent of 0.2 M amine intermediate in DMF is added and the reaction medium is stirred for 1 hour and then evaporated. The residue was redissolved in ethyl acetate and washed with 1 M $Na_2CO_3$ and then with water. The organic phase is evaporated and the product was purified on C18 in a water/methanol gradient. Compound (11) is obtained with a yield of 70%.

Example I-13: Di-AP2, Compound (13) of Table I

Step 1 and Step 2:

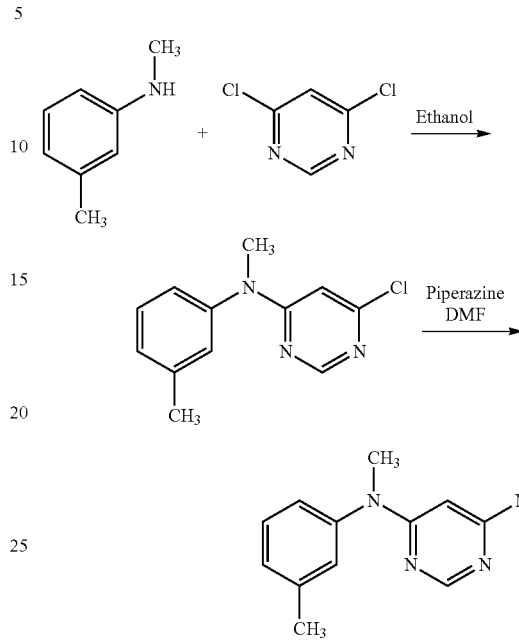

To a solution of one equivalent of 4,6-dichloropyrimidine in 0.1 M in ethanol was added a solution of one equivalent of N-methyl-m-toluidine 0.1 M in ethanol. The medium is refluxed for 4 hours and is then partially evaporated and diluted with water. The solution is extracted with ethyl acetate, the organic phase is dried and evaporated to give a solid which was used without further purification.

The halogenated intermediate is dissolved in 0.1 M in DMF in the presence of 5 equivalents of piperazine and one equivalent of DIEA and the reaction mixture is heated at 130° C. for 1 hour. The reaction medium is evaporated and the product purified by chromatography on a C18 semi-automatic device in a water/methanol gradient. The intermediate product is obtained with a yield of 50%.

Step 3:

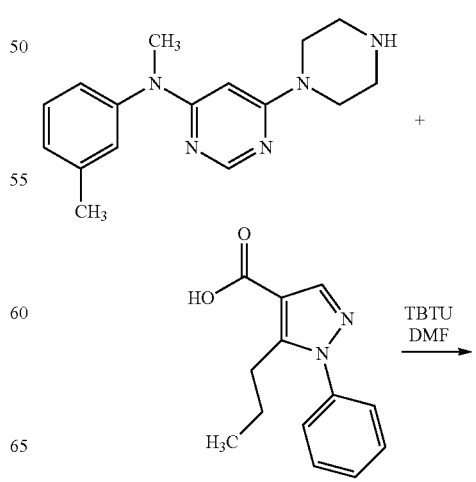

-continued

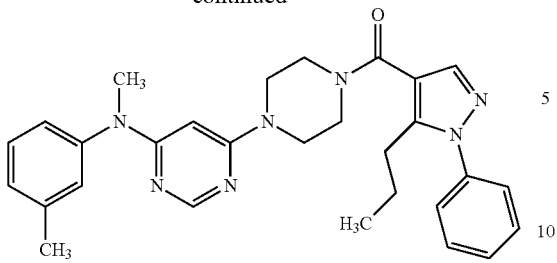

1-Phenyl-5-propyl-1H-pyrazole-4-carboxylic acid is dissolved at 0.2 M in DMF in the presence of two equivalents of DIEA. One equivalent of a 0.2 M solution of TBTU was added and the reaction mixture is stirred 5 minutes. One equivalent of 0.2 M amine intermediate in DMF is added and the reaction medium is stirred for 1 hour and then evaporated. The residue was redissolved in ethyl acetate and washed with 1 M Na$_2$CO$_3$ and then with water. The organic phase is evaporated and the product was purified on C18 in a water/methanol gradient. Compound (13) is obtained with a yield of 70%.

Example I-14: Di-AP1, Compound (14) of Table I

Step 1 and Step 2 as defined above in example I-13 are carried out.
Step 3:

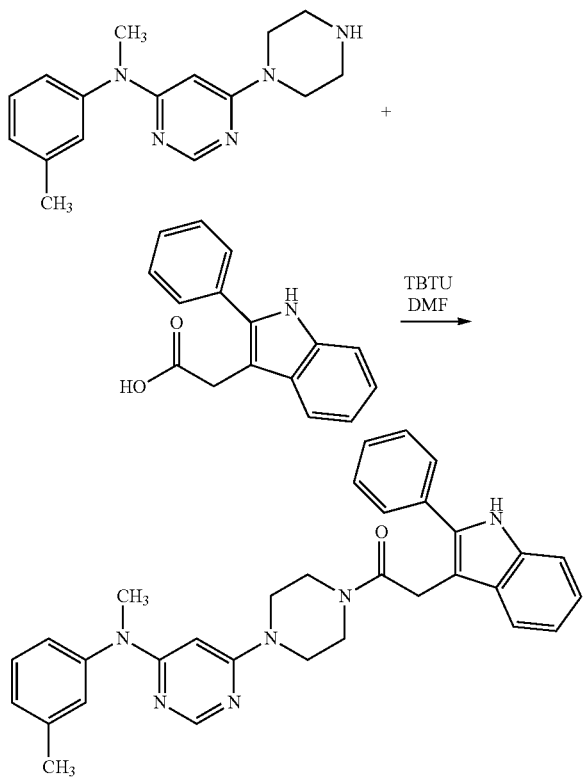

(2-Phenyl-1H-indol-3-yl) acetic acid is dissolved at 0.2 M in DMF in the presence of two equivalents of DIEA. One equivalent of a 0.2 M solution of TBTU was added and the reaction mixture is stirred 5 minutes. One equivalent of 0.2 M amine intermediate in DMF is added and the reaction medium is stirred for 1 hour and then evaporated. The residue was redissolved in ethyl acetate and washed with 1 M Na$_2$CO$_3$ and then with water. The organic phase is evaporated and the product was purified on C18 in a water/methanol gradient. Compound (14) is obtained with a yield of 74%.

Example II: Pharmacological Data

A. Materials and Methods
Fibroblasts Reprogramming
Fibroblasts used in this study were isolated from patient biopsies performed in the Assistance Publique Hôpitaux de Marseille for the patient 13-8243 and provided by Coriell Cell Repository (Camden, USA) for control DM4603. The fibroblasts were reprogrammed to iPS cells using Yamanaka's original method with OCT4, KLF4, SOX2, c-Myc, transferred using retroviral vectors (Takahashi et al., 2007, Cell 131, 861-872).

Pluripotent Stem Cells Culture and Differentiation
WT and HGPS iPS cells were grown on STO mouse fibroblasts, inactivated with 10 mg/ml mitomycin C seeded at 30000/cm$^2$ and grown as previously described (Nissan et al., 2012, Cell reports 2: 1-9).

For differentiation, iPSC were differentiated into mesenchymal stem cells MSC using directed protocols for differentiation previously published by our group (Nissan et al., 2012, Cell reports 2: 1-9).

Prelamin A Localization Cell-Based Assay
2000 HGPS MSCs were plated in black 384-well clear-bottom plates (Corning). After 48 h of drug treatment, cells were fixed in 4% paraformaldehyde (15 minutes, room temperature). Permeabilization, blocking and primary hybridization steps were done concomitantly in a PBS solution supplemented with 0.1% triton X-100 and 1% BSA (Sigma-Aldrich, St. Louis, USA) and rabbit anti-prelamin A (ANTOO45, Diatheva) overnight at 4° C. Cells were stained with the species-specific fluorophore-conjugated secondary anti-rabbit antibody (Invitrogen) (one hour, room temperature) and nuclei were visualized with Hoechst 33342. These steps were automated using a washing/staining station (ELx405 Biotek, RapidStak Thermo, Multidrop Labsystems). Prelamin A localization was analyzed with an ayScan VTI HCS Reader (Cellomics). The first channel was used for nucleus identification (Hoechst 33342 staining) and the second one to identify prelamin A staining. Pictures were acquired with a 5× objective in high-resolution camera mode and were analyzed using the Spot Detector bioapplication. The robustness of the assay was evaluated using the Z' factor calculated as ollows $Z'=1-[3(SDP+SDN)/(MP-MN)]$ where MP and MN correspond to the means of the positive (tipifarnib 1 μM) and negative (DMSO 0.1%) controls, respectively, and SDP and SDN correspond to their standard deviation.

Primary Screening Treatments
The primary screen was conducted on Biocell 1800 (Agilent). For this, 2000 HGPS MSCs were seeded in 38 μL of 20% FBS culture medium per well into black 384-well clear-bottom plates coated with 0.1% of gelatin. Five hours after seeding, 24 of 20× compounds from the chemical libraries were transferred in monoplicate into cell assay plates. In each plate, negative control (DMSO 0.1%) and positive control (tipifarnib 1 μM) were added in columns 1 and 2 respectively. Plates were then incubated for 48 hours and then processed for prelamin A detection assay. Each of the 72 plates of the screening were treated during 48 hours, fixed and stained with the specific anti-prelamin A antibody using the optimized protocols previously described. To prevent the discovery of toxic molecules, the number of cells per field was monitored in parallel and candidates showing mortality superior to 30% were excluded before their validation and their evaluation of phenotypical secondary phenotypes.

Chemical Library

Chemical library includes 21,608 compounds that belong to 4 different libraries distributed in 384-well plate format and obtained from Prestwick Chemical (Illkirch, France), LOPAC (Sigma-Aldrich, St. Louis, USA), CHEM-X-INFINITY (Romainville, France) and Curie Institute (Orsay, France). The Prestwick Chemical library contains 1120 FDA approved drugs. This library was tested at two concentrations: 0.2 µM and 5 µM. The LOPAC library (Sigma-Aldrich) contains a collection of 1280 pharmacologically active compounds. This library was tested at two concentrations: 0.2 µM and 10 µM. The Chem-X-Infinity library is composed of 10568 small organic molecules that belong to approximately 30 different chemical families. This library was tested at the concentration of 5 µM. The Institute Curie library contains 8,640 small molecules that were obtained during optimization programs against different therapeutic targets including anti-HIV, anti-kinases, protein-protein interactions, phosphatase inhibitors. This library was tested at 2.5 µg/mL that corresponds to concentrations comprised between 2 and 15 µM.

Data Analysis

Data analysis of the screening was performed using a customized Hiscreen application (Discngine, Paris, France) connected to Spotfire software (Tibco Co). Screening robustness was evaluated by calculating for each plate the Z'factor on the percentage of prelaminA nuclei parameter. Raw data related to the percentage of cells with prelamin A nuclei and to cell number per field were normalized to the average of DMSO controls. Hits selection was performed using in parallel a Z-score plate and a Z-score run method on these normalized data. Only hits whose Z-score plate and/or Z-score run was ≥3 and that did not decrease cell number by more than 30% compared to DMSO condition were selected for subsequent validation steps. These latter were retested in quadruplicate at the same concentration as for the primary screen. Validated hits were then tested at gradual concentrations for parallel exploration of their efficacy, potency and toxicity.

Osteogenic Differentiation

MSC were seeded at 600 cells per well in 384 well plate in MSC culture medium and treated as previously described. After 72 hours, MSC medium was replaced by STEMPRO osteogenic induction medium (Invitrogen) in presence or not of the different drugs. After 7 days of treatment, cells were fixed with ethanol 95% and stained by adding either a colorimetric substrate of the alkaline phosphatase, the 5-Bromo-4-chloro-3-indolyl phosphate/Nitro blue tetrazolium (NBT) (Sigma-Aldrich) or a chromogenic substrate of this enzyme (absorbance at 405 nm), the p-Nitrophenyl Phosphate (pNPP) (Pierce Biotechnology).

Immunocytochemistry

In the 4-steps protocol, cells were fixed in 4% paraformaldehyde (15 minutes, room temperature) before permeabilization and blocking in PBS supplemented with 0.1% triton X-100 and 1% BSA (Sigma-Aldrich, St. Louis, USA). Primary antibodies were incubated one hour at room temperature in blocking buffer. Antibodies included mouse anti-lamins A/C (clone JOL2, Millipore, Billerica, USA), rabbit anti-prelamin A (ANTOO45, Diatheva) and anti-Ki67 (clone Ki-S5, MAB4190, Millipore, Billerica, USA). Cells were stained with the species-specific fluorophore-conjugated secondary antibody (Invitrogen) (one hour, room temperature) and nuclei were visualized with Hoechst 33342.

ATP Measurement

HGPS and control MSC were seeded in a 96 well plates (3917, Corning) (5000 cells/well) and treated with the different drugs. After 48 hours of treatment in unique dose, ATP content was measured using CellTiter Glo® (Promega) accordingly to the manufacturer recommendations. Luminescence was measured with an Analyst GT multimode plate reader (Molecular devices). In parallel, Hoechst 33342 stained nuclei were counted in each well thanks to an automated microscope. The results exploited are given in the ratio between ATP measurement and the number of nuclei counted.

Western Immunoblotting

Whole-cell lysates of MSC were collected, separated by SDS-PAGE, and transferred onto PVPF membrane by liquid transfer method. Blots were blocked in 10% skim milk (Bio-Rad) in tween 0.1% tris-buffered saline (TTBS) 1× one hour at room temperature. The primary antibodies used were a mouse anti-lamins A/C 1:200 (Millipore, JOL2), a rabbit anti-prelamin A 1/100 (ANTOO45, Diatheva) and a β-actin 1/200000 (Sigma). Membranes were incubated during the night at 4° C. Antigen-antibody binding was detected using horseradish peroxidaseconjugated species-specific secondary antibodies (GE-Healthcare, Little Chalfont, UK) followed by enhanced chemiluminescence Western blotting detection reagents (Perkin-Elmer, Waltham, USA).

Quantitative PCR

Total RNA was isolated using RNeasy Mini extraction kit (Qiagen, Courtaboeuf, France) according to the manufacturer's protocol. An on-col DNase I digestion was performed to avoid genomic DNA amplification. RNA level and quality were checked using the Nanodrop technology. A total of 500 ng of RNA was used for reverse transcription using the Superscript III reverse transcription kit (Invitrogen). Q-PCR analysis was performed using a ABI 7900 system (Applied biosystem) and TaqMan gene expression Master Mix (Roche) following the manufacturer's instructions. Quantification of gene expression was based on the DeltaCt Method and normalized on 18S expression (Assay HS_99999901_S1). PCR primers were previously described by S. Rodriguez and colleagues (Rodriguez S et al., 2009, Eur J Hum Genet, VOL 17(7): 928-37). Primer sequences were lamin A (exons 11/12), 5'-TCTTCTGCCTCCAGTGT-CACG-3' (SEQ N° 1) and 5'-AGT-TCTGGGGGCTCTGGGT-3' (SEQ N° 2); lamin C (exons 9/10), 5'-CAACTCCACTGGGGAAGAAGTG-3' (SEQ N° 3) and 5'-CGGCGGCTACCACTCAC-3' (SEQ ID N° 4) and Progerin (exons 11/12), 5'-ACTGCAGCAGCTCGGGG-3' (SEQ N° 5) and 5'-TCTGGGGGCTCTGGGC-3' (SEQ ID N° 6).

Taqman MGB probe sequences were lamin A (exon 11), 5'-ACTCGCAGCTACCG-3' (SEQ N° 7); lamin C (exon10), 5'-ATGCGCAAGCTGGTG-3' (SEQ ID N° 8) and Progerin (exon 11), 5'-CGCTGAGTACAACCT-3' (SEQ ID N° 9). Reporter and quencher dyes for the LMNA locus assays were 5' 6FAM and 3'-nonfluorescent quencher dye (NFQ; Applied Biosystems).

Molecular Docking

The structural analysis and docking studies are based on crystal structure available from the Protein Data Bank. Structure of chain C and D of HMGCR were extracted from a complex with Pyrrole-based inhibitor (PDB id: 2Q1L, resolution of 2.05 Å). hFPPS was modeled using crystal structure (PDB id: 1YV5, resolution of 2.00 Å), including its three magnesium atoms but excluding its co-crystallized ligand. Farnesyl transferase crystal structure (PDB id: 3E37, resolution of 1.80 Å) was used, keeping its zinc cation but removing its inhibitor. For both of these structures, hydrogen atoms were added and center of mass of experimental cocrystallized ligands were used to define the center of binding site, where conformational search was performed. AutoDock 4.2.1 was used for all docking calculations, using default values for docking parameters except the number of genetic algon (GA) runs which was increased from 10 to 200 to increase conformational search. The resulting independent GA runs were then processed using clustering analysis with a 2.0 Å cutoff.

GCR Colorimetric Activity Assay

HMGCR activity was measured using GCoA Reductase Assay Kit (Sigma-Aldrich) according to the manufacturer's protocol. The assay is based on the spectrophotometric measurement of the decrease in absorbance at 340 nm, which represents the oxidation of NADPH by the catalytic subunit of HMGCR in the presence of the substrate HMG CoA.

Preparation of Cell Lysates for FPPS and FT Activity Assays

Cell pellet of HGPS MSCs were resuspended in 25 mM Tris-HCl pH 7.4, 1 mM DTT, 1 mM MgCl2, 1 EDTA, 1 mM PMSF and centrifuged at 10,000×g for 10 min at 4° C. Protein content was determined using Lowry's method. Aliquots of cell lysate containing 100 µg of total proteins were incubated with tested substances at 37° C. for 30 min.

FPPS Activity Assay

FPPS assay was carried out with some modifications of the procedure of Krisans et al. (Krisans et al., 1994, The Journal of biological chemistry VOL. 269: 14165-14169) and described by Gupta et al. (Gupta et al., 1999, Eur J Med Chem, VOL. 43: 2751-2767). Briefly, FPPS was assayed in 150 µL containing 25 mmol/L Hepes, pH=7, 2 mmol/L MgCl2, 1 mmol/L dithiothreitol, 5 mmol/L KF, 1% A noctyl-β-glucopyranoside, 3.3 µmol/L [4-14C] IPP (18 Ci/mmol), 3 µmol/L unlabeled IPP and 20 µmol/L geranyl diphosphate. Reactions were started by adding 40 µL of treated or untreated cell lysate and incubated for 45 min at 37° C. Reactions were stopped by the addition of 150 µL 2.5 mol/L HCl in 80% ethanol containing 100 µg/mL farnesol as a carrier. The samples were hydrolyzed for 30 min at 37° C. to convert the FPP to farnesol and neutralized by the addition of 150 µL of 10% NaOH. The reaction product (farnesol) was extracted into 1 mL of N-hexane and an aliquot (200 µL) of the organic phase was used for radio-activity counting. Parallel samples were assayed to evaluate the total and the nonspecific radioactivity. In all experiments, enzyme assays were carried out in triplicate.

FT Activity Assay

FT activity was determined by Farnesyltransferase [3H] SPA enzyme assay (Amersham Life Science, Buckinghamshire, England). Briefly, FT activity was assayed in 20 µl of assay buffer containing 50 mmol/L Hepes, 30 mmol/L MgCl2, 20 mmol/L KCl and 5 mmol/L dithiothreitol, 20 µl of [3H]-FPP (12 pmol) and 20 µl of biotin lamin B. Reactions were started by adding 40 µL of treated or untreated cell lysate and incubated for 1 hour at 37° C. Reactions were stopped by the addition of 150 µL of stop reagent containing SPA bead and counted in a scintillation counter. FT activity was expressed as pmoles of incorporated [3H]-FPP into biotin lamin-B peptide per minute per milligram of total proteins (pmol/min/mg prot). Parallel samples were assayed to evaluate the total and the nonspecific radioactivity. In all experiments enzyme assays were carried out in triplicate.

Measure of farnesylated proteins HGPS MSCs were treated 48 h with Click-IT® Farnesyl alcohol (Life technologies) in presence of the compounds. Farnesylated proteins were secondarily revealed using Alexa Fluor® 555 azide (Life technologies) according to manufacturer's protocol.

Surface Plasmon Resonance

Surface plasmon resonance (SPR) was measured using a BIAcore 3000 instrument at 25° C. FPPS (2800 RU) was immobilized on flow cells of a CM5-chip. The running buffer was HBSEP pH 7.4 (20 mM Hepes, 150 mM NaCl, and 0.005% P20). Regeneration was performed with 10 mM glycine, pH 3.0. Measurements for affinity determinations of FPPS binders were performed with compounds injected at concentrations ranging from 1.95 nM to 5 µM. Data were evaluated using Scrubber2 (Biologic software) and BIAeval software (BIAcore).

Measure of Ras Farnesylation

Ras farnesylation was measured by analyzing GFP localization in HGPS MSCs overexpressing a plasmid encoding the CaaX box of mammalian hRas fused to GFP at the C terminus.

Live Cell Imaging

HGPS MSCs were seeded at 2500 cells per well in 96-well plates and cultivated during 7 days in presence of the drugs. Cell density was monitored using an IncuCyte ZOOM microscope (Essen Bioscience). Each value corresponds to the mean of cell densities of four pictures taken in three independent wells.

Statistical Analysis

Statistical analysis has been performed by one-way analysis of variance (ANOVA), using the et's comparison test. Values of $p<0.05$ were considered significant (*$p<0.05$, $p<0.01$, *$p<0.001$).

B Results

B.1. Identification of Inhibitors of Prelamin A Farnesylation by High throughput Screening This study was performed on MSCs derived from HGPS iPS cells, differentiated as previously described (Blondel et al., 2014, Stem Cells Transl Med, VOL. 3: 510-519) and used after ten passages of amplification. The drug screening strategy was based on the detection of the subcellular localization of prelamin A, with the assumption that its nuclear localization was directly correlated to the inhibition of its farnesylation. A high throughput immunostaining assay was developed to robustly quantify prelamin A expression and localization in 384-well plates. DMSO 0.1% and a FTI (tipifarnib 1 µM) were used as negative and positive controls, respectively. The drug screening assay was optimized in order to obtain a homogeneous and reproducible prelamin A staining in HGPS MSCs treated with FTIs in 384-well plates. Quality control of the assay was assessed by the calculation of a Z' factor superior to 0.8 between negative and positive controls. 21,608 small molecules from 4 different compound libraries were then tested following the different steps of the screening procedure. Quantification of prelamin A localization was performed using an automated imaging platform measuring the proportion of HGPS MSCs that presented prelamin A staining in the nuclear matrix compartment 48 hours after the pharmacological treatment.

Compounds were considered as potential candidates when their effect was superior to 3 standard deviations of the mean of all the tested compounds without affecting cell viability more than 30%. This led to a first list of 59 hits.

Retest experiments excluded 43 of those candidates because they were either toxic or deemed false positives.

Figure 1A:
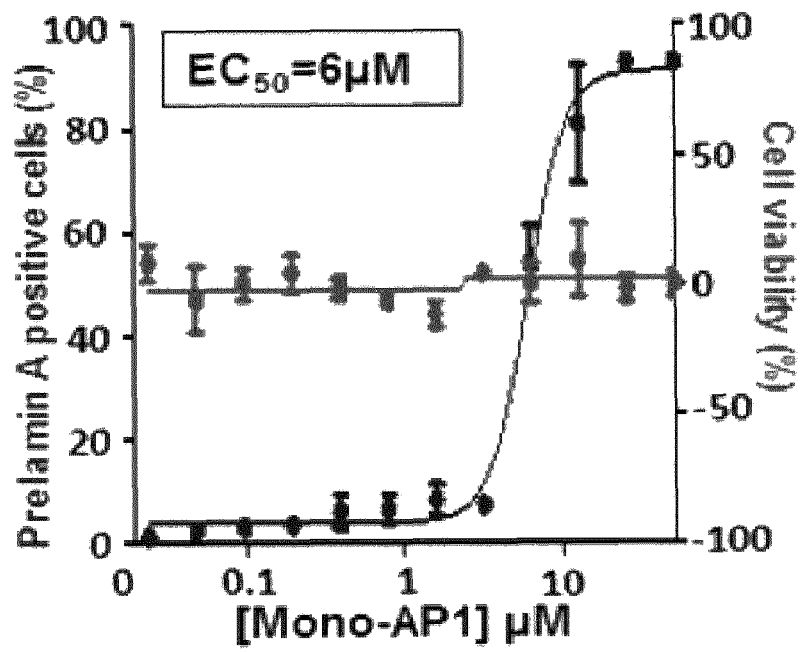
FIG. 1: High throughput screening of 21608 small molecules on prelamin a maturation Dose-response experiments of the 5 prelamin A modulators identified:
- (1A) Mono-AP1,
- (1B) Mono-AP2,
- (1C) Mono-AP3,
- (1D) Di-AP1 and
- (1E) Di-AP2, and
- (1F) FTI.
Figure 1B:
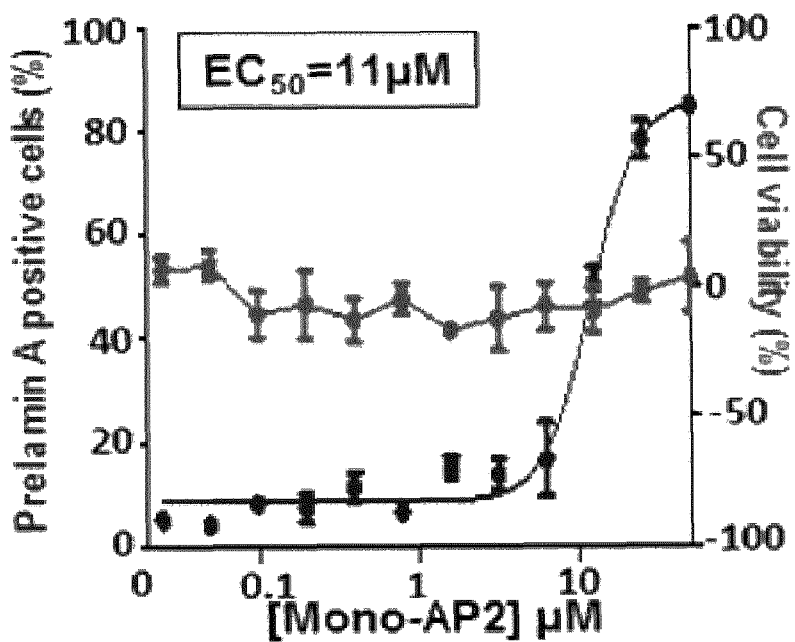
Figure 1C:
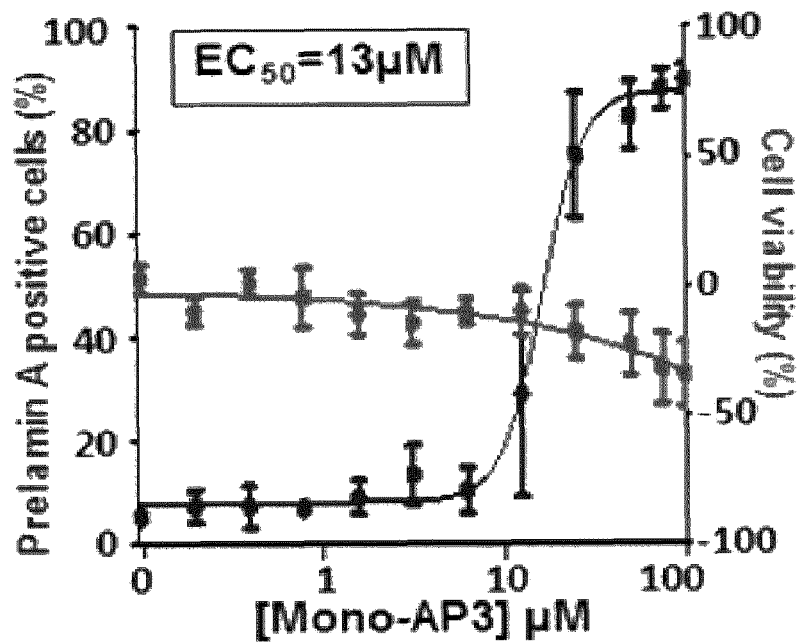
Figure 1D:
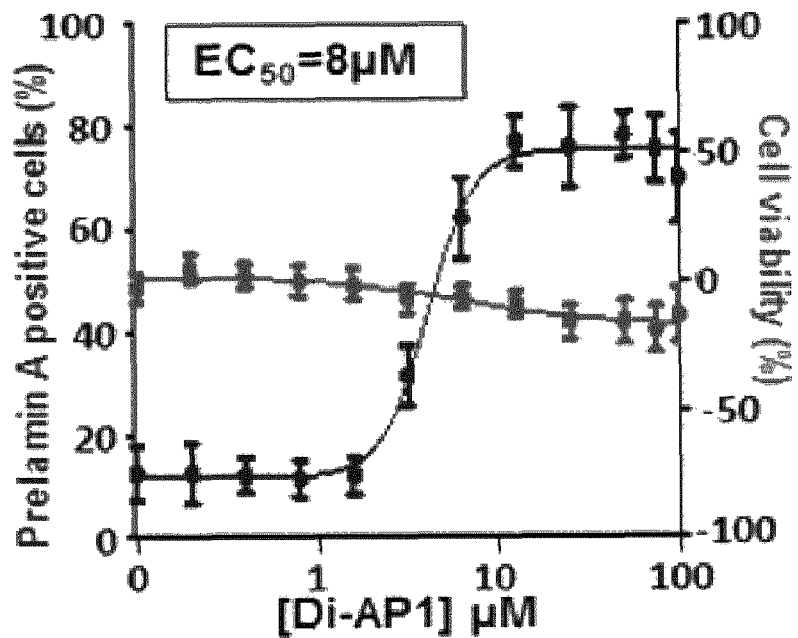
Figure 1E:
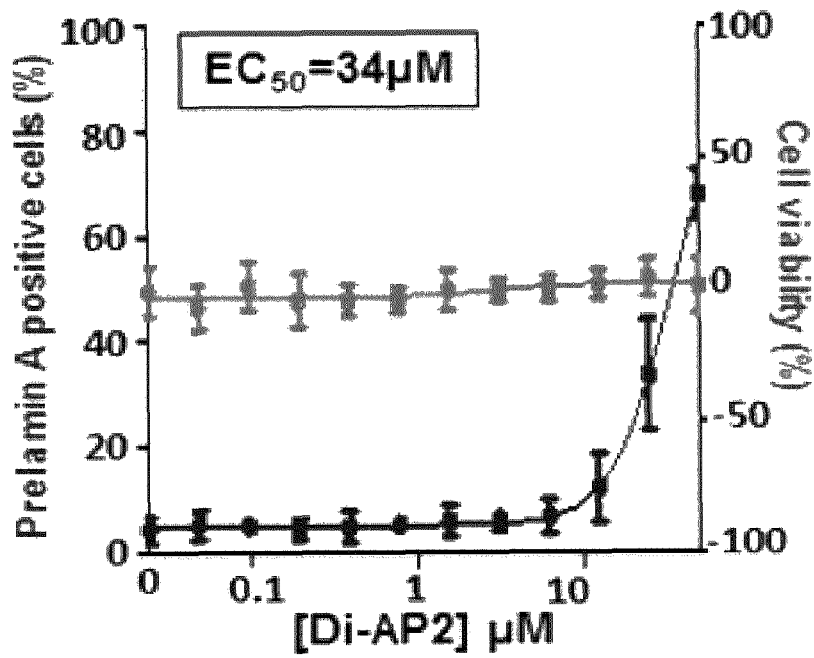
Figure 1F:
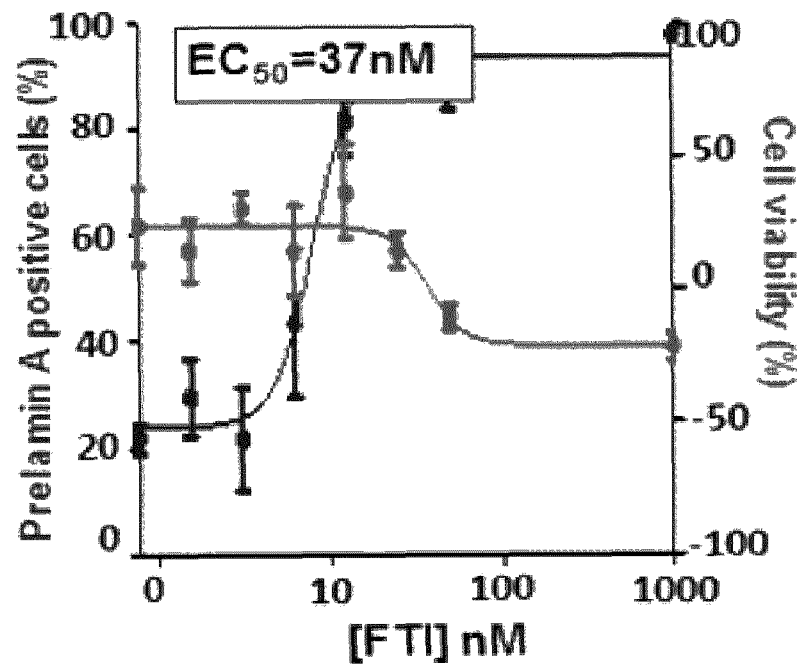

The drug screening process was completed for the 16 validated compounds by an evaluation of their efficiency and toxicity in progressively larger dosages, revealing an efficiency superior to 50% without cell toxicity for 5 (FIGS. 1A and 1B). EC50 ranged between 1 µM and 34 µM, with a plateau at the highest nontoxic doses over 80% of nuclear prelamin A localization (FIGS. 1A-1E). Optimal concentrations were determined for each compound as the highest efficient concentrations on prelamin A nuclear localization without toxicity, and were used subsequently for secondary and functional assays. Western blot analyses confirmed that prelamin A was increased in cells treated with each of the 5 compounds (Mono-AP1, Mono-AP2, Mono-AP1, Di-AP1, and Di-AP2) whereas quantitative PCR revealed the post-translational effect of the drugs showing that, except for one (Di-AP1), neither lamin A nor progerin mRNA expression was increased after the different treatments (FIG. 5A et 5B). Immunostainings confirmed the absence of effect on progerin expression at the protein level in presence of any of these drugs.

Chemical structure analysis of the 5 hits showed that 5 of them contained an aminopyrimidine group (AP) with one, two or four nitrogen atom bindings, respectively named Mono-APs, and Di-APs. Measures of cell toxicity demonstrated that none of these compounds were toxic at therapeutic doses. Finally, the lack of selectivity for farnesylation of prelamin A was demonstrated by observing similar effects on two other prenylated proteins, HDJ2 and hRas. Western blot analysis of HDJ2 revealed an increase of the unfarnesylated form of the protein after Mono-AP1, Mono-AP2, Mono-AP3, Di-AP1, and Di-AP2, treatments. hRAS farnesylation, as measured by its localization in HGPS MSCs overexpressing a plasmid encoding the CaaX box of mammalian hRas fused to GFP at the C terminus, showed a significant increase of the unfarnesylated CAAX box in presence of all compounds. These results were confirmed by an overall decrease of the levels of farnesylated proteins in HOPS MSCs after monoaminopyrimidines treatment.

Functional Effects of the 5 Hits on HGPS-associated Defects

Figure 2A:
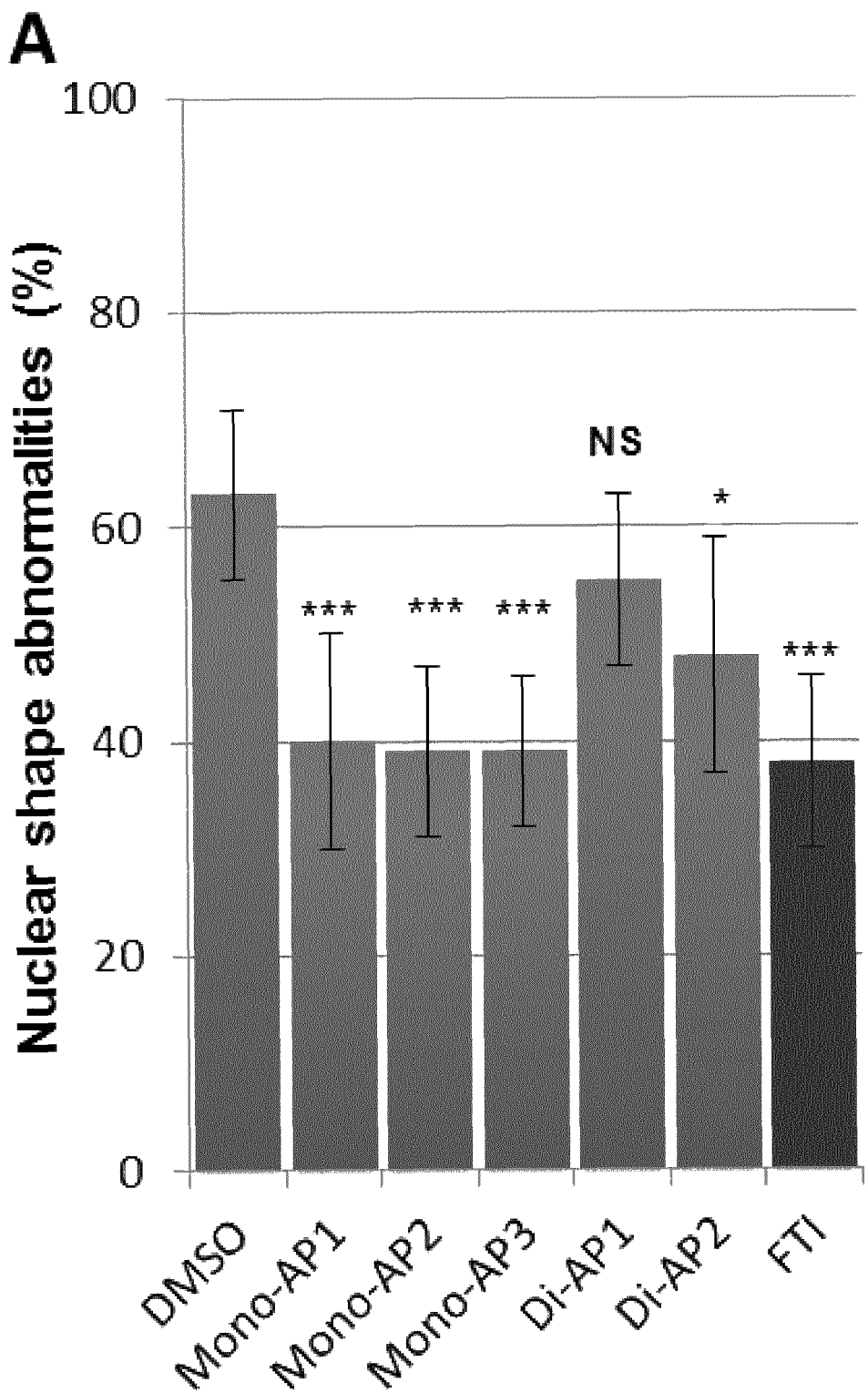
Figure 2B:
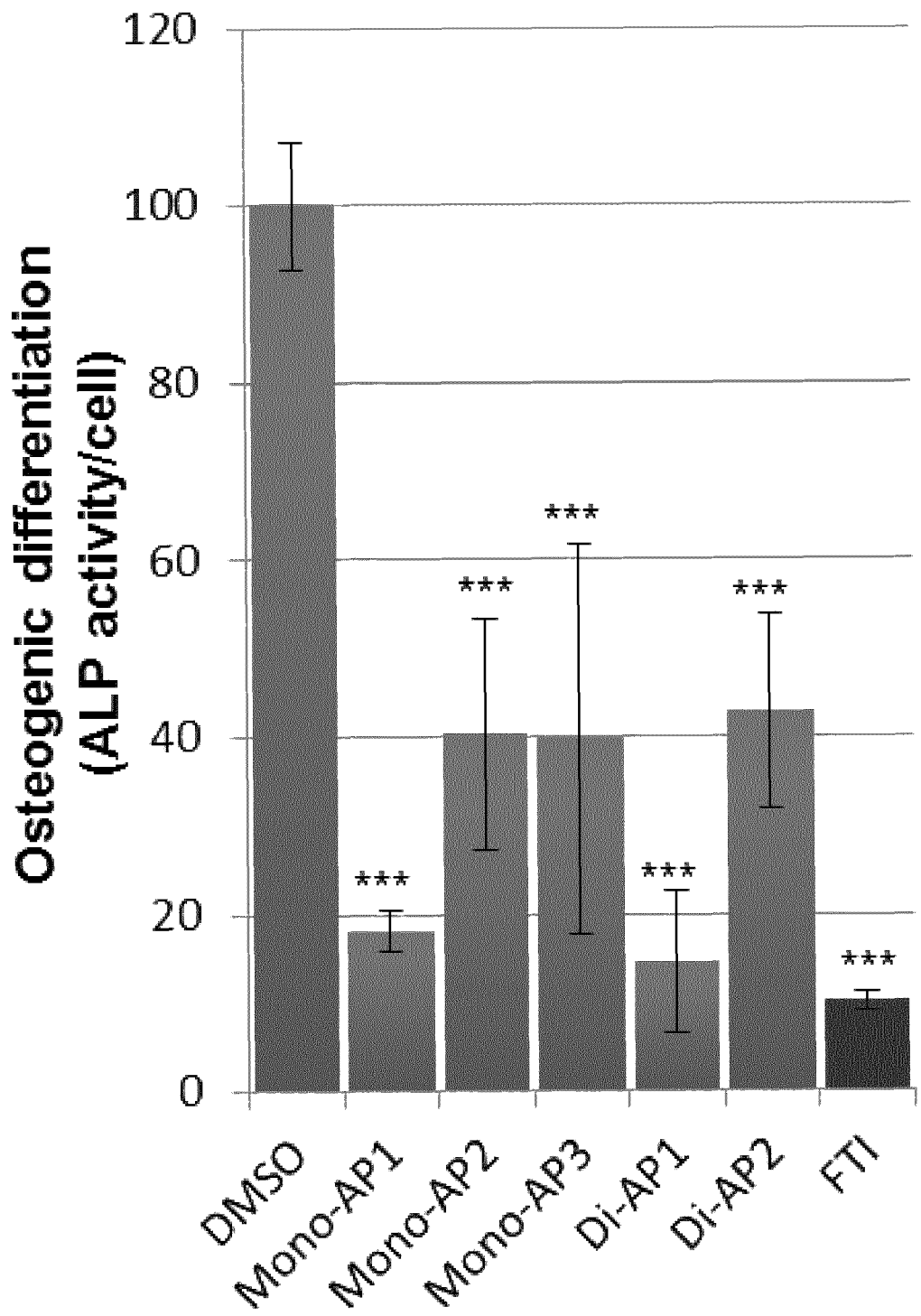

The 5 hits were evaluated on their capacity to rescue nuclear shape abnormalities. HGPS MSCs were treated 48 h in presence of the different compounds and stained for lamin A/C. Mono-AP1, Mono-AP2 and Mono-AP3 were the three most efficient compounds, restoring HGPS MSCs nuclear shape defects at levels not significantly different from the FTI tipifarnib used as a positive control. Di-AP2 also restored significantly this pathological structural defect, whereas Di-AP1 was not efficient (FIG. 2A). HGPS MSCs exhibit a premature differentiation into the osteoblastic lineage (Blondel et al., 2014, Stem Cells Transl Med VOL. 3: 510-519; Scaffidi and Misteli, 2008, Nat Cell Biol VOL. 10, 452-459). Accordingly, the effect of each of the 5 hits was monitored on this functional impairment via a measure of alkaline phosphatase activity following 7 days of osteogenic differentiation. All the compounds were able to strongly rescue this phenotype, at levels for Mono-AP1 and Di-AP1 that is not significantly different to those observed following FTI treatment (FIG. 2B).

Figure 2C:
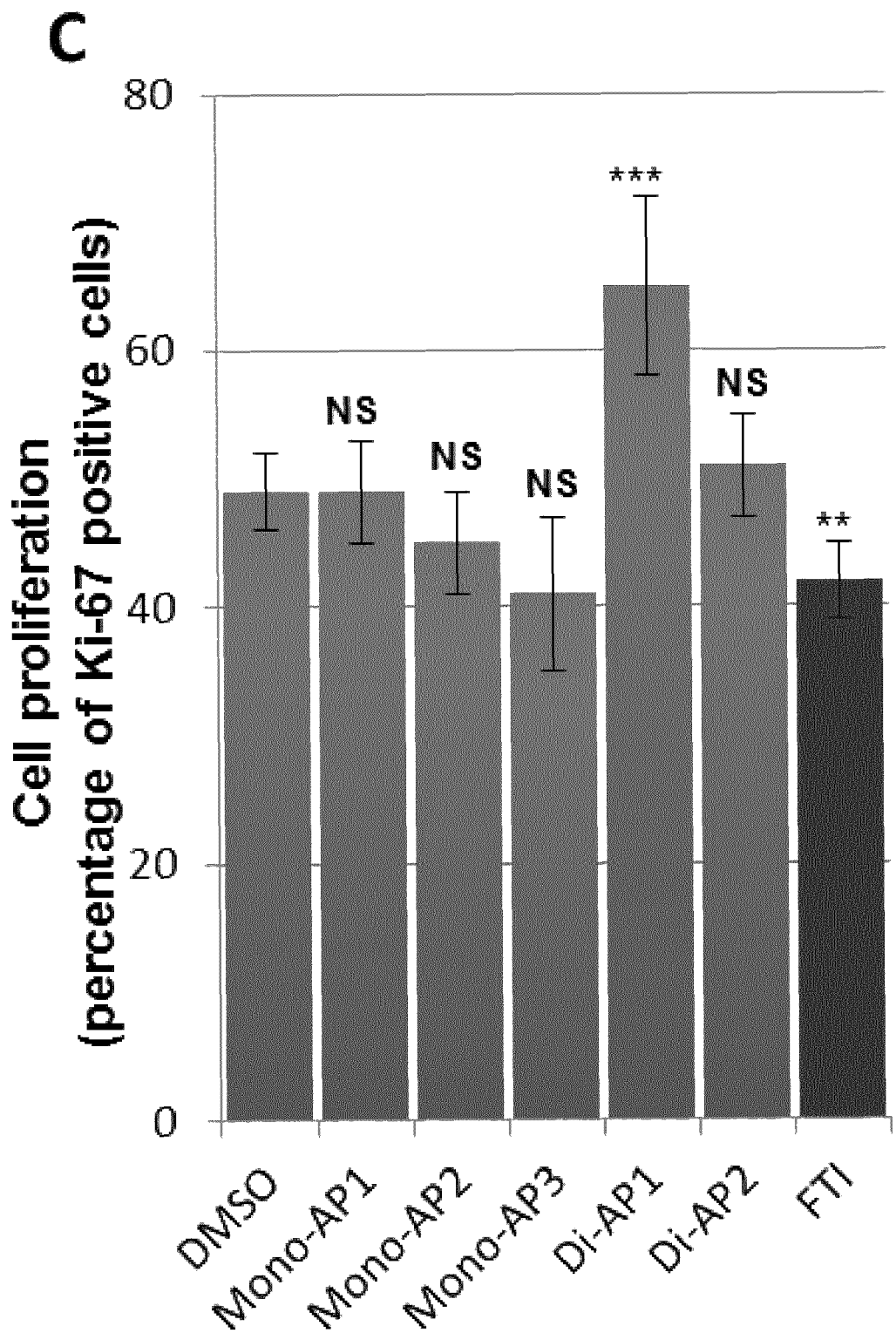

Potential adverse effects of the 5 compounds were assessed by measuring cell proliferation and energetic metabolism. Quantification of Ki-67 positive proliferating cells did not reveal decreased proliferation of MSCs treated with the compounds (FIG. 2C). It is interesting to mention that Di-AP1 was instead capable of increasing the number of Ki-67 positive cells up to 65%. Results were confirmed in long term live imaging cultures showing that Mono-AP1, Mono-AP2 and Mono-AP3 were less cytostatic than the FTI tipifarnib. ATP content of HGPS MSCs was measured, revealing no adverse effect of any of these molecules on energetic metabolism. On the contrary, Di-AP1 increased ATP content.

Mode of Action of Mono-aminopyrimidines

Because Mono-APs were the most efficient compounds for rescuing the two functional defects tested without inducing adverse effects, the last part of this study that concerned mode of action of the drugs was focused on them.

Figure 3A:
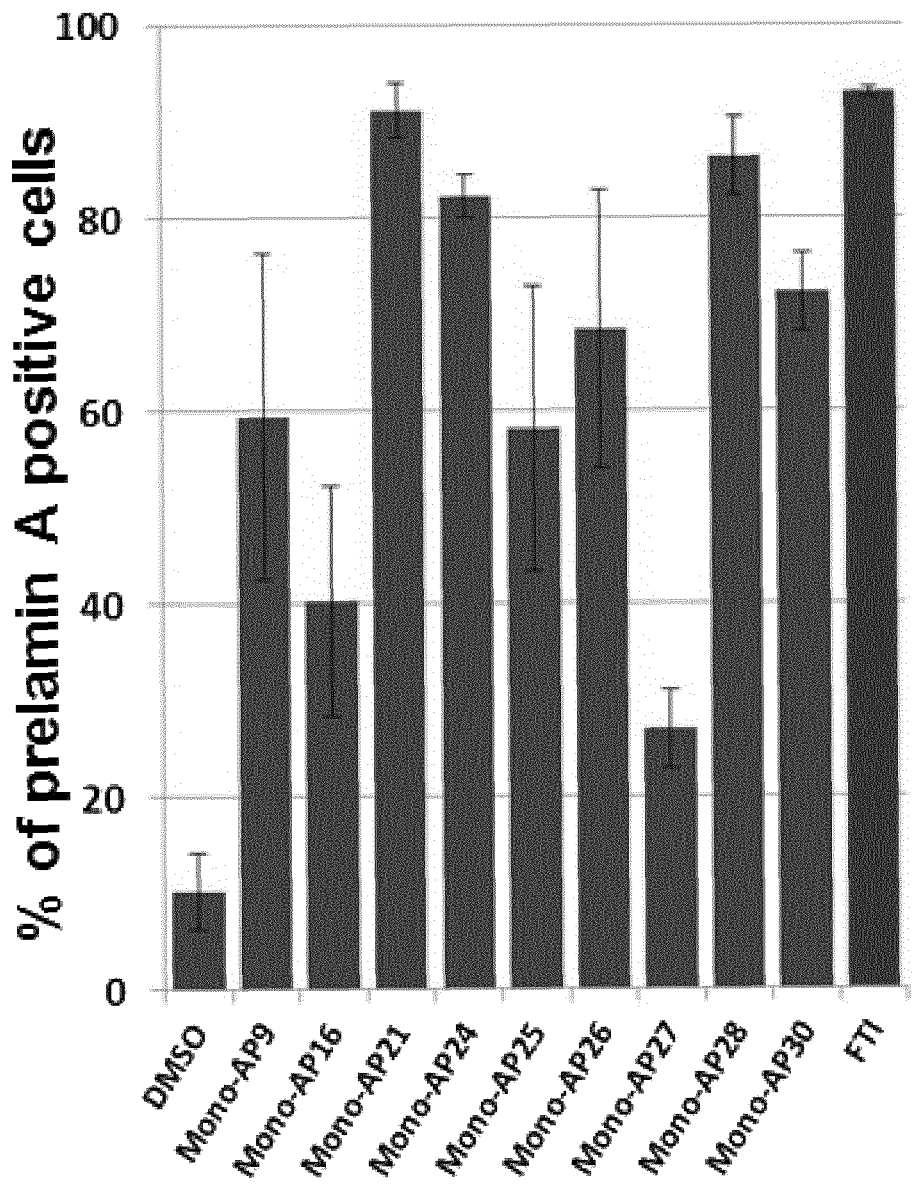
Figure 3B:
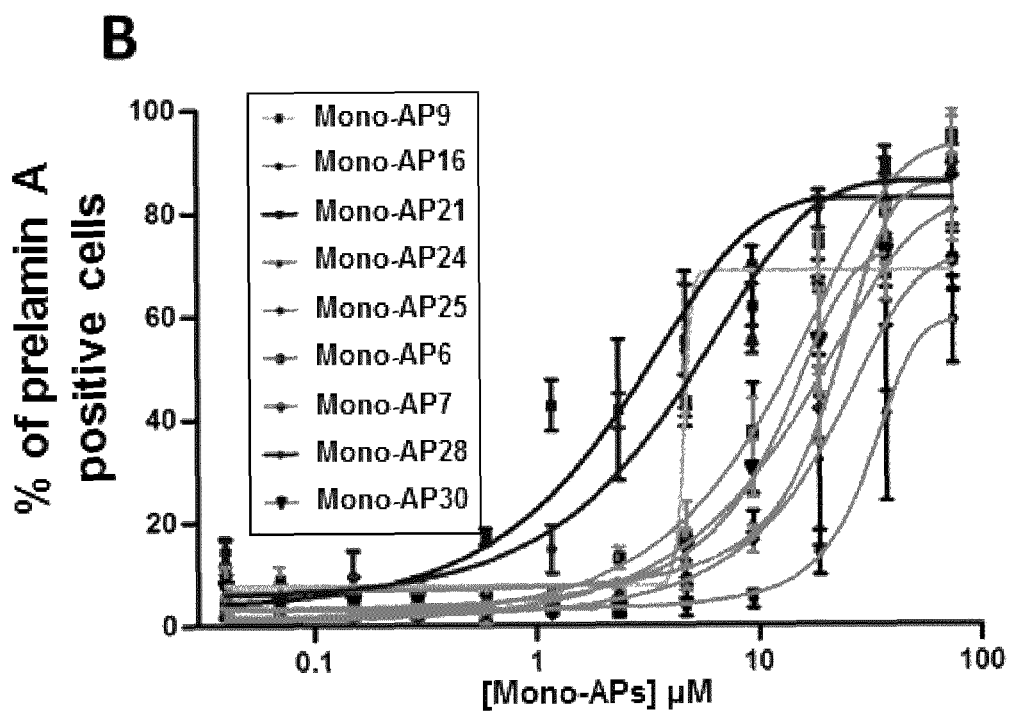
Figure 3C:
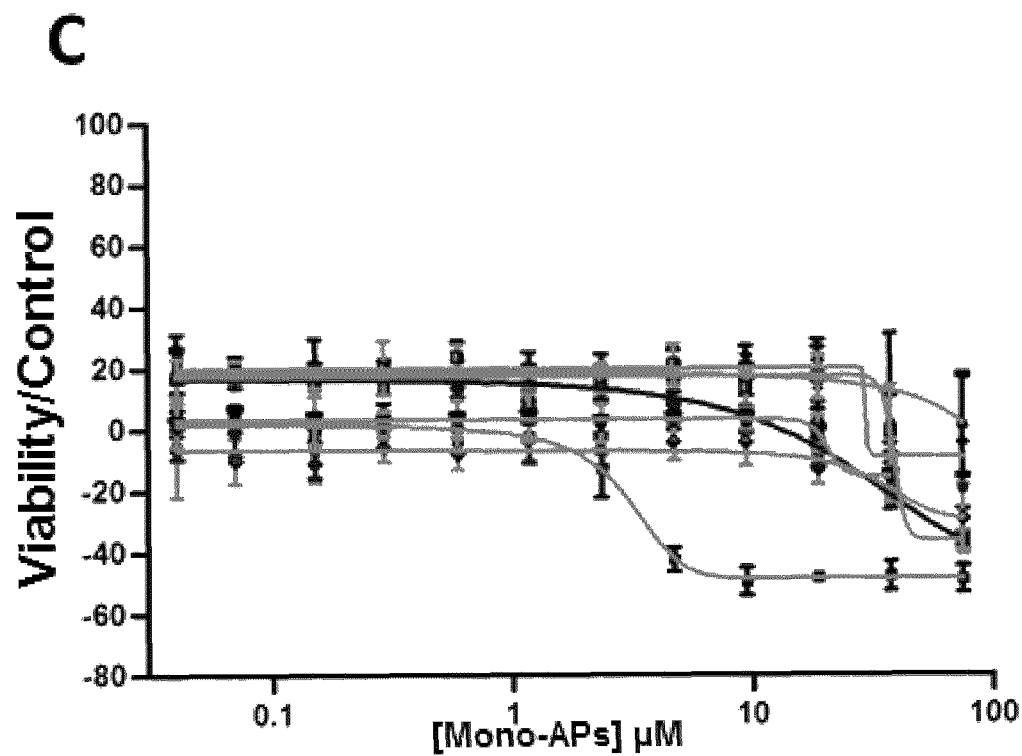

For that purpose, a library of 47 chemical analogous was derived from Mono-AP1 ({2-[4-(2-Fluoro-benzyl)-piperazin-1-yl]-pyrimidin-4-yl}-pyridin-4-yl-acetonitrile), and evaluated at a 10 µM concentration on the farnesylation of prelamin A. This set of experiments revealed that 9 compounds exhibited an effect superior to 20% on prelamin A localization (FIG. 3A). Dose response experiments of these 9 second-generation Mono-APs showed that only two of them, Mono-AP21 and Mono-AP28 were more efficient than Mono-AP1, with EC50s of 1.5 µM and 2 µM, respectively (FIGS. 3B and 3C). After treatments with Mono-AP21 and Mono-AP28, a similar capacity was observed at rescuing the nuclear shape defects and premature osteogenesis in HGPS MSCs.

Substitution of the benzyl group appended to the piperazine nucleus with a functionalized chain like —$CH_2CO_2Et$, such as in Mono-AP25, led to a decrease in efficiency (FIG. 3B).

Finally, direct interactions of Mono-AP1, Mono-AP2 and Mono-AP3 were virtually assessed with three key enzymes controlling protein prenylation, HMG-CoA reductase (HMGCR), farnesyl pyrophosphate synthase (FPPS) and farnesyl transferase (FT), in order to highlight potential paths for optimization of the compounds. Calculation of binding energies of Mono-APs with the three enzymes indicated potential interaction with the active sites of FPPS and FT, but not HMGCR (FIG. 5B). Docking of Mono-AP1 and Mono-AP3 on FPPS revealed the major role of the phenyl domain of these compounds for cation-pi interaction with $Mg2+$ cation of FPPS. Appropriate substitution like electron donating group (Me, OMe, or $NH_2$) may reinforce the binding of the phenyl domain of Mono-AP3 to $Mg2+$ cation. Mono-AP1 showed more affinity for FT than Mono-AP2 and Mono-AP3, because of the presence of hydrogen bonds with amino acids Y861B and S599B. Finally, biochemical experiments confirmed the direct inhibition of both FPPS and FT but not HMGCR by Mono-APs, with a 20% decrease of FT activities and 40% for FPPS (FIGS. 4A, 4B and 4C, FIGS. 7A, 7B and 7C).

Mono-APs (Mono-AP1 and Mono-AP2) interactions with FPPS were confirmed by surface plasmon resonance (SPR) experiments. Accordingly, FPPS was immobilized on a CM5 chip and its interaction with Mono-APs was measured with a Biacore platform.

Results of these experiments confirmed the direct interactions of Mono-AP1 and Mono-AP2 with FPPS, and equilibrium dissociation (Kd) and association (Ka) constants could be calculated for both interactions (see Table A below).

TABLE A

|      |        | Mono-AP1       | Mono-AP2        |
|------|--------|----------------|-----------------|
| FPPS | Kd (M) | $2.4 * 10^{-5}$ | $2 * 10^{-4}$  |
|      | Ka (1/M) | $9.5/10^3$   | $5.04 * 10^3$   |

Validation of molecular docking and SPR results was performed by measuring biochemical activities of the three enzymes FT, FPPS and HMGCR in presence of Mono-APs. Results of biochemical tests confirmed the direct inhibition of both FPPS and FT but not GCR by Mono-APs, with a 20% to 30% decrease of FT activities and 40% to 50% decrease for FPPS activities.

Finally, dose-response experiments permitted to determine values of IC50 of Mono-AP1,2 and 3 on FT and FPPS enzymatic activities ranging from 0.35 to 9.32 µM (see Table B below).

IC50 values correspond to the concentration of the tested aminopyridine compound which induces 50% of the maximum inhibiting effect measured for the said aminopyridine compound.

TABLE B

| IC50 (µM) | Mono-AP1      | Mono-AP2      | Mono-AP3      |
|-----------|---------------|---------------|---------------|
| FPPS      | 1.55          | 1.82          | 5.54          |
| FT        | 3.46          | 9.32          | 0.35          |
| HMGCR     | No inhibition | No inhibition | No inhibition |

The main result of the example herein is the discovery of a new family of farnesylation inhibitors capable of rescuing pathological phenotypes associated to HGPS (FIG. 6). Beyond their potential use for the treatment of HGPS, this result underscores a new type of molecules for disorders already treated with farnesylation inhibitors. It also highlights the unique potential of iPS cells derivatives for drug discovery.

The persistence of an abnormal farnesylated motif at the C terminal end of misprocessed prelamin A is the main molecular mechanism leading to progerin toxicity in HGPS (Cau et al., 2014, Semin Cell Dev Biol.). Following this discovery, several teams have demonstrated the interest of several known inhibitors of prenylation by designing independent preclinical and clinical studies with FTIs and a combination of a biphosphonate and a statin (Gordon et al., 2012, Proc Natl Acad Sci USA VOL. 109: 16666-16671; Varela et al., 2008, Nat Med VOL. 14: 767-772). The results of the FTI-based clinical trials revealed some limited improvements in patients but underscored, nevertheless, the need for new molecules that would be more efficient and less toxic (Gordon et al., 2012, Proc Natl Acad Sci USA VOL. 109: 16666-16671). The present study was based on the assumption that it was possible to identify such compounds without targeting one specific enzyme but rather the entire process of prelamin A prenylation.

Interestingly, among the whole hits that came out of the screen of 21,608 small molecules, it came as an internal control that three—one statin and two quinolines—had already been identified in other studies as prelamin A farnesylation modulators (Varela et al., 2008, Nat Med VOL. 14: 767-772; Yang et al., 2005, Proc Natl Acad Sci USA VOL. 102: 10291-10296.). In fact, QCs had originally been described as inhibitors of RAS farnesylation, and their therapeutic use was thus suggested as anti-proliferative agents in cancer (Jasinski et al., 2008, Invest New Drugs VOL. 26: 223-232.). QCs have also been evaluated in patients with malaria for their ability to inhibit farnesyl transferase in *Plasmodium falciparum* (Eastman et al., 2006, Journal of lipid research VOL. 47: 233-240; Gupta and Prabhakar, 2008, Eur J Med Chem VOL. 43: 2751-2767; Nallan et al., 2005, J Med Chern VOL. 48, 3704-3713; Van Voorhis et at, 2007, Antimicrobial agents and chemotherapy 51, 3659-3671) and later, in keeping with their ability to interfere with farnesylation, evaluated to improve nuclear shape abnormalities in HGPS patients' fibroblasts (Capell et al., 2005, Proc Natl Acad Sci USA Vol. 102, 12879-12884). Besides, statins, that have been widely prescribed in humans as HMGCR inhibitors to reduce cholesterol levels and prevent cardiovascular disorders(Goldstein and Brown, 1990, Nature VOL. 343: 425-430), were also described as potential HGPS treatments(Varela et al., 2008, Nat Med VOL. 14, 767-772).

The most striking result of our high throughput drug screening was the fact that the 5 compounds identified, shared a common chemical structure, an aminopyrimidine group. Subsequent analysis of a set of 47 related chemicals reinforced this result by adding 9 other compounds to the initial list. Even if there are probably different targets and modes of action for the aminopyrimidines described in the literature, it is interesting to note that other recent studies have highlighted the therapeutic potential of that family of compounds. Over the past 10 years, aminopyrimidines have been described as highly potent inhibitors of B-Raf (Mathieu et al., 2012, J Med Chem VOL. 55:2869-2881), JAK (Tyner et al., 2010, Blood VOL. 115, 5232-5240), CDK1/2 inhibitors (Ryu et al., 2011, Bioorg Med Chem Lett VOL. 21: 7185-7188) or EGFR and ErbB-2 (Xu et al., 2008, Bioorg Med Chem Lett VOL. 18: 4615-4619.). An aminopyrimidine, the nilotinib, was also described to inhibit Bcr-Abl tyrosine-kinase inhibitors (TKI) the first-line therapy target for most patients with chronic myelocytic leukemia (Verstovsek et al., 2005, Cancer VOL. 104: 1230-1236).

Docking studies have suggested that pyrimidines analogues may bind geranyl transferase, suggesting an implication in the regulation of protein prenylation (Ethiraj et al., 2013, Chem Biol Drug Des VOL. 82: 732-742). The addition to bisphosphonates of a pyrimidine group, the thienopyrimidine, has also been shown to increase their binding to the allylic subpocket of farnesyl pyrophosphate synthase (Leung et al., 2013, J Med Chem VOL. 56: 7939-7950). The present results described aminopyrimidines as inhibitors of protein prenylation, revealing their capacity at regulating this process in the absence of bisphosphonates. Docking results were in keeping, as they showed that Mono-APs, displayed a strong affinity to the FPPS and FT active sites resulting in biochemical experiments to a decrease of FT and FPPS activities of respectively 20% and 40%.

Since the discovery of the protein prenylation mechanism in fungi in 1978 (Kamiya et al., 1978, Biochem Biophys Res Commun VOL. 83: 1077-1083), more than 100 proteins have been experimentally confirmed to undergo prenylation, among which notably the small GTPAses Rho, Ras, Rac and Cdc24 (Lane and Beese, 2006, Journal of lipid research VOL. 47: 681-699). Because these small GTPases are essential in many cellular events, e.g. intracellular signal transduction, proliferation, inflammation and motility, a wealth of efforts have been made to identify compounds inhibiting prenylation with a therapeutic perspective. First suggestions for therapeutic use of inhibitors of farnesylation as anticancer drugs, were made in 1982 with the identification of the RAS multigenic family as human oncogenes, and the subsequent demonstration that they required farnesylation for expressing their malignant transforming activity (Bos, 1989, Proc Natl Acad Sci USA VOL. 102: 12879-12884.). Experimental studies seemed to comfort the therapeutic potential of farnesyl transferase inhibitors since, depending upon the context, they induce apoptosis, cell cycle arrest or inhibit cell proliferation, cell migration and angiogenesis (Berndt et al., 2011, Nat Rev Cancer VOL. 11: 775-791). Accordingly, since 2000, at least 75 clinical trials have been conducted in various cancer indications, using four different FTIs, namely tipifarnib, lonafarnib, BMS☐214662 and L☐778123 (William et al., 2012, Journal of medicinal chemistry 55, 169-196). However, most of these clinical trials have not been successful. As an example, no significant increase of lifespan was observed in patients with advanced solid cancers (Van Cutsem et al., 2004, journal of the American Society of Clinical Oncology 22, 1430-1438) or acute myeloid leukaemia (Chevallier et al., 2009, Leuk Res VOL. 33: 1124-1126.). As most drugs exhibited a very narrow therapeutic window, with toxicity appearing at doses close to the ones used in patients, one explanation for that failure could be a nonoptimal dosage in patients. Towards reaching the goal of an optimal benefit/risk ratio, the fact that Mono-APs were as efficient as tipifarnib on farnesylation without inducing cell toxicity, is encouraging. Another cause for failure may have been the restriction of activity on farnesyl transferase, as there may be alternative prenylation of N-Ras and K-Ras (i.e. geranylgeranylation) in the presence of FTIs. This has led to the development of global prenylation inhibitors that were described to target FPPS or HMGCR. To date, the inhibitors of FPPS most commonly used in the clinic are chemically stable analogues of inorganic pyrophosphate, all members of the bisphosphonates class (Burr and Russell, 2011, Bone VOL. 49: 1). These compounds are mainly used as a treatment for osteoporosis because they inhibit bone resorption. There are two major groups of compounds with distinct molecular mechanisms. The first one comprises the non-nitrogen bisphosphonates, such as clodronate and etidronate that mimic pyrophosphate and inhibits osteoclasts, ultimately causing their death, probably by interference with mitochondrial ATP translocases (Lehenkari et al., 2002, Mol Pharmacol VOL. 61: 1255-1262.). The second group, the nitrogen-containing compounds (N-BPs) such as zoledronate, interferes with specific metabolic reactions through the inhibition of FPPS. They thus regulate a variety of cell processes controlled by these targets and important for osteoclast function, including cell morphology, cytoskeletal arrangement, membrane ruffling, trafficking of vesicles and apoptosis (Ridley et al., 1992, Cell VOL. 70: 389-399) (Ridley et al., 1992, Cell VOL. 70: 401-410). More recently, a new type of FPPS inhibitors were described, the N6-isopentenyladenosine, showing improvements of nuclear shape abnormalities in progeroid fibroblasts (Bifulco et al., 2013, The FEBS journal VOL. 280: 6223-6232). In this study, we demonstrate that Mono-APs bind to both FPPS and FT, adding yet another mode of action by targeting protein prenylation at multiple sites. In consequence, and as for the existing prenylation inhibitors, the potential used of Mono-APs in therapeutical perspectives will need to be monitored to avoid undesirable side effects due to the lack of specificity on prelarnin A.

Since the discovery of human pluripotent stem cells, disease-specific cells have become a major tool for drug validation and discovery. Among the well-acknowledged advantages of those cells as compared to other cell models are their human origin, their physiological or pathological non-transformed status, and their ability at unlimited self-renewal and the possibility to derive theoretically any cell phenotype of the organism. As concerns drug discovery through HTS, pluripotent stem cells derivatives also offer the possibility to assay phenotypictraits instead, or in addition to specific biochemical targets. Over the past 10 years, several studies have made use of this capacity. First drug screenings on pluripotent stem cells were focused on the identification of compounds that would regulate stem cell maintenance (Andrews et al., 2010, Nat Rev Cancer VOL. 11: 775-791; Desbordes et al., 2008, Cell Stem Cell VOL. 2: 602-612) or cellular differentiation (Zhu et al., 2009, Cell Stem Cell VOL. 4: 416-426) (Shan et al., 2013, Nat Chem Biol VOL. 9: 514-520). More recently, different phenotypic drug screens have appeared, to which the present study is adding one more successful example, that aimed at discovering potential therapeutic paths for specific diseases, such as cardiac hypertrophy (Carlson et al., 2013, J Biomol Screen VOL. 18: 1203-121) and familial dysautonomia, for which KF-86466 was identified as a potential treatment (Lee et al., 2012, Nat Biotechnol VOL. 30: 1244-1248.). In addition to all those advantages that already make them unique, it is interesting to underline the fact that those cells are amenable to functional testing. As this is the case in the present article, secondary assays may thus complement and provide a physiological validation of an otherwise more reductionist primary drug screening assay. Here, this has provided us with the ability to counterscreen immediately all candidates hit compounds on phenotypic traits associated to HGPS. On that basis, it was possible to prioritize the compounds and select the most promising ones towards performing a structureactivity relationship study, in a cost and time effective manner.

Therefore, the result of the tests carried out on the compounds disclosed in the present invention show that said compounds may be useful to treat and/or prevent diseases or disorders wherein an inhibition of protein prenylation is required. Among all, said diseases or disorders may include Hutchinson-Gilford progeria syndrome (HGPS), progeria, a neurodegenerative disease, Parkinson's Disease, diffuse Lewy body disease, multiple system atrophy, Shy-Drager syndrome, striatonigral degeneration, olivopontocerebellar atrophy, pantothenate kinase-associated neurodegeneration, cognitive impairment, dementia, a lysosomal storage disease, glycogen storage disease type II, mucopolysaccharidoses, mucolipidosis II, mucolipidosis III, mucosulfatidosis, GM2 activator protein deficiency variant AB, Danon disease, Salla disease, Tay-Sachs disease, Sandhoff disease, Schindler disease, Kanzaki disease, alpha-mannosidosis, beta-mannosidosis, fucosidosis, sialidosis, aspartylglucosaminuria, carbohydrate-deficient glycoprotein syndrome, Wolman disease, Farber disease, Niemann-Pick disease types A, B, and C, Gaucher disease, Krabbe disease, Fabry disease, multiple sulfatase deficiency, GM1 gangliosidosis, GM2 gangliosidosis, GM3 gangliosidosis, galactosialidosis, cystinosis, sialic acid storage disease, pyknodysostosis, metachromatic leukodystrophy, galactosialidosis, neuronal ceroid lipofuscinosis, lactosylceramidosis, Pompe disease, cobalamin definiciency type F, amyotrophic lateral sclerosis, Huntington's Disease, Alzheimer's Disease; a mitochondrial disease, an ocular disease, an inflammatory disease, a cardiovascular disease, a proliferative disease, depression, anxiety, an immune disease, a neoplastic disease, a tumor, a cancer, a metastase, a leukemia, a carcinoma, a melanoma, a sarcoma, a glioblastoma, a multiple myeloma, an adenoma, a neoplasia, a neuroblastoma, an adenocarcinoma, a lymphoma, a myeloma, a multiple myeloma, a myelodysplastic syndrome, acute myeloid leukemia, chronic myeloid leukemia, chronic myelomonocytic leukemia, angiogenic myeloid metaplasia, a mesothelioma, a glioma, atherosclerosis, bilestones, cholelithiasis, lipocalcinogranulomatosis, hypercholesterolemia, hyperlipoproteinaemia, cholesterol crystal embolism, myocardial infection, cerebral infarction, angina pectoris, osteoporosis, arthritis, rheumatoid arthritis, osteoarthritis, Paget's Disease, Neurofibromatosis Type 1, Leopard Syndrome, Noonan Syndrome, Legius Syndrome, Costello Syndrome, hereditary gingival fibromatosis type 1, autoimmune lymphoproliferative syndrome, capillary malformation-arteriovenous malformation, skin aging, hormonal aging, photo-induced premature skin aging, aging myo-lipo-skin, restrictive dermopathy, alteration or loss of hair, alopecia, Hepatitis delta virus infection, and viral infection.

More particularly, the tumors and cancers are selected from bone, brain, kidney, liver, adrenal gland, colorectal, urinary bladder, breast, stomach, ovaries, colon, rectum, prostate, pancreas, lung, non-small cell lung, small cell lung, vagina, thyroid, the neck and head cancers and tumors.

Therefore, the claimed compounds of the present invention are useful to treat and/or prevent diseases or disorders wherein an inhibition of protein prenylation is required and which may be selected from a progeria disease, a neurodegenerative disease, a metabolic disease, a mitochondrial disease, an ocular disease, an inflammatory disease, a cardiovascular disease, a proliferative disease, an immune disease, cerebral infarction, skin aging, hormonal aging, and viral infection.

A progeria disease may be chosen among Hutchinson-Gilford progeria syndrome, Mulvihill-Smith progeria-like syndrome, and Wiedemann Rautenstrauch neonatale progeroid syndrome.

For example, among neurodegenerative diseases may be cited dementia, motor neurone disease, systemic atrophies primarily affecting central nervous system, Tay-Sachs disease, transmissible spongiform encephalopathies, ataxia telangiectasia, autosomal dominant cerebellar ataxia, Baggio-Yoshinari syndrome, Batten disease, Corticobasal degeneration, Creutzfeldt-Jakob disease, fatal familial insomnia, frontotemporal dementia and parkinsonism linked to chromosome 17, hereditary motor and sensory neuropathy with proximal dominance, infantile Refsum disease, Locomotor ataxia, Lyme ataxia, Macchado-Joseph disease, Mental retardation and microcephaly with pontine and cerebellar hypoplasia, multiple system atrophy, neuroacanthocytosis, Niemann-Pick disease, pontocerebellar hypoplasia, pyruvate deshydrogenase deficiency, protein aggregation, Refsum disease, Sandhoff disease, Shy-Drager syndrome, spinocerebellar ataxia, subacute combined degeneration of spinal cord, spinal muscular atrophy, subacute sclerosing panencephalitis, Tabes dorsalis, toxic encephalopathy, toxic leukoencephalopathy, Wobbly hedgehog syndrome, encephalitis, epilepsy, genetic brain disorders, head and brain malformations, hydrocephalus, Parkinson's disease, multiple sclerosis, amyotrophic lateral sclerosis (ALS ou Lou Gehrig's disease), Huntington's disease, Prion diseases, and Alzheimer's disease.

By way of examples, among a metabolic disease may be cited a lysosomal storage disease, obesity, hypothyroidism, hyperthyroidism, diabetes, hypolipidemia, galactosemia, phenylketonuria and a sialic acid storage disease.

Among lysosomal storage diseases may be cited gangliodoses, Gaucher disease, Niemann-Pick disease, Fabry's disease, ceramidosis (lipogrambulomatosis, Farber disease), sulfatidoses (metachromatic leukodystrophy), mucosulfatidosis (multiple sulfatase deficiency, Austin disease), globoid cell, leukodystrophy (Krabbe disease), Hurler (mucopolysaccharidoses (MPS) IH), Scheie disease (MPS IS or IV), Hunter (MPS II), Sanfilippo (MPS III), Morquio (MPS IV), Maroteaux-Lamy (MPS VI), Sly (MPS VII), glycogenosis type II or glycogen storage disease type II (also known as Pompe's disease).

Sialic acid storage disease may be selected from Infantile free sialic acid storage disease (ISSD), Salla disease, and intermediate severe Salla disease.

As mitochondrial diseases may be cited Alpers disease, Bait syndrome, Lethal Infantile cardiomyopathy, beta-oxidation defects, carnitine-acyl-carnitine deficiency, carnitine deficiency, co-enzyme Q10 deficiency, Complex I deficiency, Complex 11 deficiency, Complex III deficiency, Complex IV deficiency, Complex V deficiency, CPEO, CPT I deficiency, CPT II deficiency, KSS, lactic acidosis, LBSL-leukodystrophy, LCAD, LCHAD, Leigh disease, Luft disease, MAD/glutaric aciduria Type II, MCAD, MELAS, MIRAS, mitochondrial cytopathy, mitochondrial DNA depletion, mitochondrial encephalopathy, mitochondrial myopathy, diabetes mellitus and deafness (DAD or DMDF), Pearson syndrome, pyruvate carboxylase deficiency, pyruvate dehydrogenase deficiency, POLG mutations, respiratory chain, Leber's hereditary optic neuropathy, ataxia, retinis pigmentosa, ptosis, myoneurogenic gastrointestinal encephalopathy, myoclonic epilepsy with ragged red fibers (ME), SCAD, SCH and VLCAD.

An ocular disease may be chosen among ectropion, lagophtalmos, blepharochalasis, ptosis, xanthelasma of eyelid, dermatitis of eyelid, parasitic infestation of eyelid in leishmaniasis, loiasis, onchocerciasis, and in phthiriasis, involvement in eyelid in herpesviral infection, leprosy, molluscum contagiosum, yaws, zoster, and in tuberculosis, involvement of eyelid in impetigo, dacryoadenitis, epiphora, dysthyroid exophtalmos, conjunctivitis, scleritis, keratitis, corneal ulcer, corneal abrasion, snow blindness, Arc eyes, Thygeson's superficial punctuate keratopathy, corneal neovascularisation, Fuch's dystrophy, keratoconjunctivitis sicca, iritis, uveitis, cataract, chorioretinal inflammation, chorioretinal scars, choroidal degeneration, hereditary choroidal dystrophy, choroidal haemorrhage and rupture, choroidal detachment, chorioretinitis, retinal detachment, retinoschisis, retinal artery occlusion, retinal vein occlusion, retinopathy, age-related macular degeneration, peripheral retinal degeneration, retinitis pigmentosa, retinal haemorrhage, separation of retinal layers, macular edema, glaucoma, floaters, Leber's hereditary optic neuropathy, optic disc drusen, strabismus, ophthalmoparesis, esotropia, exotropia, hypermetropia, myopia, astigmatism, anisometropia, presbyopia, disorders of accommodation, amblyopia, Leber's congenital amaurosis, scotoma, color blindness, nyctalopia, blindness, red eye, and Argyll Robertson pupil.

For example, among inflammatory diseases may be cited Alzheimer's, ankylosing spondylitis, arthritis (osteoarthritis, rheumatoid arthritis (RA), psoriatic arthritis), asthma, atherosclerosis, Crohn's disease, colitis, dermatitis, diverticulitis, fibromyalgia, hepatitis, irritable bowel syndrome (IBS), systemic lupus erythematosus (SLE), nephritis, Parkinson's disease, ulcerative colitis.

By way of examples, among cardiovascular diseases may be cited coronary artery diseases (CAD) such as angina and myocardial infarction (commonly known as a heart attack), stroke, hypertensive heart disease, rheumatic heart disease, cardiomyopathy, atrial fibrillation, congenital heart disease, endocarditis, aortic aneurysms, peripheral artery disease and venous thrombosis.

Proliferative diseases may be selected from neoplastic diseases, tumors, cancers, metastases.

More particularly, as explained above, the tumors and cancers may be selected rum bone, brain, kidney, liver, adrenal gland, colorectal, urinary bladder, breast, stomach, ovaries, colon, rectum, prostate, pancreas, lung, non-small cell lung, small cell lung, vagina, thyroid, the neck and head cancers and tumors.

By way of examples, a cancer may be chosen among a leukemia, a carcinoma, a melanoma, a sarcoma, a glioblastoma, a multiple myeloma, an adenoma, a neoplasia, a neuroblastoma, an adenocarcinoma, a lymphoma, a myeloma, a multiple myeloma, a myelo-dysplastic syndrome, acute myeloid leukemia, chronic myeloid leukemia, chronic myelomonocytic leukemia, angiogenic myeloid metaplasia, a mesothelioma, and a glioma.

An immune disease may be chosen among Acute Disseminated Encephalomyelitis (ADEM), Acute necrotizing hemorrhagic leukoencephalitis, Addison's disease, Agammaglobulinemia, Alopecia areata, Amyloidosis, Ankylosing spondylitis, Anti-GBM/Anti-TBM nephritis, Antiphospholipid syndrome (APS), Autoimmune angioedema, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune oophoritis, Autoimmune pancreatitis, Autoimmune retinopathy, Autoimmune thrombocytopenic purpura (ATP), Autoimmune thyroid disease, Autoimmune urticaria, Axonal & neuronal neuropathies, Balo disease, Behcet's disease, Bullous pemphigoid, Cardiomyopathy, Castleman disease, Celiac disease, Chagas disease, Chronic fatigue syndrome, Chronic inflammatory demyelinating polyneuropathy (CIDP), Chronic recurrent multifocal ostomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic Esophagitis, Eosinophilic fasciitis, Erythema nodosum, Experimental allergic encephalomyelitis, Evans syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis (GPA) (formerly called Wegener's Granulomatosis), Graves' disease, Guillain-Barre syndrome, Hashimoto's encephalitis, Hashimoto's thyroiditis, Hemolytic anemia, Henoch-Schonlein purpura, Herpes gestationis, Hypogammaglobulinemia, Idiopathic thrombocytopenic purpura (ITP), IgA nephropathy, IgG4-related sclerosing disease, Immunoregulatory lipoproteins, Inclusion body myositis, Interstitial cystitis, Juvenile arthritis, Juvenile diabetes (Type 1 diabetes), Juvenile myositis, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic arthritis, Idiopathic pulmonary fibrosis, Pyoderma gangrenosum, Pure red cell aplasia, Raynauds phenomenon, Reactive Arthritis, Reflex sympathetic dystrophy, Reiter's syndrome, Relapsing polychondritis, Restless legs syndrome, Retroperitoneal fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Type 1 diabetes, Ulcerative colitis, Undifferentiated connective tissue disease (UCTD), Uveitis, Vasculitis, Vesiculobullous dermatosis, Vitiligo, and Wegener's granulomatosis (now termed Granulomatosis with Polyangiitis (GPA).

Skin aging may be selected from photo-induced premature skin aging and aging myoliposkin.

For example, among viral infections may be cited Chickenpox, Flu (influenza), Human immunodeficiency virus (HIV/AIDS), Human papillomavirus (HPV), infectious mononucleosis, mumps, measles and rubella, shingles, viral gastroenteritis (stomach flu), viral hepatitis, viral meningitis, dengue, chikungunya, viral pneumonia, bird Flu; Common Cold, Cytomegalovirus (CMV) Infection, Ebola Virus infection, Marburg Virus Infection, Hantavirus Infection, Herpes Simplex Virus Infections, Infectious Mononucleosis, Lassa Fever and South American Hemorrhagic Fevers, Middle East Respiratory Syndrome (MERS), Polio, Postherpetic Neuralgia, Severe Acute Respiratory Syndrome (SARS), Smallpox, H1N1 Swine Flu, and Yellow Fever.

For this purpose an effective amount of said compound may be administered to a patient suffering from a disease or a disorder wherein an inhibition of protein prenylation, and more precisely wherein an inhibition of protein farnesylation is required, and in particular from HGPS and progeria, and from the previous cited diseases.

The present invention is also related to the use of at least a compound chosen among a compound of anyone of formula (I), (II), (Ia), (Ib), (Ic), and (I'a) as defined above, and compounds (1) to (14) as defined above, or one of its pharmaceutically acceptable salts according to the present invention for the manufacture of a pharmaceutical composition intended for the treatment and/or prevention of a disease or a disorder wherein an inhibition of protein prenylation. and more precisely wherein an inhibition of protein farnesylation is required, and in particular HGPS and progeria but also all the previous listed diseases.

The present invention also encompasses pharmaceutical compositions comprising at least a compound chosen among new compounds of formula (I), (II), (Ia), (Ib), (Ic), and (I'a) as defined above and compounds (1) to (14), as defined above or any pharmaceutically acceptable salt thereof.

Thus, these pharmaceutical compositions contain an effective amount of said compound, and one or more pharmaceutical excipients.

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

The present invention further relates to a method of treatment of patients suffering from a disease or a disorder wherein an inhibition of protein prenylation, and more precisely wherein an inhibition of protein farnesylation is required, and in particular HGPS, progeria or anyone of the previous listed disease, which comprises at least a step of administration to a patient suffering thereof of an effective amount of a compound of anyone of formula (I), (II), (Ia), (Ib), (Ic), and (I'a) and (1) to (14) or one of its pharmaceutically acceptable salts.

The invention claimed is:

1. A method of treating diseases or disorders wherein an inhibition of protein prenylation is required comprising at least a step of administering to an individual in need thereof at least one compound or pharmaceutically acceptable salts thereof, enantiomers thereof, diastereoisomers thereof, or racemic mixtures thereof, wherein the compound is selected from the group consisting of (1)

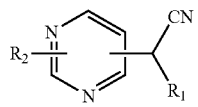

wherein $R_1$ is 2-pyridyl, 3-pyridyl or 4-pyridyl;

$R_2$ represents a group which is selected from the group consisting of:

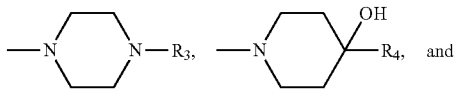 and

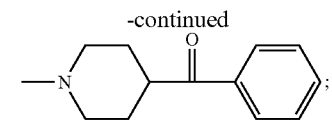

$R_3$ representing a group which is selected from the group consisting of:

an arylcarbonyl group, a heteroarylcarbonyl group, a $(C_1\text{-}C_4)$alkoxy-carbonylmethyl group, and a

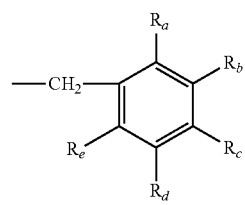

group, $R_a$, $R_b$, $R_c$, $R_d$ and $R_e$ being, independently a hydrogen atom, a halogen atom, a $(C_1\text{-}C_4)$alkyl group, or a $(C_1\text{-}C_4)$alkoxy group, or $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms, and R₄ being a phenyl group substituted by a halogen atom, or a benzyl group;
provided that
R₃ is not a 4-methylbenzyl group when R₁ is 2-pyridyl, and (2)

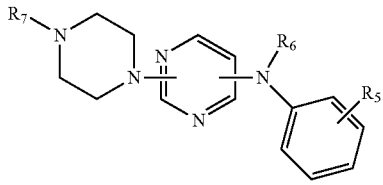

(II)

wherein
$R_5$ represents a hydrogen atom or a $(C_{1-4})$alkyl group;
$R_6$ represents a hydrogen atom or a $(C_{1-4})$alkyl group; and
$R_7$ represents a group which is selected from the group consisting of:
an arylcarbonyl group,
a heteroarylcarbonyl group optionally substituted by one or two groups selected from a $(C_{1-4})$alkyl group and a phenyl group,
a heteroarylacetyl group optionally substituted on the heteroaryl ring by a phenyl group,
a $(C_1-C_4)$alkoxy-carbonylmethyl group, and
a

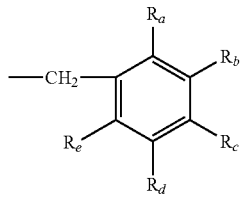

group, $R_a$, $R_b$, $R_c$, $R_d$ and $R_e$ being, independently a hydrogen atom, a halogen atom, a $(C_1-C_4)$alkyl group, or a $(C_1-C_4)$alkoxy group, or $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms,
provided that
$R_7$ is not an indol-3-ylacetyl group when $R_5$ and $R_6$ are both a methyl group.

2. The method of claim 1, wherein the compound is selected from the group consisting of (1)

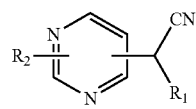

(I)

wherein
$R_1$ is 2-pyridyl, 3-pyridyl or 4-pyridyl;
$R_2$ represents a group which is selected from the group consisting of:

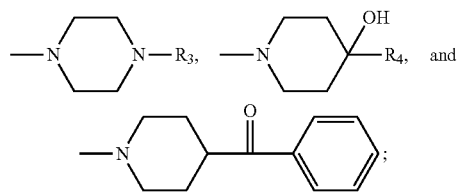

$R_3$ representing a group which is selected from the group consisting of:
an arylcarbonyl group,
a heteroarylcarbonyl group,
a $(C_1-C_4)$alkoxy-carbonylmethyl group, and
a

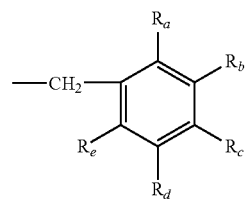

group, $R_a$, $R_b$, $R_d$ and $R_e$ being, independently a hydrogen atom, a halogen atom, a $(C_1-C_4)$alkyl group, or a $(C_1-C_4)$alkoxy group, and $R_c$ being a hydrogen atom, a halogen atom, or a $(C_1-C_4)$alkoxy group, or $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms,
and R₄ being a phenyl group substituted by a halogen atom, or a benzyl group;
and (2)

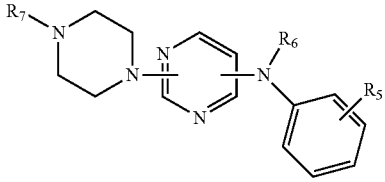

(II)

wherein
$R_5$ represents a hydrogen atom or a $(C_{1-4})$alkyl group;
$R_6$ represents a hydrogen atom or a $(C_{1-4})$alkyl group; and
$R_7$ represents a group which is selected from the group consisting of:
an arylcarbonyl group,
a heteroarylcarbonyl group optionally substituted by one or two groups selected from a $(C_{1-4})$alkyl group and a phenyl group,
a heteroarylacetyl group substituted on the heteroaryl ring by a phenyl group, a (C$_1$-C$_4$)alkoxy-carbonylmethyl group, and
a

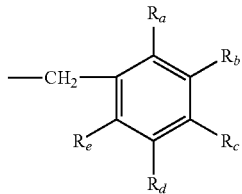

group, R$_a$, R$_b$, R$_c$, R$_d$ and R$_e$ being, independently a hydrogen atom, a halogen atom, a (C$_1$-C$_4$)alkyl group, or a (C$_1$-C$_4$)alkoxy group, or R$_a$ and R$_b$, or R$_b$ and R$_c$, or R$_c$ and R$_d$, or R$_d$ and R$_e$ together optionally forming with the carbon atom to which they are attached a 5- or 6-membered ring fused to the phenyl ring comprising two oxygen atoms.

3. The method of claim 1, wherein the compound is of formula (II)

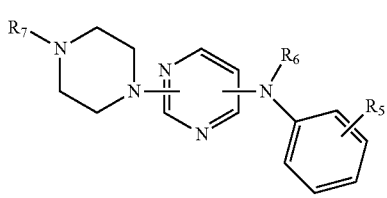

wherein
R$_5$ represents a hydrogen atom or a (C$_{1-4}$)alkyl group;
R$_6$ represents a hydrogen atom or a (C$_{1-4}$)alkyl group; and
R$_7$ represents a group which is selected from the group consisting of:
an arylcarbonyl group,
a heteroarylcarbonyl group optionally substituted by one or two groups selected from a (C$_{1-4}$)alkyl group and a phenyl group,
a heteroarylacetyl group substituted on the heteroaryl ring by a phenyl group,
a (C$_1$-C$_4$)alkoxy-carbonylmethyl group, and
a

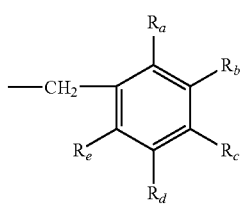

group, R$_a$, R$_c$, and R$_e$ being, independently a hydrogen atom, a halogen atom, a (C$_1$-C$_4$)alkyl group, or a (C$_1$-C$_4$)alkoxy group, R$_b$ and R$_d$ being independently a hydrogen atom or a (C$_1$-C$_4$)alkoxy group, or R$_a$ and R$_b$, or R$_b$ and R$_c$, or R$_c$ and R$_d$, or R$_d$ and R$_e$ together optionally forming with the carbon atom to which they are attached a 5- or 6-membered ring fused to the phenyl ring comprising two oxygen atoms.

4. The method of claim 1, wherein the compound is selected from the group consisting of (1)

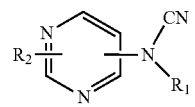

wherein
R$_1$ is 2-pyridyl, 3-pyridyl or 4-pyridyl;
R$_2$ represents a group which is selected from the group consisting of:

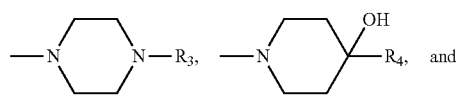

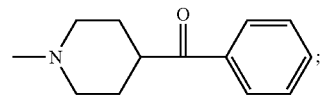

R$_3$ representing a group which is selected from the group consisting of:

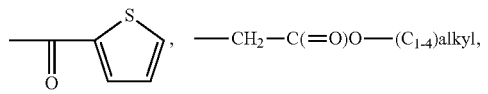

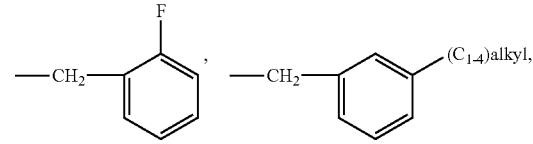

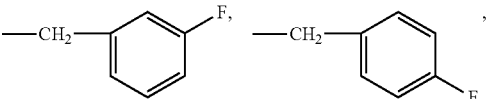

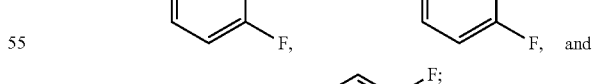

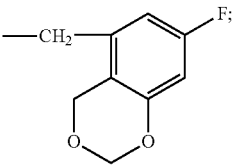

and R$_4$ being a phenyl group substituted by a halogen atom, or a benzyl group; and (2)

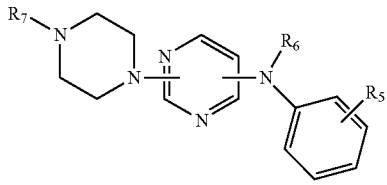

wherein

R₅ represents a hydrogen atom or a (C₁₋₄)alkyl group;

R₆ represents a hydrogen atom or a (C₁₋₄)alkyl group; and

R₇ represents a group which is selected from the group consisting of:

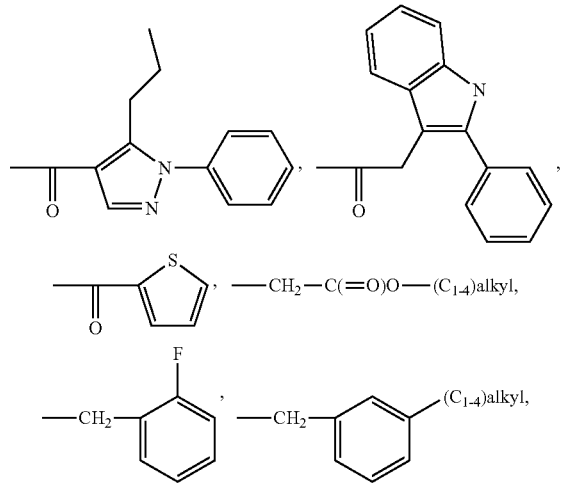

(1)

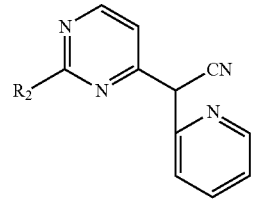

wherein R₂ represents a group which is selected from the group consisting of:

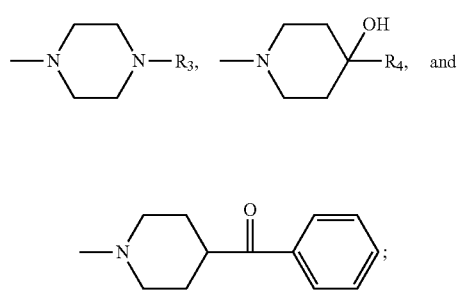

R₃ representing a group which is selected from the group consisting of:

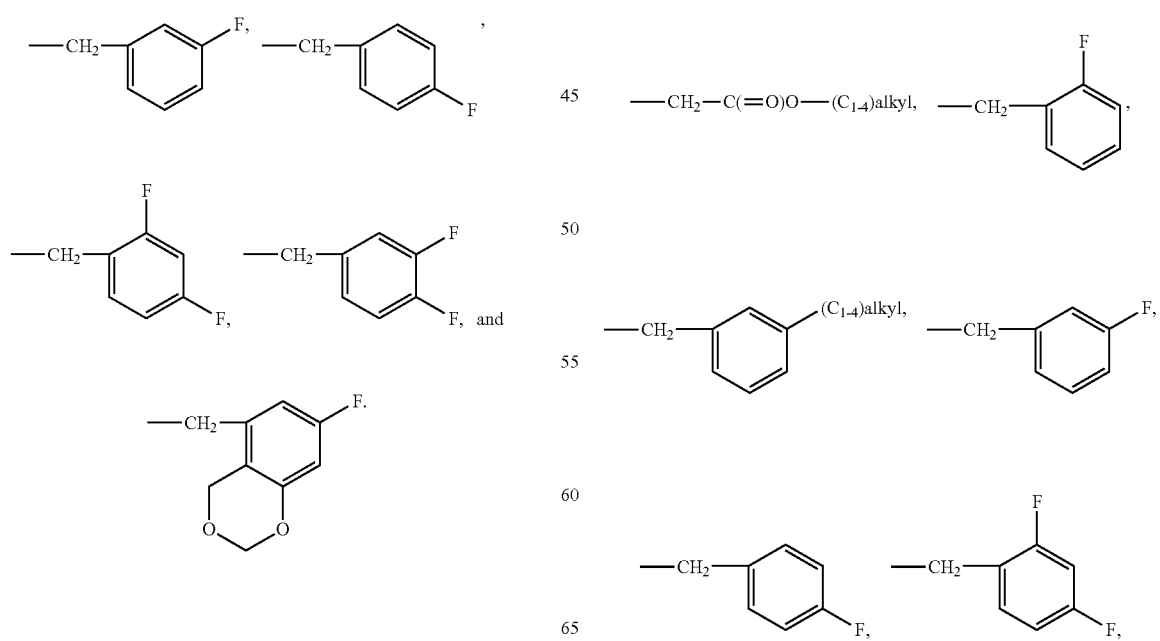

5. The method of claim 1, wherein the compound is selected from the group consisting of:

-continued (3) and R₄ being a phenyl group substituted by a halogen atom;

(2)

(1b) wherein R₃ represents a group which is selected from the group consisting of:

[structures: thiophene-C(=O)-, —CH₂—C(=O)O—(C₁₋₄)alkyl, —CH₂-(2-F-phenyl), —CH₂-(3-(C₁₋₄)alkyl-phenyl), —CH₂-(3-F-phenyl), —CH₂-(4-F-phenyl), —CH₂-(2,4-diF-phenyl), —CH₂-(3,4-diF-phenyl), and —CH₂-(benzodioxine); and]

-continued (Ic)

wherein R₄ a phenyl group substituted by a halogen atom, or a benzyl group.

6. The method of claim 1, wherein the compound is of formula (I'a):

(I'a)

wherein R₃ represents a group which is selected from the group consisting of:

[structures: —CH₂—C(=O)O—(C₁₋₄)alkyl, —CH₂-(2-F-phenyl), —CH₂-(3-(C₁₋₄)alkyl-phenyl), —CH₂-(3-F-phenyl), —CH₂-(4-F-phenyl), —CH₂-(2,4-diF-phenyl), —CH₂-(3,4-diF-phenyl), and —CH₂-(benzodioxine).]

7. The method of claim 1, wherein the compound is of formula (I'a):

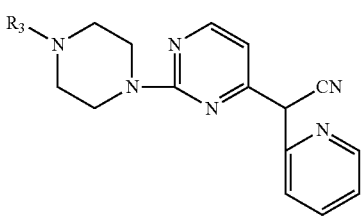

(I'a)

wherein R₃ represents a group which is selected from the group consisting of:

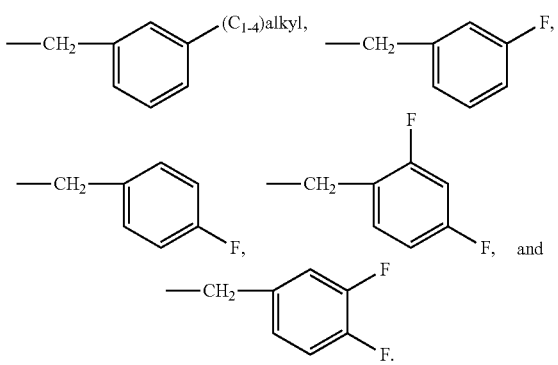

8. The method of claim 1, wherein the compound is of formula (II) wherein
$R_5$ represents a $(C_{1-4})$alkyl group;
$R_6$ represents a $(C_{1-4})$alkyl group; and
$R_7$ represents the following group

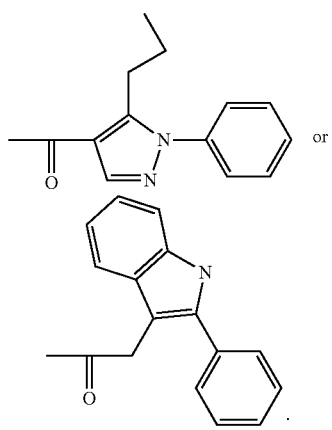

9. The method of claim 1, wherein the compound is selected from the group consisting of:
(1) {2-[4-(2-fluoro-benzyl)-piperazin-1-yl]-pyrimidin-4-yl}-pyridin-2-yl-acetonitrile
(2) {2-[4-(4-Chloro-phenyl)-4-hydroxy-piperidin-1-yl]-pyrimidin-4-yl}-pyridin-2-yl-acetonitrile
(3) [2-(4-Benzoyl-piperidin-1-yl)-pyrimidin-4-yl]-pyridin-2-yl-acetonitrile
(4) {2-[4-(3-Methyl-benzyl)-piperazin-1-yl]-pyrimidin-4-yl}-pyridin-2-yl-acetonitrile
(5) {2-[4-(4-Fluoro-benzyl)-piperazin-1-yl]-pyrimidin-4-yl}-pyridin-2-yl-acetonitrile
(6) {4-[4-(Cyano-pyridin-2-yl-methyl)-pyrimidin-2-yl]-piperazin-1-yl}-acetic acid ethyl ester
(7) {2-[4-(2,4-Difluoro-benzyl)-piperazin-1-yl]-pyrimidin-4-yl}-pyridin-2-yl-acetonitrile
(8) {2-[4-(6-Fluoro-4H-benzo[1,3]dioxin-8-ylmethyl)-piperazin-1-yl]-pyrimidin-4-yl}-pyridin-2-yl-acetonitrile
(9) {2-[4-(3-Fluoro-benzyl)-piperazin-1-yl]-pyrimidin-4-yl}-pyridin-2-yl-acetonitrile
(10) {2-[4-(3,4-Difluoro-benzyl)-piperazin-1-yl]-pyrimidin-4-yl}-pyridin-2-yl-acetonitrile
(11) Pyridin-4-yl-{6-[4-(thiophene-2-carbonyl)-piperazin-1-yl]-pyrimidin-4-yl}-acetonitrile
(12) [2-(4-Benzyl-4-hydroxy-piperidin-1-yl)-pyrimidin-4-yl]-pyridin-2-yl-acetonitrile
(13) {4-[6-(Methyl-m-tolyl-amino)-pyrimidin-4-yl]-piperazin-1-yl}-(1-phenyl-5-propyl-1H-pyrazol-4-yl)-methanone, and
(14) 1-{4-[6-(Methyl-m-tolyl-amino)-pyrimidin-4-yl]-piperazin-1-yl}-2-(2-phenyl-1H-indol-3-yl)-ethanone.

10. The method of claim 1, wherein the diseases or disorders are selected from a progeria disease, a neurodegenerative disease, a metabolic disease, a mitochondrial disease, an ocular disease, an inflammatory disease, a cardiovascular disease, a proliferative disease, an immune disease, cerebral infarction, skin aging, hormonal aging, or viral infection.

11. The method of claim 10 wherein the proliferative diseases are tumors or cancers, which are selected from bone tumors or cancers, brain tumors or cancers, kidney tumors or cancers, liver tumors or cancers, adrenal gland tumors or cancers, colorectal tumors or cancers, urinary bladder tumors or cancers, breast tumors or cancers, stomach tumors or cancers, ovaries tumors or cancers, colon tumors or cancers, rectum tumors or cancers, prostate tumors or cancers, pancreas tumors or cancers, lung tumors or cancers, non-small cell lung tumors or cancers, small cell lung tumors or cancers, vagina tumors or cancers, thyroid tumors or cancers, or the neck and head cancers or tumors.

12. The method of claim 1, wherein the compound is administered in a pharmaceutical composition.

13. A compound or pharmaceutically acceptable salts thereof selected from the group consisting of hydrochloride, hydrobromide, tartrate, fumarate, citrate, trifluoroacetate, ascorbate, triflate, mesylate, tosylate, formate, acetate and malate, enantiomers thereof, diastereoisomers thereof, or racemic mixtures thereof, wherein the compound is selected from the group consisting of (1)

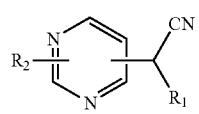

(I)

wherein
$R_1$ is 2-pyridyl, 3-pyridyl or 4-pyridyl;
$R_2$ represents a group which is selected from the group consisting of:

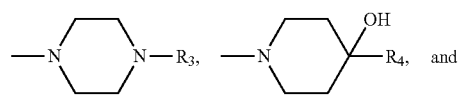

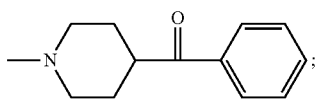

R₃ representing a group which is selected from the group consisting of:
an arylcarbonyl group,
a heteroarylcarbonyl group,
a $(C_1$-$C_4)$alkoxy-carbonylmethyl group, and
a

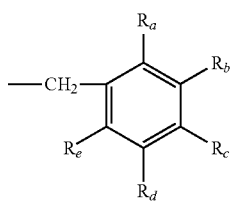

group, $R_a$, $R_b$, $R_c$, $R_d$ and $R_e$ being, independently a hydrogen atom, a halogen atom, a $(C_1$-$C_4)$alkyl group, or a $(C_1$-$C_4)$alkoxy group, or $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms,
and R₄ being a phenyl group substituted by a halogen atom, or a benzyl group;
provided that
R₃ is not a 4-methylbenzyl group when R₁ is 2-pyridyl, (2)

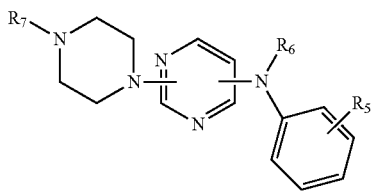

wherein
R₅ represents a hydrogen atom or a $(C_{1-4})$alkyl group;
R₆ represents a hydrogen atom or a $(C_{1-4})$alkyl group; and
R₇ represents a group which is selected from the group consisting of:
an unsubstituted arylcarbonyl group,
a heteroarylcarbonyl group optionally substituted by one or two groups selected from a $(C_{1-4})$alkyl group and a phenyl group,
a heteroarylacetyl group optionally substituted on the heteroaryl ring by a phenyl group,
a $(C_1$-$C_4)$alkoxy-carbonylmethyl group, and
a

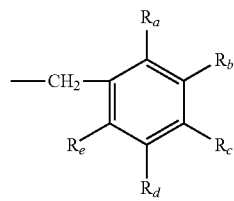

group, $R_a$, $R_b$, $R_c$, $R_d$ and $R_e$ being, independently a hydrogen atom, a halogen atom, a $(C_1$-$C_4)$alkyl group, or a $(C_1$-$C_4)$alkoxy group, or $R_a$ and $R_b$, or $R_b$ and $R_c$, or $R_c$ and $R_d$, or $R_d$ and $R_e$ together optionally forming with the carbon atom to which they are attached a 5- or 6-membered ring fused to the phenyl ring comprising two oxygen atoms,
provided that
R₇ is not an indol-3-ylacetyl group when R₅ and R₆ are both a methyl group (3)

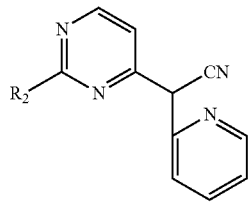

wherein R₂ represents a group which is selected from the group consisting of:

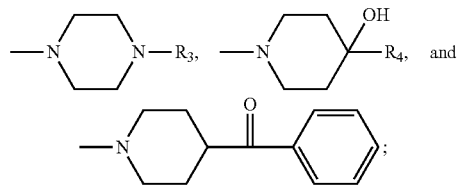

R₃ representing a group which is selected from the group consisting of:

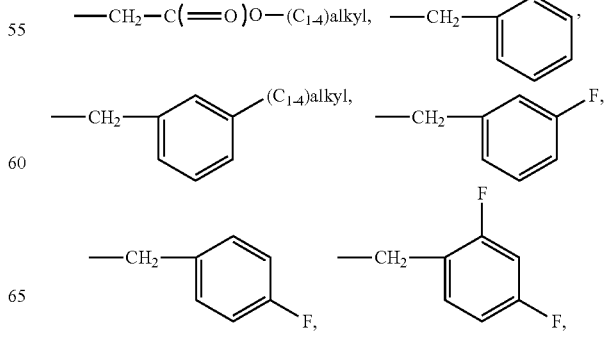

-continued (4)

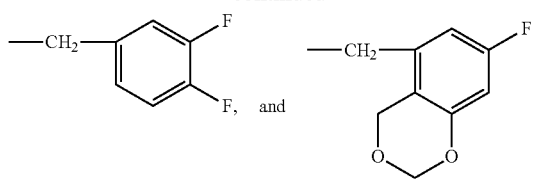

and R$_4$ being a phenyl group substituted by a halogen atom;

(4)

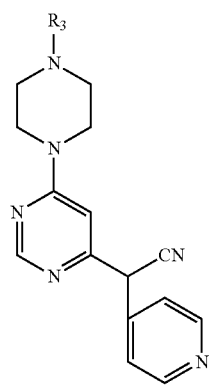

(Ib)

wherein R$_3$ represents a group which is selected from the group consisting of:

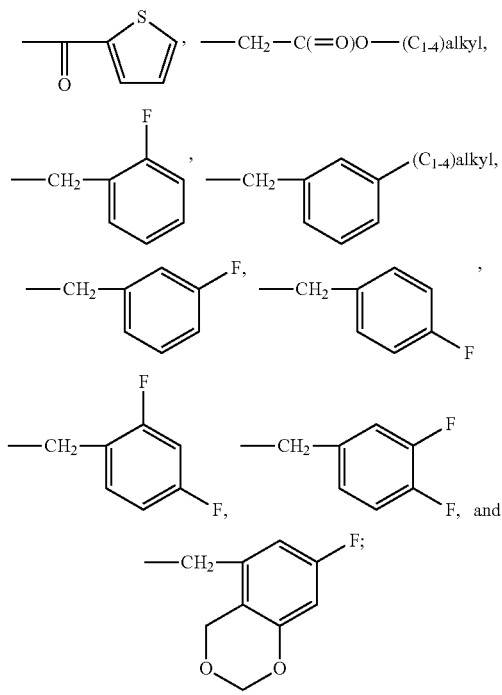

(5)

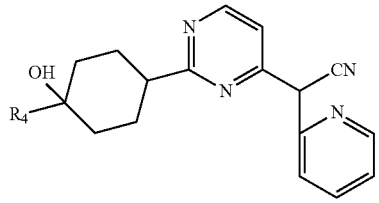

(Ic)

wherein R$_4$ a phenyl group substituted by a halogen atom, or a benzyl group, and (6)

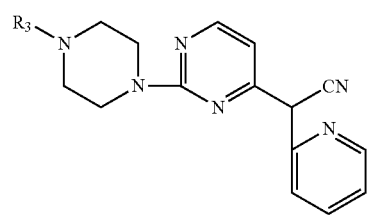

(I'a)

wherein R$_3$ represents a group which is selected from the group consisting of:

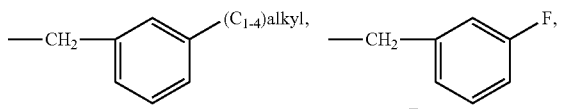

14. The compound of claim 13 selected from the group consisting of
(1) {2-[4-(2-fluoro-benzyl)-piperazin-1-yl]-pyrimidin-4-yl}-pyridin-2-yl-acetonitrile
(2) {2-[4-(4-Chloro-phenyl)-4-hydroxy-piperidin-1-yl]-pyrimidin-4-yl}-pyridin-2-yl-acetonitrile
(3) [2-(4-Benzoyl-piperidin-1-yl)-pyrimidin-4-yl]-pyridin-2-yl-acetonitrile
(4) {2-[4-(3-Methyl-benzyl)-piperazin-1-yl]-pyrimidin-4-yl}-pyridin-2-yl-acetonitrile
(5) {2-[4-(4-Fluoro-benzyl)-piperazin-1-yl]-pyrimidin-4-yl}-pyridin-2-yl-acetonitrile
(6) {4-[4-(Cyano-pyridin-2-yl-methyl)-pyrimidin-2-yl]-piperazin-1-yl}-acetic acid ethyl ester
(7) {2-[4-(2,4-Difluoro-benzyl)-piperazin-1-yl]-pyrimidin-4-yl}-pyridin-2-yl-acetonitrile
(8) {2-[4-(6-Fluoro-4H-benzo[1,3]dioxin-8-ylmethyl)-piperazin-1-yl]-pyrimidin-4-yl}-pyridin-2-yl-acetonitrile
(9) {2-[4-(3-Fluoro-benzyl)-piperazin-1-yl]-pyrimidin-4-yl}-pyridin-2-yl-acetonitrile

(10) {2-[4-(3,4-Difluoro-benzyl)-piperazin-1-yl]-pyrimidin-4-yl}-pyridin-2-yl-acetonitrile
(11) Pyridin-4-yl-{6-[4-(thiophene-2-carbonyl)-piperazin-1-yl]-pyrimidin-4-yl}-acetonitrile
(12) [2-(4-Benzyl-4-hydroxy-piperidin-1-yl)-pyrimidin-4-yl]-pyridin-2-yl-acetonitrile
(13) {4-[6-(Methyl-m-tolyl-amino)-pyrimidin-4-yl]-piperazin-1-yl}-(1-phenyl-5-propyl-1H-pyrazol-4-yl)-methanone, and
(14) 1-{4-[6-(Methyl-m-tolyl-amino)-pyrimidin-4-yl]-piperazin-1-yl}-2-(2-phenyl-1H-indol-3-yl)-ethanone.

15. A pharmaceutical composition comprising at least one compound as defined in claim 13 at least one pharmaceutically acceptable excipient.

16. A pharmaceutical composition comprising at least one compound as defined in claim 14 at least one pharmaceutically acceptable excipient.

\* \* \* \* \*

SEQUENCE LISTING

```
<160> NUMBER OF SEQ ID NOS: 9

<210> SEQ ID NO 1
<211> LENGTH: 21
<212> TYPE: DNA
<213> ORGANISM: Artificial Sequence
<220> FEATURE:
<223> OTHER INFORMATION: lamin A primer

<400> SEQUENCE: 1
tcttctgcct ccagtgtcac g                                      21

<210> SEQ ID NO 2
<211> LENGTH: 19
<212> TYPE: DNA
<213> ORGANISM: Artificial Sequence
<220> FEATURE:
<223> OTHER INFORMATION: lamin A primer

<400> SEQUENCE: 2
agttctgggg gctctgggt                                         19

<210> SEQ ID NO 3
<211> LENGTH: 22
<212> TYPE: DNA
<213> ORGANISM: Artificial Sequence
<220> FEATURE:
<223> OTHER INFORMATION: lamin C primer

<400> SEQUENCE: 3
caactccact ggggaagaag tg                                     22

<210> SEQ ID NO 4
<211> LENGTH: 17
<212> TYPE: DNA
<213> ORGANISM: Artificial Sequence
<220> FEATURE:
<223> OTHER INFORMATION: lamin C primer

<400> SEQUENCE: 4
cggcggctac cactcac                                           17

<210> SEQ ID NO 5
<211> LENGTH: 17
<212> TYPE: DNA
<213> ORGANISM: Artificial Sequence
<220> FEATURE:
<223> OTHER INFORMATION: Progerin primer

<400> SEQUENCE: 5
actgcagcag ctcgggg                                           17

<210> SEQ ID NO 6
<211> LENGTH: 16
<212> TYPE: DNA
<213> ORGANISM: Artificial Sequence
<220> FEATURE:
```

```
<223> OTHER INFORMATION: Progerin primer

<400> SEQUENCE: 6
tctgggggct ctgggc                                              16

<210> SEQ ID NO 7
<211> LENGTH: 14
<212> TYPE: DNA
<213> ORGANISM: Artificial Sequence
<220> FEATURE:
<223> OTHER INFORMATION: lamin A probe

<400> SEQUENCE: 7
actcgcagct accg                                                14

<210> SEQ ID NO 8
<211> LENGTH: 15
<212> TYPE: DNA
<213> ORGANISM: Artificial Sequence
<220> FEATURE:
<223> OTHER INFORMATION: lamin C probe

<400> SEQUENCE: 8
atgcgcaagc tggtg                                               15

<210> SEQ ID NO 9
<211> LENGTH: 15
<212> TYPE: DNA
<213> ORGANISM: Artificial Sequence
<220> FEATURE:
<223> OTHER INFORMATION: Progerin probe

<400> SEQUENCE: 9
cgctgagtac aacct                                               15
```